US006120751A

United States Patent [19]

Unger

[11] Patent Number: 6,120,751
[45] Date of Patent: *Sep. 19, 2000

[54] CHARGED LIPIDS AND USES FOR THE SAME

[75] Inventor: Evan C. Unger, Tucson, Ariz.

[73] Assignee: ImaRx Pharmaceutical Corp., Tucson, Ariz.

[*] Notice: This patent issued on a continued prosecution application filed under 37 CFR 1.53(d), and is subject to the twenty year patent term provisions of 35 U.S.C. 154(a)(2).

[21] Appl. No.: 08/925,353

[22] Filed: Sep. 8, 1997

Related U.S. Application Data

[63] Continuation-in-part of application No. 08/823,791, Mar. 21, 1997, and a continuation-in-part of application No. 08/851,780, May 6, 1997, and a continuation-in-part of application No. 08/877,826, Jun. 18, 1997, and a continuation-in-part of application No. 08/887,215, Jul. 2, 1997.

[51] Int. Cl.⁷ .......................... A61K 49/04; A61K 9/50; A61K 9/127; B01J 13/02
[52] U.S. Cl. .................. 424/9.51; 424/9.52; 424/450; 424/502; 264/4.1; 264/4; 428/402.2
[58] Field of Search ................. 424/450, 9.52, 424/9.51, 489, 498, 502, 1.21, 9.321, 812; 514/937; 264/4, 4.1, 4.32, 4.33; 427/2.14, 213.3, 213.31; 428/402, 402.24, 402.2; 436/829

[56] References Cited

U.S. PATENT DOCUMENTS

| | | |
|---|---|---|
| 3,015,128 | 1/1962 | Sommerville et al. ............. 18/2.6 |
| 3,293,114 | 12/1966 | Kenaga et al. ............. 162/168 |
| 3,401,475 | 9/1968 | Morehouse et al. ............. 40/306 |
| 3,479,811 | 11/1969 | Walters ............. 57/153 |
| 3,488,714 | 1/1970 | Walters et al. ............. 161/161 |
| 3,532,500 | 10/1970 | Priest et al. ............. 96/91 |
| 3,594,326 | 7/1971 | Himmel et al. ............. 252/316 |
| 3,615,972 | 10/1971 | Morehouse et al. ............. 156/79 |
| 3,647,784 | 3/1972 | Stein et al. ............. 260/239.55 R |
| 3,649,620 | 3/1972 | Ercoli et al. ............. 260/239.55 |
| 3,650,831 | 3/1972 | Jungermann et al. ............. 134/27 |
| 3,732,172 | 5/1973 | Herbig et al. ............. 252/316 |
| 3,873,564 | 3/1975 | Schneider et al. ............. 260/309.6 |
| 3,945,956 | 3/1976 | Garner ............. 260/2.5 B |
| 3,960,583 | 6/1976 | Netting et al. ............. 106/122 |
| 3,968,203 | 7/1976 | Spitzer et al. ............. 424/47 |
| 4,027,007 | 5/1977 | Messina ............. 424/46 |
| 4,078,052 | 3/1978 | Papahadjopoulos ............. 424/36 |
| 4,089,801 | 5/1978 | Schneider ............. 252/316 |
| 4,108,806 | 8/1978 | Cohrs et al. ............. 521/54 |
| 4,138,383 | 2/1979 | Rembaum et al. ............. 260/29.7 H |
| 4,162,282 | 7/1979 | Fulwyler et al. ............. 264/9 |
| 4,179,546 | 12/1979 | Garner et al. ............. 521/56 |
| 4,192,859 | 3/1980 | Mackaness et al. ............. 424/5 |
| 4,224,179 | 9/1980 | Schneider ............. 252/316 |
| 4,229,360 | 10/1980 | Schneider et al. ............. 260/403 |
| 4,265,251 | 5/1981 | Tickner ............. 128/660 |
| 4,276,885 | 7/1981 | Tickner et al. ............. 128/660 |
| 4,310,505 | 1/1982 | Baldeschwieler et al. ............. 424/1 |
| 4,310,506 | 1/1982 | Baldeschwieler et al. ............. 424/1 |
| 4,315,514 | 2/1982 | Drewes et al. ............. 128/653 |
| 4,331,654 | 5/1982 | Morris ............. 424/38 |
| 4,342,826 | 8/1982 | Cole ............. 435/7 |

(List continued on next page.)

FOREIGN PATENT DOCUMENTS

| | | |
|---|---|---|
| 641363 | 3/1990 | Australia . |
| B-30351/89 | 3/1993 | Australia . |
| 0 107 559 | 5/1984 | European Pat. Off. . |
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1. | 3/1990 | European Pat. Off. . |
| 0 361 894 | 4/1990 | European Pat. Off. . |
| 0 368 486 A2 | 5/1990 | European Pat. Off. . |
| 0 382 451 A2 | 8/1990 | European Pat. Off. . |
| 0 216 730 | 1/1991 | European Pat. Off. . |
| 0 422 938 B1 | 4/1991 | European Pat. Off. . |
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 579 703 B1 | 1/1994 | European Pat. Off. . |
| 0 727 225 A2 | 8/1996 | European Pat. Off. . |

(List continued on next page.)

OTHER PUBLICATIONS

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Bio–Chemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

(List continued on next page.)

*Primary Examiner*—Jose' G. Dees
*Assistant Examiner*—Michael G. Hartley
*Attorney, Agent, or Firm*—Woodcock Washburn Kurtz Mackiewicz & Norris LLP

[57] ABSTRACT

The present invention is directed to charged lipids, compositions comprising charged lipids, and the use of these compositions in drug delivery, targeted drug delivery, therapeutic imaging and diagnostic imaging, as well as their use as contrast agents.

20 Claims, 4 Drawing Sheets

U.S. PATENT DOCUMENTS

| | | | |
|---|---|---|---|
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 260/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | 424/11 |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,663,161 | 5/1987 | Mannino et al. | 424/89 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,775,522 | 10/1988 | Clark, Jr. | 424/9 |
| 4,775,958 | 10/1988 | Feinstein | 128/660.01 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,863,965 | 9/1989 | Jansen et al. | 514/576 |
| 4,865,836 | 9/1989 | Long, Jr. | 424/5 |
| 4,871,488 | 10/1989 | Mannino et al. | 264/4.6 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,114,703 | 5/1992 | Wolf et al. | 424/5 |
| 5,123,414 | 6/1992 | Unger | 128/654 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,234,680 | 8/1993 | Rogers, Jr. et al. | 424/9 |
| 5,271,928 | 12/1993 | Schneider et al. | 424/9 |
| 5,276,146 | 1/1994 | Breillatt, Jr. et al. | 530/413 |
| 5,281,408 | 1/1994 | Unger | 424/4 |
| 5,305,757 | 4/1994 | Unger et al. | 128/662.02 |
| 5,310,540 | 5/1994 | Giddy et al. | 424/9 |
| 5,312,617 | 5/1994 | Unger et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhatdt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,466,467 | 11/1995 | Singh | 424/450 |
| 5,469,854 | 11/1995 | Unger et al. | 128/662.02 |
| 5,470,582 | 11/1995 | Supersaxo et al. | 424/489 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,498,601 | 3/1996 | Sato et al. | 514/17 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,512,295 | 4/1996 | Kornberg et al. | 424/450 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,547,656 | 8/1996 | Unger | 424/9.4 |
| 5,552,133 | 9/1996 | Lambert et al. | 424/9.52 |
| 5,552,155 | 9/1996 | Bailey et al. | 424/450 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |

| | | | |
|---|---|---|---|
| 5,558,855 | 9/1996 | Quay | 424/9.5 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,573,751 | 11/1996 | Quay | 424/9.52 |
| 5,578,292 | 11/1996 | Schneider et al. | 424/9.51 |
| 5,580,575 | 12/1996 | Unger et al. | 424/450 |
| 5,585,112 | 12/1996 | Unger et al. | 424/450 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| B1 4,229,360 | 11/1991 | Schneider et al. | 260/403 |

FOREIGN PATENT DOCUMENTS

| | | |
|---|---|---|
| 62-286534 | 12/1987 | Japan . |
| 63-60943 | 3/1988 | Japan . |
| 1044680 | 10/1966 | United Kingdom . |
| 2193095A | 2/1988 | United Kingdom . |
| WO 80/02365 | 11/1980 | WIPO . |
| WO 82/01642 | 5/1982 | WIPO . |
| US85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/21382 | 10/1992 | WIPO . |
| WO 93/05819 | 1/1993 | WIPO . |
| WP 93/00933 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/06477 | 3/1994 | WIPO . |
| WO 94/09829 | 5/1994 | WIPO . |
| WO 94/16739 | 8/1994 | WIPO . |
| WO 94/21302 | 9/1994 | WIPO . |
| WO 94/28780 | 12/1994 | WIPO . |
| WO 95/06518 | 3/1995 | WIPO . |
| WO 95/07072 | 3/1995 | WIPO . |
| WO 95/09648 | 4/1995 | WIPO . |
| WO 95/23615 | 9/1995 | WIPO . |
| WO 95/27478 | 10/1995 | WIPO . |
| WO 96/04018 | 2/1996 | WIPO . |
| WO 96/09793 | 4/1996 | WIPO . |
| WO 96/25942 | 8/1996 | WIPO . |
| WO 96/36286 | 11/1996 | WIPO . |

OTHER PUBLICATIONS

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H.,. ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultlrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.,* vol. 92, No. 8, pp. 2450–2460 (1970).

Mahlradt et al., "Vitamin B6 Analogs: An Improved Synthesis of 5–Deoxypyridoxal", *New Compounds,* vol. 10, pp. 129–130 (1967).

Chapman D., "Physiochemical Properties of Phospholipids and Lipid Water Systems", *Liposome Technology,* Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.,* vol. 23, pp. S294–S297, Sep. 1988.

Fritzsch et al., "Preclinical and Clinical Results with an Ultrasonic Contrast Agent", *Inv. Rad.,* vol. 23, pp. S302–S305, Sep. 1988.

Brochure, *Experience,* Sonicator™, Heat Systems—Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.,* vol. 108, pp. 2321–2327 (1986).

Regen, "Polymerized Vesicles", *J. Am. Chem. Soc.,* vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC),* vol. 44(3), pp. 322–326 (1981) (abstract).

J. Vion–Dury et al., *J. Pharmacol. Exper. Ther.,* vol. 250(3), pp. 1113–1118 (1989) (abstract).

M.R. Zalutsky et al., *Invest. Radiol.,* vol. 22(2), pp. 141–147 (1987) (abstract).

Crowe et al., *Archives of Biochemistry and Biophysics,* vol. 242, pp. 240–247 (1985).

Crowe et al., *Archives of Biochemistry and Biophysics,* vol. 220, pp. 477–484 (1983).

Dorland's Illustrated Medical Dictionary, p. 946, 27th ed. (W.B. Saunders Company, Philadelphia 1988).

*Liposome Technology,* Gregoriadis, G., ed., vol. I, pp. 1–18, 29–35, 51–65 and 79–107 (CRC Press Inc., Boca Raton, FL, (1984).

Madden et al., *Chemistry and Physics in Lipids,* vol. 53, pp. 37–46 (1990).

Sinkula et al., *J. Pharm. Sci.,* vol. 64, pp. 181–210 (1975).

Shiina et al., "Hyperthermiaby Low–frequency Synthesized Ultrasound", *IEEE Engineering,* pp. 879–880, vol. 2 (1988) (abstract).

McAvoy et al., *IEEE Engineering,* Ultrasonics Symposium Proceedings, vol. 2, pp. 677–1248 (1989) (abstract).

Chapman et al., "Biomembrane Phase Transitions", *J. Biol. Chem.,* 1974, 249:2512–2521.

Hug et al., "Liposomes for the Transformation of Eukaryotic Cells", *Biochimica et Biophysica Acta,* 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.,* 1965, 13:238–252.

Carson et al., *Ultrasound in Med. & Biol.* 3, 1978, 341–350.

Kost et al., *Polymers in Medicine II: Biomedical and Pharmaceutical Applications,* "Ultrasonic Modulated Drug Delivery Systems", Chiellini et al., eds., (Plenum Press, New York and London), pp. 387–396 (1985).

deGier et al., "Relations Between Liposomes and Biomembranes", *Annals of The New York Academy of Sciences,* 1978, 308:85–99.

Felgner et al., "Lipofection: A highly efficient, lipid–mediated DNA–transfection procedure", *Proc. Natl. Acad. Sci.,* 1987, 84:7413–7417.

Gabizon et al., "Liposome formulations with prolonged circulation time in blood and enhanced uptake by tumors", *Proc. Natl. Acad. Sci.,* 1988, 85:6949–6953.

Garelli, et al., *Biochimica et Biophysica Acta,* vol. 1127:41–48 (1992).

Kawai et al., "New Procedure for DNA Transfection with Polycation and Dimethyl Sulfoxide", *Molecular and Cellular Biology,* 1984, 4:1172–1174.

Kuo et al., "Metallocene Antitumor Agents. Solution and Solid–State Molybdenocene Coordination . . . ", *J. Am. Chem. Soc.,* 1991, 113:9027–9045.

*Mammalian Cell Biotechnology: A Practical Approach,* M. Butler, 1991 (Oxford University Press, New York), p. 57–70.

Mathiowitz et al., "Photochemical Rupture of Microcapsules: A Model System", *Journal of Applied Polymer Science,* 1981, 26:809–822.

May et al., "Cationic Liposomes Enable Bovine Herpesvirus Type 2 DNA to Infect Cells", *Acta virol.,* 1991, 35:107.

Pozansky et al., "Biologica Approaches to the Controlled Delivery of Drugs: A Critical Review", *Pharmacol, Rev.,* 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature,* 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE,* 1992, O–7803–0785, pp. 354–355.

Williams, "Human Gene Therapy: Searching for Better Vectors", *ASM News* [American Society for Microbiology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science,* vol. 35, pp. 755–774 (1988).

Sankaram et al., "Cholesterol–Induced Fluid–Phase Immiscibility in Membranes", *Proc. Natl. Acad. Sci.,* vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology,* "Detection of Intracardiac Blood Flow by Pulsed Echo–Ranging", pp. 415–418 (1971).

Feigenbaum et al., *Circulation,* "Identification of Ultrasound Echoes from the Left Ventricle by Use of Intracardiac Injections of Indocyanine Green", vol. XL1, pp. 615–621 (1970).

Santaella, et al., *FEBS 13463,* "Extended In Vivo Blood Circulation Time of Fluorinated Liposomes", vol. 336, No. 3, pp. 481–484 (1993).

Brown and Langer, *Annual Review Medicine,* 1988, 39:221 29, Annual Review, Inc., "Transdermal Delivery of Drugs", pp. 221–229.

Moseley, et al., *Microbubbles: A Novel MR Susceptibility Contrast Agent,* abstract, 1991 Napa, California Meeting of the Society for Magnetic Resonance in Medicine.

Ter–Pogossia *Tomography,* Kee, et al., n, "Physical Principles and Instrumentation", *Computed Body* eds., Raven Press, New York, Chapter 1, pp. 1–7 (1988).

Aronberg, "Techniques", *Computed Body Tomography,* Kee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second-harmonic emissions," pp. 217–224.

Dittrich, "Cardiac Muscle Ischemia and Infarction", The Second Annual International Symposium on Contrast Agents in Diagnostic Ultrasound, Atlantic City, NJ (May 7, 1996) (abstract).

Pantely, "Intravenous Contrast Echocardiography–Tissue Imaging & Quantification of Coronary Blood Flow", The Second Annual International Symposium on Contrast Agents in Diagnostic Ultrasound, Atlantic City, NJ (May 7, 1996) (abstract).

Schutt et al., "Osmotically Stabilized Microbubble Sonographic Contrast Agents", *Acad. Radiol.,* vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta,* 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.,* 22(4), pp. 1403–1408 (1994).

Chang et al., "Semipermeable Aqueous Microcapsules", *Canadian J. Of Phys. And Pharm.,* 1996, 44, 115–128.

Chang, "Semipermeable Microcapsules", *Science,* 1964, 146, 524–525.

Deasy, *Microencapsulation and Related Drug Processes,* 1983, vol. 20, Chs. 9 and 10, 195–240 (Marcel Dekker, Inc., NY).

Yeung et al., "Preparation of Microencapsulated Liposomes", *J. Microencapsulation,* 1988, 5, 331–337.

Mattrey et al., Gas Emulsions as Ultrasound Contrast Agents; Preliminary Results in Rabbits and Dogs, *Investigative Radiology,* vol. 29, Jun. Supp. 2, pp. S139–S141, 1994.

Meltzer et al., Transmission of Ultrasonic Contrast Through the Lungs, *Ultrasound in Med. & Biol.,* vol. 7, No. 4, 377–384, 1981.

PR Newswire, Apr. 1, 1986.

Swanson et al., Chapter 22, "Enhancement Agents for Ultrasound: Fundamentals", *Pharmaceuticals In Medical Imaging,* pp. 682–687 (1990).

Ophir et al., "Contrast Agents in Diagnostic Ultrasound", *Ultrasound in Med. & Biol.,* vol. 15, No. 4, pp. 319–333 (1989).

Jacobs, "Intraocular gas measurement using A–scan ultrasound", *Current Eye Research,* vol. 5, No. 8, pp. 575–578 (1986).

Lincoff et al., "Intravitreal Expansion of Perfluorocarbon Bubbles", *Arch. Ophthalmol.,* 1980, 98, 1646.

Lincoff et al., "Intravitreal Longevity of Three Perfluorocarbon Gases", *Arch Opthalmol.,* 1980, 98, 1610–1611.

Lincoff et al., "The Perfluorocarbon Gases in Treatment of Retinal Detachment", *Ophthalmology,* 1983, 90(5), 546–551.

Gardner et al., "A Survey of Intraocular Gas Use in North America", *Arch. Ophthalmol.,* 1988, 106, 1188–1189.

Unger et al., "Liposomal MR Contrast Agents", *J. Liposome Research,* 1994, 4(2), 811–834.

Feinstein, Steven B., "Myocardial Perfusion Imaging: Contrast Echocardiography Today and Tomorrow," *Journal of the American College of Cardiology,* 8(1):251–253 (1986).

Keller et al., "The Behavior of Sonicated Albumin Microbubbles Within the Microcirulation: A Basis for Their Use During Myocardial Contrast Echocardiography", *Circulation Res.,* 65(2):458–465 (1989).

Lincoff et al., "Perfluoro–n–butane: A Gas for Maximum Duration Retinal Tamponade," *Arch Ophthalmology,* 101:460–462 (1983).

*Remington's Pharmaceutical Sciences,* John Hoover, managing ed., Mack Publishing Company, Easton, PA, pp. 295–298; 736; 1242–1244 (1975).

*Handbook of Pharmaceutical Excipients,* American Pharmaceutical Association, Washington, D.C. and The Pharmaceutical Society of Great Britain, London, England, pp. 181–183 (1986).

Miller et al., "Physiochemical Approaches to the Mode of action of General Anesthetics," *J. Amer. Soc. Anesthesiologists,* 36(4):339–351 (1972).

"Properties and Applications of the 'Freon' Fluorobcarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials,* 11:713–717 (1990).

Abraham et al., "Function and Regulation of the Murine Lymphocyte CD2 Receptor", *J. Leukocyte Biol.,* 1991, 49, 329–341.

Al–Muhammad et al., "Studies on the formulation and in vivo release of ophthalmic liposomes containing dexamethasone sodium phosphate", *J. Microencapsulation,* 1996, 13(2), 123–130.

Allcock, H.R., "Covalent Linkage of Proteins to Surface–Modified Poly(organophosphazenes): Immobilization of Glucose–6–Phosphate Dehydrogenase and Trypsin", *Macromolecules,* 1986, 19, 1502–1508.

Allcock, H.R., "Schiff Base Coupling of Cyclic and High-Polymeric Phosphazenes to Aldehydes and Amines: Chemotherapeutic Models", *Macromolecules*, 1981, 14, 1616–1622.

Bloemberger, N., "Proton Relaxation Times in Paramagnetic Solutions", *J. Chem. Phys.*, 1957, 27(2), 572–573 and 595–596.

Canfield et al., "Incorporation of β–Carotene into Mixed Micelles", *Methods in Enzymology*, 1990, 189, 418–422.

Cesano et al., "Treatment of experimental glioblastoma with a human major histocompatibility complex nonrestricted cytotoxic T cell line", *Cancer Res.*, 1995, 55(1), 96–101 (Abstract Only).

Cullen et al., "Sequence Requirements for Ligand Binding and Cell Surface Expression of the TAC Antigen a Human Interleukin Receptor", *J. Biol. Chem.*, 1988, 263(10), 4900–4906 (Abstract Only).

De Jagar, R. et al., "Current Status of Cancer Immunodetection with Radiolabeled Human Monoclonal Antibodies", *Seminars in Nuclear Med.*, 1993, 23(2), 165–179.

Elgorab et al., "Solubilization of β–Carotene and Retinol into Aqueous Solutions of Mixed Micelles", *Biochem. Biophys. Acta*, 1973, 306, 58–66.

Falconi et al., "Oral Long–Lasting Estrogenic Activity of Estradiol 3–Benzoate 17–Cyclooctenyl Ether", *Steroids*, 1972, 20(5), 627–638.

Farsh et al., "In–vivo studies in the treatment of oral ulcers with liposomal dexamethasone sodium phosphate", *J. Microencapsulation*, 1996, 13(5), 537–544.

Fedorak et al., "A novel colon–specific steroid prodrug enhances sodium chloride absorption in rat colitis", *Am. J. Physiol.*, 1995, 269, G210–218.

Fendler et al. (eds.), *Catalysis in Micellar and Macromolecular Systems*, Academic Press, NY 1975.

Fremont et al., "Biophysical studies of T–cell receptors and their ligands", *Curr. Opin. Immunol.*, 1996, 8, 93–100.

Gaffen et al., "Signaling through the interleukin 2 receptor beta chain activates a STAT–5–like DNA–binding activity", *Proc. Natl. Acad. Sci. USA*, 1995, 92(16), 7192–7196 (Abstract Only).

Gioanni, J. et al., "Characterization of a New Surface Epitope Specific for Human Epithelial Cells Defined by a Monoclonal Antibody and Application to Tumor Diagnosis", *Cancer Res.*, 1987, 47, 4417–4424.

Goundalkar et al., "Chemical Modification of Triamcinolone Acetonide to Improve Liposomal Encapsulation", *J. Pharm. Sciences*, 1984, 73(6), 834–835.

Hemar et al., "Endocytosis of Interleukin 2 Receptors in Human T Lymphocytes: Distinct Intracellular Localization and Fate of the Receptor α, β, and γ Chains", *J. Cell Biol.*, 1995, 129, 55–64.

Hochhaus et al., "A Selective HPLC–RIA for Dexamethasone and its Prodrug Dexamethasone–21–sulphobenzoate Sodium in Biological Fluids", *Biomed. Chrom.*, 1992, 6, 283–286.

Hori et al., "Characteristics of the IL–2 Receptor Expressed on Large Granular Lymphocytes from Patients with Abnormally Expanded Large Granular Lymphocytes Implication of a Non–Tac IL–2 Binding Peptide", *J. Immunol.*, 1988, 140(12), 4199–4203 (Abstract Only).

Kawabata, K. et al., "Effect of second–harmonic superimposition on efficient induction of sonochemical effect", *Ultrasonics Sonochemistry*, 1966, 3, 1–5.

Kersh et al., "Structural Basis for T Cell Recognition of Altered Peptide Ligands: A Single T Cell Receptor Can Productively Recognize a Large Continuum of Related Ligands", *J. Exp. Med.*, 1996, 184, 1259–1268.

Kuhl et al., "A New Class of Long–Acting Hormonal Steroid Preparation: Synthesis of Oligomeric Estradiol Derivatives", *Steroids*, 1973, 22(1), 73–87.

Kuo et al., "Structure–Function Relationships for the Interleukin 2–Receptor System I. Localization of a Receptor Binding Site on Interleukin 2", *J. Immunol.*, 1986, 137(5), 1538–1543 (Abstract Only).

Legrue et al., "The Role of Receptor–Ligand Endocytosis and Degradation in Interleukin–2 Signaling and T–Lymphocyte Proliferation", *Lymphokine Cytokine Res.*, 1991, 10(6), 431–436.

Lopez–Garcia et al., "Intra–articular therapy of experimental arthritis with a derivative of triamcinolone acetonide incorporated in liposomes", *J. Pharm. Pharmacol.*, 1993, 45, 576–578.

Lubinski et al., "Increased Binding of IL–2 and Increased IL–2 Receptor Messenger RNA Synthesis are Expressed by an NK–Like Cell Kine in Response to IL–1", *J. Immunol.*, 1988, 140(6), 1903–1909 (Abstract Only).

McLoed et al., "A Glucocorticoid Prodrug Facilitates Normal Mucosal Function in Rat Colitis Without Adrenal Suppression", *Gastroenterol.*, 1994, 106, 405–413.

Merimsky, O. et al., "Antigens and Antibodies in Malignant Melanoma", *Tumor Biol.*, 1994, 15, 188–202.

Miedel et al., "Structural Analysis of Recombinant Soluble Human Interleukin", *Biochem. Biophys. Res. Commun.*, 1988, 154(1), 373–379 (Abstract Only).

Miescher et al., "CCLXXVII. The Activation of the Male Sex Hormones. II.", *Activation of Male Sex Hormones*, 1936, 1977–1990.

Moreau et al., "Characterization of a monoclonal antibody directed against the NH2 terminal area of interleukin–2 (IL–2) and inhibiting specifically the binding of IL–2 to IL–2 receptor beta chain (IL–2R–beta)", *Mol. Immunol.*, 1995, 32, 14–15 (Abstract Only).

Nicol, L. et al., "Immunoscintigraphie Des Mélanomes Malins", *Pathologie Biologie*, 1990, 38(8), 866–869 (Summary of article in English).

O'Connor et al., "Growth Factor Requirements of Childhood Acute T–Lymphoblastic Leukemia: Correlation Between Presence of Chromosomal Abnormalities and Ability to Grow Permanently In Vitro", *Blood*, 1991, 77(7), 1534–1545.

Shahinian, S. et al., "A novel strategy affords high–yield coupling of antibody Fab' fragments to liposomes", *Biochimica et Biophysica Acta*, 1995, 1239, 157–167.

Shinoda, K. et al., "The Formation of Micelles", *Colloidal Surfactant*, Academic Press, New York, 1963, Chapter 1, 1–88.

Solomon, I., "Relaxation Processes in a System of Two Spins", *Phys. Rev.*, 1955, 99(2), 559–565.

Sutherland et al., "Color Doppler Myocardial Imaging: A New Technique for the Assessment of Myocardial Function", *J. Am. Soc of Echocardiogr*, 1994, 7(5), 441–458.

Tagliaferri, P. et al., "Pharmacological modulation of peptide growth factor receptor expression on tumor cells as a basis for cancer therapy", *Anti–Cancer Drugs*, 1994, 5, 379–393.

Thorpe, P.E. et al., "Antibody–directed targeting of the vasculature of solid tumors", *Breast Cancer Res. and Treatment*, 1995, 36, 237–251.

Tsudo et al., "Contribution of a P75 Interleukin 2 Binding Peptide to a High–Affinity Interleukin 2 Receptor Complex", *Proc. Natl. Acad. Sci. USA,* 1987, 84(12), 4215–4218 (Abstract Only).

Tsuji, Y. et al., "Identification of Two Different Surface Epitopes of Human Ovarian Epithelial Carcinomas by Monoclonal Antibodies", *Cancer Res.,* 1985, 45, 2358–2362.

Ulendorf, "Physics of Ultrasound Contrast Imaging: Scattering in The Linear Range", *IEEE Transactions on Ultrasonics, Ferroelectrics, and Frequency Control,* 1994, 41(1), 70–79.

Van Dougen et al., "Progress in radioimmunotherapy of head and neck cancer", *Oncology Reports,* 1994, 1, 259–264.

Wallner et al., "Primary Structure of Lymphocyte Function–Associated Antigen 3 (LFA–3): The Ligand of the T Lymphocyte CD2 Glycoprotein", *J. Experimental Med.,* 1987, 166, 923–932.

Weiss et al., "Cell Surface Molecules and Early Events Involved in Human T Lymphocyte Activation", *Adv. Immunol.,* 1987, 41, 1–38.

Wiegent et al., "The HTLV–III Envelope Protein Contains a Hexapeptide Homologous to a Region of Interleukin–2 That Binds to the interleukin–2 Receptor", *Biochem. Biophys. Res. Commun.,* 1986, 139(1), 367–374.

Wu, T.Z., "Immunology of the human papilloma virus in relation to cancer", *Curr. Opin. In Immunol.,* 1994, 6, 746–754.

Xueyong, Z. et al., "Use of MG Series Monoclonal Antibodies in the Diagnosis and Experimental Targeting Therapy of Gastric Cancer", *Chin. Med. Sci. J.,* 1991, 6(1), 56–59.

*Concise Encyclopedia of Biochemistry,* Second Edition, Walter de Gruyter & Co., 1988, 282–283.

Eibl, "Phospholipid synthesis: Oxazaphospholanes and dioxaphospholanes as intermediates", *Proc. Natl. Acad. Sci. USA,* 1978, 75(9), 4074–4077.

Hansen et al., "An Improved Procedure for the Synthesis of Choline Phospholipids via 2–Bromoethyl Dichlorophosphate", *Lipids,* 1982, 17(6), 453–459.

Hashimoto, "Synthesis and characterization of methotrexate–dimyristoylphosphatidylethanolamine derivatives and the glycerophosphorylethanolamine analogs", *Biochem. Biophys. Acta.,* 1985, 816, 163–168.

Hirt et al., "Zur Synthese der Phosphatide Eine neue Synthese der Lecithine", *Pharm. Acta. Helv.,* 1958, 33, 349–356 (Summary in English).

Lunbland, R.L., "The Chemical Cross–Linking of Peptide Chains", *Techniques in Protein Modification,* CRC Press, Inc., Ann Arbor, MI, Chapter 15, pp. 249–267, 1995.

Simons, "Degradation of SFV in BHJ21 Cells", *Biomembranes: Methods in Enzymology,* Part L—Membrane Biogenesis: Processing and Recycling, Sidney Fleischer and Becca Fleischer (eds.), 1983, 98, 263–264.

Santaella et al., "New Perfluoroalkylated Phospholipids as Injectable Surfactants: Synthesis, Preliminary Physicochemical and Biocompatibility Data", *New J. Chem.,* 1991, 15, 685–692.

Siegall, "Targeted Toxins as Anticancer Agents", *Cancer,* 1994, 74(3), 1006–1012.

Bally et al., "Polymorphism of phosphatidylethanolamine–phosphatidylserine model systems: influence of cholesterol and $Mg^{2+}$ on $Ca^{2+}$ triggered bilayer to hexagonal ($H\pi$) transitions", *Can. J. Biochem. Cell Biol,* 1983, 61, 346–352.

Blackwood et al., "Characterization of $Ca^{2+}$ –dependent phospholipid binding, vesicle aggregation and membrane fusion by annexins", *Biochem. J.,* 1990, 266, 195–200.

Brennan, "Liposome Houses Multiple Vesicles: Tethered vesicles encapsulated in lipid bilayer membrane hold promise of improved drug delivery", *C & En,* 1997, 9–10.

Coorssen et al., "Structural Effects of Neutral Lipids on Divalent Cation–Induced Interactions of Phosphatidylserine–Containing Bilayers", *Biophys. J.,* 1995, 68, 1009–1018.

Duzgunes et al., "Modulation of Membrane Fusion by Inotropic and Thermotropic Phase Transitions", *Biochem.,* 1984, 23, 3486–3494.

Holland t al., "Poly(ethylene glycol)–Lipid Conjugates Regulate the Calcium–Induced Fusion of Liposomes Composed o Phosphatidylethanolamine and Phosphatidylserine", *Biochem.,* 1996, 35, 2618–2624.

Kwon et al., "Effects of calcium ions on phospholipid aggregates at subzero temperatures", *Colloids and Surfaces B:Biointerfaces,* 1994, 3, 25–30.

Lansman et al., "Kinetics of A $Ca^{2+}$–Triggered Membrane Aggregation Reaction of Phospholipid Membranes", *Biochim. et Biophys. Acta,* 1975, 394, 335–347.

Lansman et al., "Charge Asymmetry Does not Affect the Rate of $Ca^{2+}$–Induced Aggregation of Phospholipid Vesicles", *Biophys. J.,* 1979, 26, 335–337.

Leckband et al., "Role of Calcium in the Adhesion and Fusion of Bilayers", *Biochem.,* 1993, 32, 1127–1140.

Leonards et al., "Roles of Lipids and Proteins in the $Ca^{2+}$ –$PO_4$–Induced Aggregation of Cytoskeleton–Free Erythrocyte Vesicle Membranes", *Biochem.,* 1984, 23, 2718–2725.

Ogihara et al., "Effects of Polyethylene Glycol (PEG), $Ca^{2+}$, and Temperature on Aggregation and Fusion of Phospholipid Liposomes", *Japanese J. Physiology,* 1989, vol. 39, No. 1, S15 (Abstract).

Portis et al., "Studies on the Mechanism of Membrane Fusion: Evidence for an Intermembrane $Ca^{2+}$–Phospholipid Complex, Synergism with $Mg^{2+}$, and Inhibition by Spectrin", *Biochem.,* 1979, 18(5), 780–790.

Silvius et al., "Lipid Phase Behavior and Calcium–Induced Fusion of Phosphatidylethanolamine–Phosphatidylserine Vesclies. Calorimetric and Fusion Studies", *Biochem.,* 1984, 23, 3232–3240.

Tilcock et al., "Cation–Dependent Segragation Phenomena and Phase Behavior in Model Membrane Systems Containing Phosphatidylserine: Influence of Cholesterol and Acyl Chain Composition", *Biochem.,* 1984, 23, 2696–2703.

Tilley et al., "Calcium– and Polyamine–Induced Aggregation of Phosphatidylserine– and Polyphosphoinositide–Containing Phospholipid Vesicles", *Biogenic Amines,* 1988, 5(1), 69–74.

Walker et al., "Encapsulation of bilayer vesicles by self–assembly", *Nature,* 1997, 387, 61–64.

Zalipsky, "Synthesis of an End–Group Functionalized Polytheylene Glycol–Lipid Conjugate for Preparation of Polymer–Grafted Liposomes", *Bioconj. Chem.,* 1993, 4, 296–299.

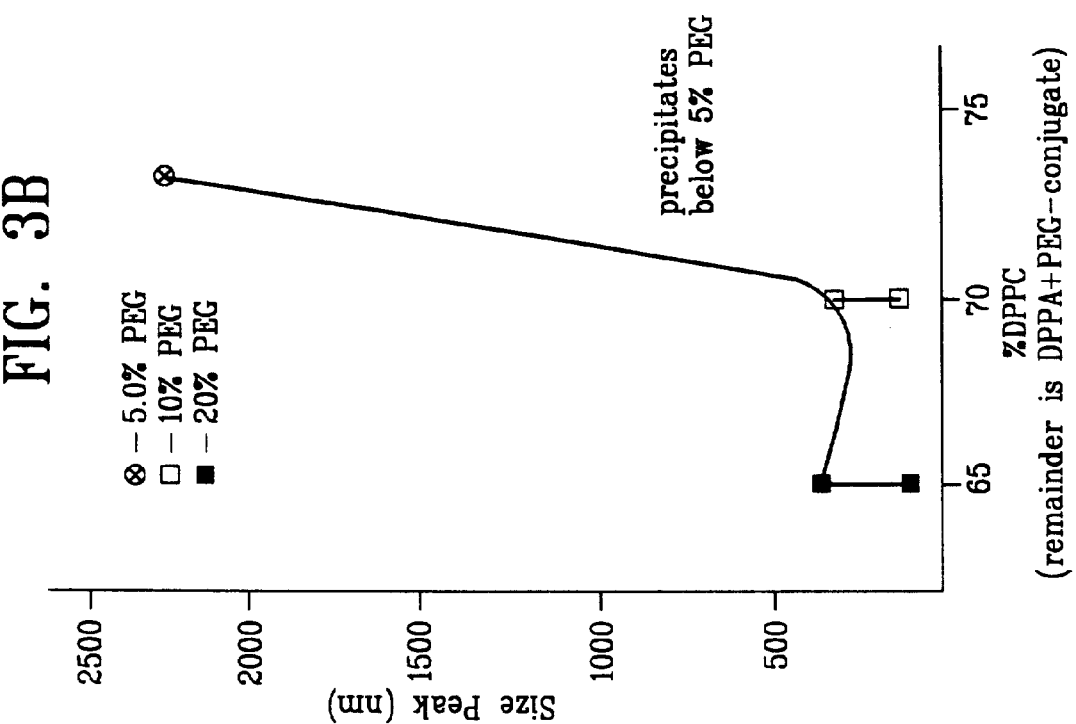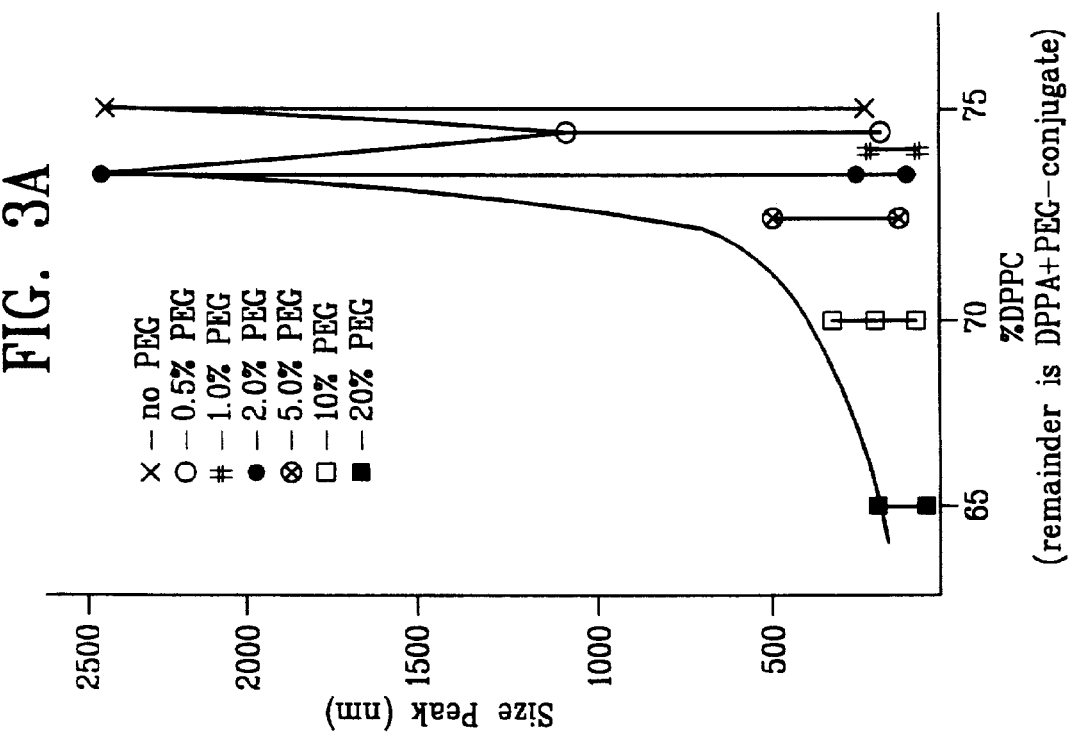

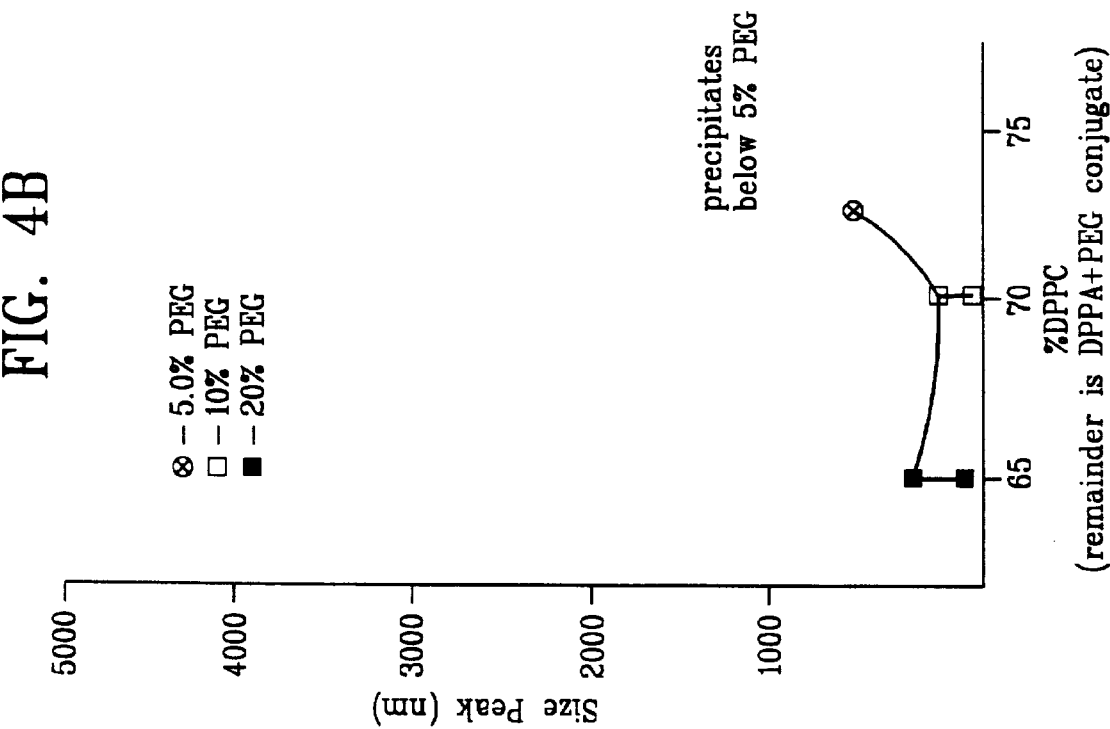
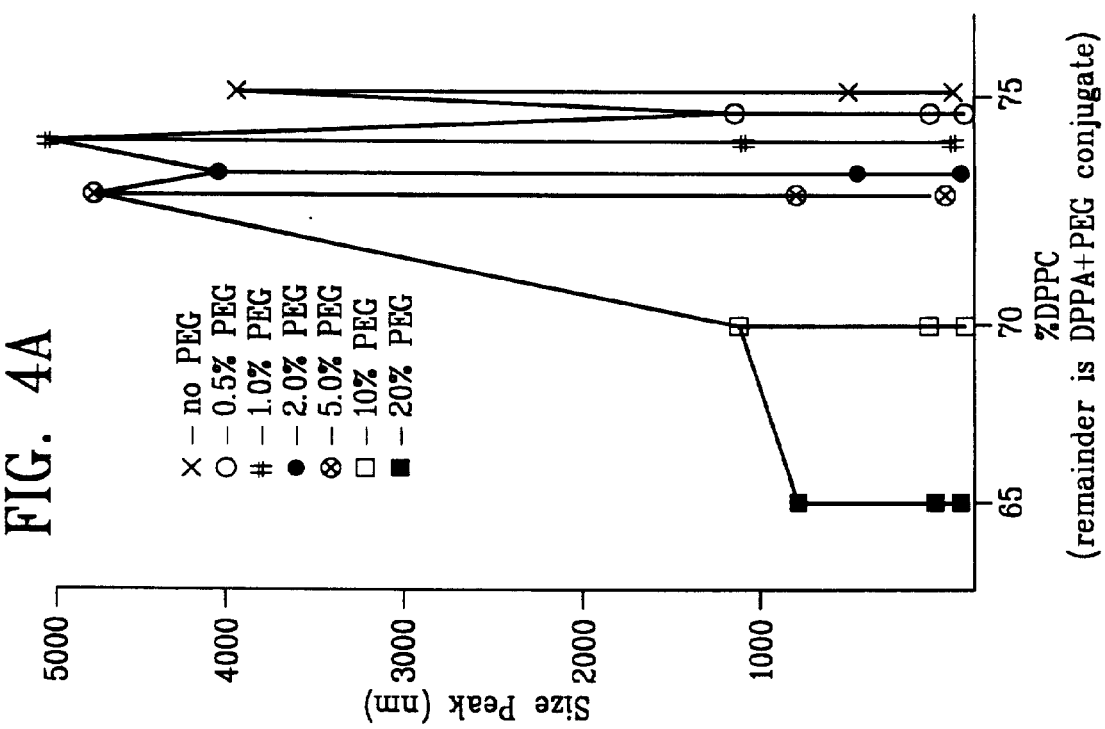

CHARGED LIPIDS AND USES FOR THE SAME

RELATED APPLICATIONS

This is a continuation-in-part of U.S. application Ser. No. 08/823,791, filed Mar. 21, 1997; a continuation-in-part of U.S. application Ser. No. 08/851,780 filed May 6, 1997; a continuation-in-part of U.S. application Ser. No. 08/877,826 filed Jun. 18, 1997; and a continuation-in-part of U.S. application Ser. No. 08/887,215 filed Jul. 2, 1997, the disclosures of each of which are hereby incorporated by reference hirein in their entirety.

FIELD OF THE INVENTION

The present invention is directed to charged lipids, compositions comprising charged lipids, and the use of these compositions in drug delivery, targeted drug delivery, therapeutic imaging and diagnostic imaging, as well as their use as contrast agents.

BACKGROUND OF THE INVENTION

To improve drug delivery, lessen toxicity and improve efficacy, various drug delivery systems have been devised. Drug delivery systems have included liposomes which are generally composed of neutral or zwitterionic lipids. The lipids in liposomes arrange themselves into bilayers and entrap one (unilamellar) or more (oligo- or multilamellar) spaces. The spaces between the bilayers of the lipids are usually filled with water. In conventional water filled liposomes, drugs are usually entrapped in the internal aqueous space, although in some cases they may be incorporated in the wall forming materials of the lipid bilayer. In conventional liposomes, it is often difficult to entrap a high concentration of a drug. Relying upon the internal entrapment of the drug, the efficiency necessarily depends upon the volume of fluid outside of the liposomes and circumscribed within the internal aqueous vesicular space. To improve the efficiency of drug entrapment, various techniques, such as ionic or pH gradients, have been employed. Still, the efficiency of drug encapsulation is less than desired. On long term storage, drugs entrapped within liposomes may leak out of the internal aqueous space into the surrounding milieu. The drug may therefore be lost from its desired intra-liposomal location. This is particularly problematic when there is a high concentration of drug entrapped within the liposomes and there is an osmotic gradient across the bilayer membrane. New and better methods of entrapping drugs in liposomes would be beneficial.

Studies have described the effects of calcium and other multivalent cations on membrane asymmetry, lipid distribution, vesicle size, aggregation and fusion. Although the underlying physical causes for the phenomena are debatable, general consensus exists that multivalent cations, such as calcium and magnesium, in the external environment of phospholipid vesicles cause the structures to aggregate into larger, multilamellar structures and promotes fusion. Barium and strontium ions have also been investigated in this regard. Duzgunes et al., *Biochemistry*, 23:3486–3494 (1984). Species of phospholipids that are particularly pronounced in these effects are the subjet of investigation, as described, for example, by Leckband, et al., *Biochemistry* 32:1127–1140 (1993), Tilley et al., *Biogenic Amines*, 5:69–74 (1988) and Kwon, et al., *Colloids and Surfaces B*, 3:25–30 (1994).

Other areas of investigation focused on the effect of calcium-induced aggregation on phase transition temperature and whether aggregation and fusion phenomena have a temperature dependance. Duzgunes, supra, Kwon, supra, and Tilcock et al., *Biochemistry*, 23:2696–2703 (1984). The effects of calcium-induced aggregation are so pronounced that efforts have been undertaken to limit the effect in order to control the size of liposomes used in drug delivery systems by forming vesicles in which calcium ions are confined to outer surfaces of the bilayer. European Patent Publication EP 579 703.

Another form of prior art has been the development of polymeric microspheres. Polymeric microspheres may retain the drugs to a better extent than liposomes, but there may be problems with biodegradability and toxicity.

The present invention is directed to, among other things, the development of new and improved drug and contrast media delivery systems that overcome the problems associated with the prior art.

SUMMARY OF THE INVENTION

The present invention describes methods of delivering bioactive agents to a patient and/or treating conditions in a patient comprising administering to the patient a composition comprising a charged lipid, a counter ion, a lipid covalently bonded to a polymer and a bioactive agent, and applying therapeutic ultrasound to the patient to facilitate delivery of the bioactive agent in a desired region of the patient. If desired, the methods may further comprise imaging the patient to monitor the location of the composition. The composition may further comprise, for example, one or more of neutral lipids, charged lipids, gases, gaseous precursors, liquids, oils, diagnostic agents, targeting ligands and/or other bioactive agents.

The present invention describes methods of delivering bioactive agents to a patient and/or treating conditions in a patient comprising administering to the patient a composition comprising a charged lipid, a counter ion, a lipid covalently bonded to a polymer, a bioactive agent and a targeting ligand. If desired, the methods may further comprise imaging the patient to monitor the location of the composition and/or applying therapeutic ultrasound to the patient to facilitate delivery of the bioactive agent in a desired region of the patient. The composition may further comprise, for example, one or more of neutral lipids, charged lipids, gases, gaseous precursors, liquids, oils, diagnostic agents and/or other bioactive agents.

The present invention also describes methods of providing an image of an internal region of a patient comprising administering to the patient a composition comprising a charged lipid, an counter ion, and a lipid covalently bonded to a polymer. The methods may further comprise scanning the patient using diagnostic imaging to obtain visible images of the internal region of the patient. The composition may further comprise, for example, one or more of neutral lipids, charged lipids, gases, gaseous precursors, liquids, oils, diagnostic agents, targeting ligands and/or bioactive agents.

The present invention also describes methods of diagnosing the presence of diseased tissue in a patient comprising administering to the patient a composition comprising a charged lipid, a counter ion, and a lipid covalently bonded to a polymer. The methods may further comprise scanning the patient using diagnostic imaging to obtain a visible image of any diseased tissue in the patient. The composition may further comprise, for example, one or more of neutral lipids, charged lipids, gases, gaseous precursors, liquids, oils, diagnostic agents, targeting ligands and/or bioactive agents.

In addition, the present invention describes novel contrast agents comprising a charged lipid, a counter ion, and a lipid covalently bonded to a polymer. The contrast agents may further comprise, for example, one or more of neutral lipids, charged lipids, gases, gaseous precursors, liquids, oils, diagnostic agents, targeting ligands and/or bioactive agents.

These and other aspects of the invention will become apparent from the following detailed description.

BRIEF DESCRIPTION OF THE FIGURES

FIG. 1A is an illutration of a composition of the present invention comprising a charged lipid, a counter ion and a lipid covalently bonded to a polymer, while FIG. 1B is an illustration of a composition of the present invention comprising a charged lipid, a counter ion, a lipid covalently bonded to a polymer and a targeting ligand.

FIGS. 3A and 3B are sizing profiles of compositions prepared with variable amounts of dipalmitoylphosphatidylcholine (DPPC), dipalmitoylphosphatidic acid (DPPA) and DPPE-PEG-5000 either in the absence of $CaCl_2$ (FIG. 3A) or with $CaCl_2$ added prior to liposome formation (FIG. 3B).

FIGS. 4A and 4B are sizing profiles of compositions prepared with variable amounts of DPPC, DPPA and DPPE-PEG-5000 either in the absence of $CaCl_2$ (FIG. 4A) or with $CaCl_2$ added prior to liposome formation (FIG. 4B). Unlike FIGS. 3A and 3B, FIGS. 4A and 4B have DPPA in excess of DPPC.

DETAILED DESCRIPTION OF THE INVENTION

Figures 1A, 1B:
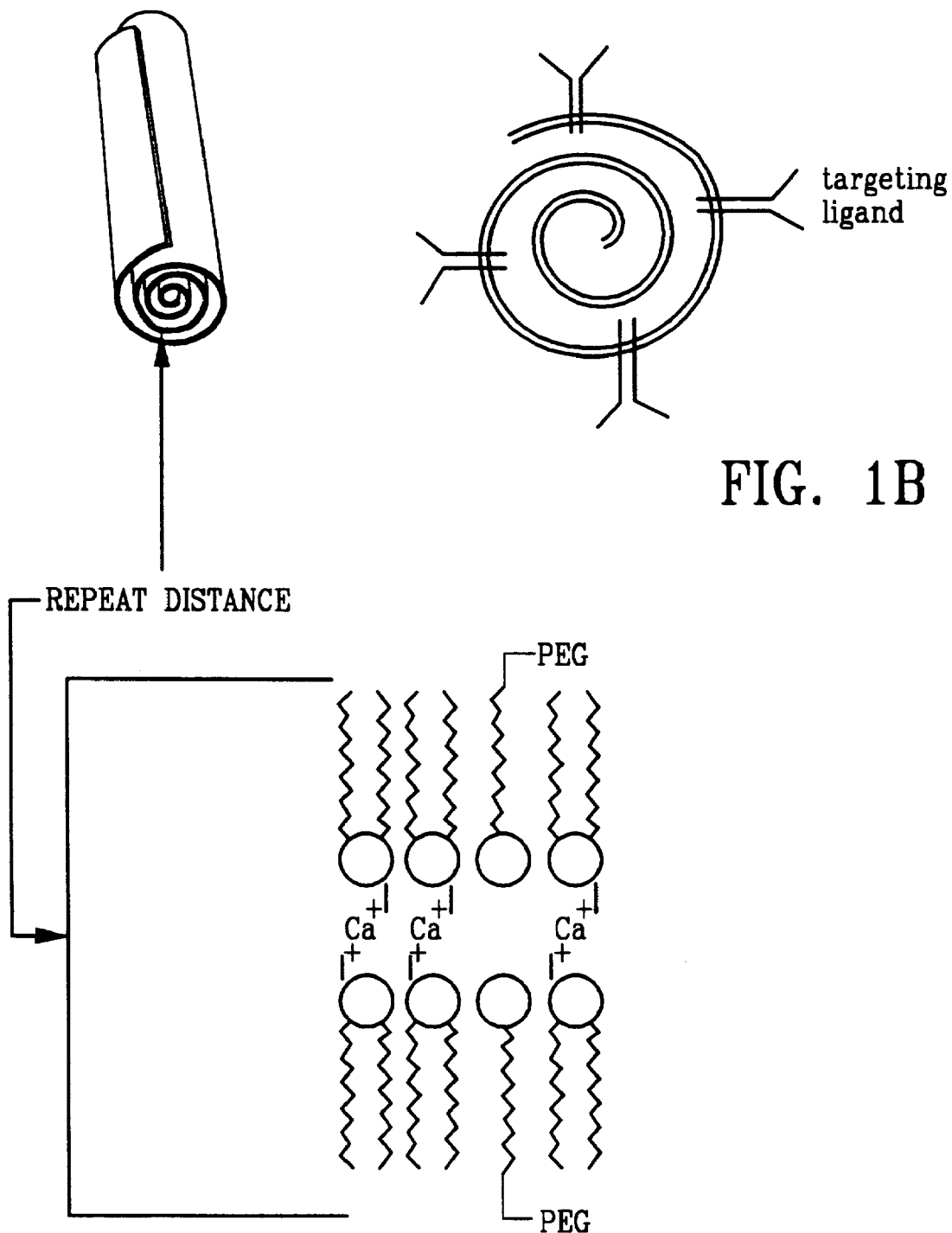
FIGS. 1A and 1B are illustrative examples of the compositions of the present invention.

As employed above and throughout the disclosure, the following terms, unless otherwise indicated, shall be understood to have the following meanings.

"Amphiphilic moiety" or "amphiphile" refers to a synthetic, semi-synthetic (modified natural) or naturally-occurring compound having a water-soluble, hydrophilic portion and a water-insoluble, hydrophobic portion. Preferred amphiphilic compounds are characterized by a polar head group, for example, a phosphatidylcholine group, and one or more nonpolar, aliphatic chains, for example, palmitoyl groups. "Fluorinated amphiphilic moiety" refers to an amphiphilic compound in which at least one hydrogen atom of the amphiphilic compound is replaced with a fluorine atom. In a preferred form, the fluorinated amphiphilic compounds are polyfluorinated. "Polyfluorinated amphiphilic moiety" refers to amphiphilic compounds which contain two or more fluorine atoms. "Perfluorinated amphiphilic moiety" refers to amphiphilic compounds in which all the hydrogen atoms have been replaced with a fluorine atom. "Amphipathy" refers to the simultaneous attraction and repulsion in a single molecule or ion containing one or more groups having an affinity for the phase or medium in which they are dissolved, emulsified and/or suspended, together with one or more groups that tend to be expelled from the involved phase or medium.

"Lipid" refers to a naturally-occurring, synthetic or semi-synthetic (modified natural) compound which is generally amphipathic. Lipids typically comp rise a hydrophilic component and a hydrophobic component. Exemplary lipids include, foir example, fatty acids, neutral fats, phosphatides, fluorinated lipids, oils, fluorinated oils, glycolipids, surface active agents (surfactants and fluorosurfactants), aliphatic alcohols, waxes, terpenes and steroids. The phrase semi-synthetic (modified natural) denotes a natural compound that has been chemically modified in some fashion. Lipids are also referred to herein as "stabilizing materials" or "stabilizing compounds." A "fluorinated lipid" refers to a lipid in which at least one hydrogen atom of the lipid is replaced with a fluorine atom.

"Surfactant" refers to a surface active agent, which is a compound that alters surface tension. Surface active agents include, for example, detergents, wetting agents and emulsifiers. "Fluorosurfactant" refers to a surfactant in which at least one hydrogen atom of the surfactant is replaced with a fluorine atom.

"Vesicle" refers to an entity which is generally characterized by the presence of one or more walls or membranes which form one or more internal voids. Vesicles may be formulated from a stabilizing material such as a lipid, including the various lipids described herein. The lipids may be natural, synthetic or semi-synthetic. The walls or membranes may be concentric or otherwise. The lipids may be in the form of one or more monolayers or bilayers. In the case of more than one monolayer or bilayer, the monolayers or bilayers may be concentric. Stabilizing compounds may be used to form a unilamellar vesicle (comprised of one monolayer or bilayer), an oligolamellar vesicle (comprised of about two or about three monolayers or bilayers) or a multilamellar vesicle (comprised of about three or more layers or comprised of about three or more monolayers or bilayers). The walls or membranes of vesicles may be substantially solid (uniform), or they may be porous or semi-porous. The vesicles described herein inchlde and may also be referred to as, for example, cochleates, liposomes, micelles, bubbles, microbubbles, microspheres, lipid-coated bubbles, nanospheres, microballoons, microcapsules, aerogels, clathrate bound vesicles, hexagonal H II phase structures, and the like. The internal void of the vesicles may optionally be filled with water, oil, liquids, gases, gaseous precursors, bioactive agents, diagnostic agents, and/or other materials.

"Liposome" refers to a generally spherical or spheroidal cluster or aggregate of amphipathic compounds, including lipid compounds, typically in the form of one or more concentric layers, for example, monolayers, bilayers or multi-layers. They may also be referred to herein as lipid vesicles. The liposomes may be formulated, for example, from ionic lipids and/or non-ionic lipids. Liposomes formulated from non-ionic lipids may be referred to as niosomes. Liposomes formulated, at least in part, from cationic lipids or anionic lipids may be referred to as cochleates.

"Cochleate" generally refers to a multilamellar lipid vesicle that is generally in the shape of a spiral or a tubule.

"Micelle" refers to colloidal entities formulated from lipids. Micelles may comprise a monolayer, bilayer, or hexagonal H II phase structure.

"Aerogel" refers to generally spherical or spheroidal entities which are characterized by a plurality of small internal voids. The aerogels may be formulated from synthetic materials (e.g., a foam prepared from baking resorcinol and formaldehyde) and/or natural materials, such as carbohydrates (polysaccharides) or proteins.

"Clathrate" refers to a solid, semi-porous or porous particle which may be associated with vesicles. Preferably, clathrates form a cage-like structure containing cavities which comprise one or more vesicles bound to the clathrate. A stabilizing material may be associated with the clathrate to promote the association of the vesicle with the clathrate. Clathrates may be formulated from, for example, porous apatites, such as calcium hydroxyapatite, and precipitates of polymers and metal ions, such as alginic acid precipitated with calcium salts.

"Emulsion" refers to a mixture of two or more generally immiscible liquids, and is generally in the form of a colloid. The mixture may be of lipids, for example, which may be homogeneously or heterogeneously dispersed throughout the emulsion. Alternatively, the lipids may be aggregated in the form of, for example, clusters, layers or tubules, including monolayers, bilayers or multi-layers.

"Suspension" or "dispersion" refers to a mixture, preferably finely divided, of two or more phases (solid, liquid or gas), such as, for example, liquid in liquid, solid in solid, gas in liquid, and the like which preferably can remain stable for extended periods of time.

"Hexagonal H II phase structure" generally refers to a tubular aggregation of lipids in liquid media, for example, aqueous media, in which the hydrophilic portion(s) of the lipids generally face inwardly in association with an aqueous liquid environment inside the tube. The hydrophobic portion(s) of the lipids generally radiate outwardly and the complex assumes the shape of a hexagonal tube. A plurality of tubes is generally packed together in the hexagonal phase structure.

"Gas filled vesicle" refers to a vesicle having a gas encapsulated therein. "Gaseous precursor filled vesicle" refers to a vesicle having a gaseous precursor encapsulated therein. The vesicles may be minimally, partially, substantially, or completely filled with the gas and/or gaseous precursor. The term "substantially" as used in reference to the gas and/or gaseous precursor filled vesicles means that greater than about 30% of the internal void of the substantially filled vesicles comprises a gas and/or gaseous precursor. In certain embodiments, greater than about 40% of the internal void of the substantially filled vesicles comprises a gas and/or gaseous precursor, with greater than about 50% being more preferred. More preferably, greater than about 60% of the internal void of the substantially filled vesicles comprises a gas and/or gaseous precursor, with greater than about 70% or 75% being more preferred. Even more preferably, greater than about 80% of the internal void of the substantially filled vesicles comprises a gas and/or gaseous precursor, with greater than about 85% or 90% being still more preferred. In particularly preferred embodiments, greater than about 95% of the internal void of the vesicles comprises a gas and/or gaseous precursor, with about 100% being especially preferred. Alternatively, the vesicles may contain no or substantially no gas or gaseous precursor.

"Patient" refers to animals, including mammals, preferably humans.

"Region of a patient" refers to a particular area or portion of the patient and in some instances to regions throughout the entire patient. Exemplary of such regions are the pulmonary region, the gastrointestinal region, the cardiovascular region (including, myocardial tissue), the renal region as well as other bodily regions, tissues, lymphocytes, receptors, organs and the like, including the vasculature and circulatory system, and as well as diseased tissue, including cancerous tissue. "Region of a patient" includes, for example, regions to be imaged with diagnostic imaging, regions to be treated with a bioactive agent, regions to be targeted for the delivery of a bioactive agent, and regions of elevated temperature. The "region of a patient" is preferably internal, although, if desired, it may be external. The phrase "vasculature" denotes blood vessels (including arteries, veins and the like). The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta.

"Bioactive agent" refers to a substance which may be used in connection with an application that is therapeutic or diagnostic, such as, for example, in methods for diagnosing the presence or absence of a disease in a patient and/or methods for the treatment of a disease in a patient. "Bioactive agent" refers to substances which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, proteins, peptides, vitamins, steroids, steroid analogs and genetic material, including nucleosides, nucleotides and polynucleotides.

"Diagnostic agent" refers to any agent which may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, radiofrequency (RF) and microwave laser. Diagnostic agents may also include any other agents useful in facilitating diagnosis of a disease or other condition in a patient, whether or not imaging methodology is employed. As defined herein, a "diagnostic agent" is a type of bioactive agent.

"Therapeutic agent," "pharmaceutical agent" or "drug" refers to any therapeutic or prophylactic agent which may be used in the treatment (including the prevention, diagnosis, alleviation, or cure) of a malady, affliction, condition, disease or injury in a patient. Therapeutically useful genetic materials, peptides, polypeptides and polynucleotides may be included within the meaning of the term pharmaceutical or drug. As defined herein, a "therapeutic agent," "pharmaceutical agent" or "drug" is a type of bioactive agent.

"Targeting ligand" refers to any material or substance which may promote targeting of tissues and/or receptors in vivo or in vitro with the compositions of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccbarides, carbohydrates, vitamins, steroids, steroid analogs, hormones, cofactors, and genetic material, including nucleosides, nucleotidies, nucleotide acid constructs and polynucleotides. A "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as orthopyridyl disulfide, vinylsulfone groups, azide groups, and α-iodo acetyl groups.

"Genetic material" refers to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination thereof The DNA and RNA may optionally comprise unnatural nucleotides and may be single or double stranded. "Genetic material" also refers to sense and anti-sense DNA and RNA, which are nucleotide sequences which are complementary to specific sequences of nucleotides in DNA and/or RNA.

"Stabilizing material" or "stabilizing compound" refers to any material which is capable of improving the stability of compositions containing the gases, gaseous precursors, bioactive agents, targeting ligands, and/or other materials described herein, including, for example, mixtures, suspensions, emulsions, dispersions, vesicles, and the like. Encompassed in the definition of "stabilizing material" are certain of the bioactive agents. The improved stability involves, for example, the maintenance of a relatively balanced condition, and may be exemplified, for example, by increased resistance of the composition against destruction, decomposition, degradation, and the like. In the case of embodiments involving vesicles filled with gases, gaseous precursors and/or bioactive agents, the stabilizing compounds may serve to either form the vesicles or stabilize the vesicles, in either way serving to minimize or substantially (including completely) prevent the escape of gases, gaseous precursors and/or bioactive agents from the vesicles until release is desired. The term "substantially," as used in the present context of preventing escape of gases, gaseous precursors and/or bioactive agents from the vesicles, means greater than about 50% is maintained entrapped in the vesicles until release is desired, and preferably greater than about 60%, more preferably greater than about 70%, even more preferably greater than about 80%, still even more preferably greater than about 90%, is maintained entrapped in the vesicles until release is desired. In particularly preferred embodiments, greater than about 95% of the gases, gaseous precursors, and/or bioactive agents are maintained entrapped until release is desired. The gases, gaseous precursors and/or bioactive agents may also be completely maintained entrapped (i.e., about 100% is maintained entrapped), until release is desired. The resulting mixture, suspension, emulsion or the like may comprise walls (i.e., films, membranes and the like) around the bioactive agent, gases and/or gaseous precursors, or may be substantially devoid of walls or membranes, if desired. The stabilizing may, if desired, form droplets. The stabilizing material may also comprise salts and/or sugars. In other embodiments, the stabilizing materials may be substantially (including completely) crosslinked. The stabilizing material may have a neutral, positive or negative charge.

"Vesicle stability" refers to the ability of vesicles to retain the gas, gaseous precursor and/or other bioactive agent entrapped therein after being exposed, for about one minute, to a pressure of about 100 millimeters (mm) of mercury (Hg). Vesicle stability is measured in percent (%), this being the fraction of the amount of gas which is originally entrapped in the vesicle and which is retained after release of the pressure. Vesicle stability also includes "vesicle resilience" which is the ability of a vesicle to return to its original size after release of the pressure.

"Droplet" refers to a spherical or spheroidal entity which may be substantially liquid or which may comprise liquid and solid, solid and gas, liquid and gas, or liquid, solid and gas. Solid materials within a droplet may be, for example, particles, polymers, lipids, proteins, or surfactants.

"Covalent association" refers to an intermolecular association or bond which involves the sharing of electrons in the bonding orbitals of two atoms.

"Noncovalent association" refers to intermolecular interaction among two or more separate molecules which does not involve a covalent bond. Intermolecular interaction is dependent upon a variety of factors, including, for example, the polarity of the involved molecules, and the charge (neutral, positive or negative) of the involved molecules. Noncovalent associations include, for example, ionic interactions, electrostatic interactions, dipole-dipole interactions, van der Waal's forces, hydrogen bonding and combinations thereof "Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the uncharged, partial positive end of a first polar molecule, commonly designated as $\delta^+$, to the uncharged, partial negative end of a second polar molecule, commonly designated as $\delta^-$. Dipole-dipole interactions are exemplified by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bond" refers to an attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

"Hydrophilic interaction" refers to molecules or portions of molecules which may substantially bind with, absorb and/or dissolve in water. This may result in swelling and/or the formation of reversible gels. "Hydrophobic interaction" refers to molecules or portions of molecules which do not substantially bind with, absorb and/or dissolve in water.

"Biocompatible" refers to materials which are generally not injurious to biological functions and which will not result in any degree of unacceptable toxicity, including allergenic responses and disease states.

"In combination with" refers to the incorporation of bioactive agents and/or targeting ligands in a stabilizing composition of the present invention, including, for example, emulsion, suspensions and vesicles. The bioactive agent and/or targeting ligand can be combined with the stabilizing compositions in any of a variety of ways. For example, the bioactive agent and/or targeting ligand may be associated covalently and/or non-covalently with the compounds or stabilizing materials. In the case of vesicles, the bioactive agent and/or targeting ligand may be entrapped within the internal void of the vesicle; may be integrated within the layer(s) or wall(s) of the vesicle, for example, by being interspersed among stabilizing materials which form or are contained within the vesicle layer(s) or wall(s); may be located on the surface of a vesicle or non-vesicular stabilizing material; and/or any combination thereof. Preferably, the targeting ligand is located on the surface of a vesicle or non-vesicular stabilizing material. In any case, the bioactive agent and/or targeting ligand may interact chemically with the walls of the vesicles, including, for example, the inner and/or outer surfaces of the vesicle and may remain substantially adhered thereto. Such interaction may take the form of, for example, noncovalent association or bonding, ionic interactions, electrostatic interactions, dipole—dipole interactions, hydrogen bonding, van der Waal's forces, covalent association or bonding, crosslinking or any other interaction, as will be apparent to one skilled in the art in view of the present disclosure. The interaction may result in the stabilization of the vesicle. The bioactive agent and/or targeting ligand may also interact with the inner or outer surface of the vesicle or the non-vesicular stabilizing material in a limited manner. Such limited interaction would permit migration of the bioactive agent and/or targeting ligand, for example, from the surface of a first vesicle to the surface of a second vesicle, or from the surface of a first non-vesicular stabilizing material to a second non-vesicular stabilizing material. Alternatively, such limited interaction may permit migration of the bioactive agent and/or targeting ligand, for example, from within the walls of a vesicle and/or non-vesicular stabilizing material to the surface of a vesicle and/or non-vesicular stabilizing material, and vice versa, or from inside a vesicle or non-vesicular stabilizing material to within the walls of a vesicle or non-vesicular stabilizing material and vice versa.

"Tissue" refers generally to specialized cells which may perform a particular function. The term "tissue" may refer to an individual cell or a plurality or aggregate of cells, for example, membranes or organs. The term "tissue" also includes reference to an abnormal cell or a plurality of abnormal cells. Exemplary tissues include pulmonary tissue, myocardial tissue, including myocardial cells and cardiomyocites, membranous tissues, including endothelium and epithelium, laminae, blood, connective tissue, including interstitial tissue, and tumors. "Cell" refers to any one of the minute protoplasmic masses which make up organized tissue, comprising a mass of protoplasm surrounded by a membrane, including nucleated and unnucleated cells and organelles. "Receptor" refers to a molecular structure within a cell or on the surface of a cell which is generally characterized by the selective binding of a specific substance. Exemplary receptors include cell-surface receptors for peptide hormones, neurotransmitters, antigens, complement fragments, immunoglobulins and cytoplasmic receptors.

The present invention describes compositions which comprise one or more charged lipids, counter ions and at least one lipid which is covalently bonded to a polymer. An illustrative example of one embodiment of the compositions of the present invention is presented in FIG. 1A. Preferably, the counter ion in the compositions is divalent in charge or greater. The compositions may optionally comprise one or more neutral lipids. Additionally, the compositions of the present invention preferably comprise a targeting ligand. An illustrative example of another embodiment of the compositions of the present invention comprising a targeting ligand is presented in FIG. 1B.

In the compositions of the present invention, the charged lipid may be present in an amount of from about 10 mole % to about 90 mole %, preferably from about 50 mole % to about 80 mole %, based on the total amount of lipid in the composition. The counter ion may be present in an amount necessary to balance the charge on the charged lipid. Accordingly, the amount of counter ion in the composition will depend upon the total net charge of the lipid molecule and upon the valency of the counter ion. Thus, as one skilled in the art would recognize, for every equivalent of charges on the charged lipid, about the same number of equivalents of counter ion should be used. For example, about 1 mole of phosphatidic acid may be used per about 1 mole of $Ca^{2+}$, while about 2 moles of stearic acid may be used per about 1 mole of $Ca^{2+}$.

The lipid covalently bonded to polymer may be used in an amount of from about 1 mole % to about 50 mole %, preferably from about 1 mole % to about 25 mole %, more preferably from about 5 mole % to about 25 mole %, based on the total amount of lipid in the composition. If desired, neutral lipids may be used in an amount up to about 10 mole % of the total amount of lipid in the composition.

Without intending to be bound by any theory of the invention, in the compositions of the present invention, the counter ions form salt bridges which crosslink the charged lipids to form aggregates or multilamellar vesicles. The aggregates or multilamellar vesicles may be referred to as cochleates, which may be in the form of a tubule or a spiral. The crosslinking of the counter ions may be noncovalent and may generally be considered an ionic or electrostatic interaction. The lipid covalently bonded to the polymer stabilizes the compositions so that they from well-defined vesicles. If the lipid covalently bonded to the polymer is not used in the compositions of the present invention, the counter ions cause the charged lipid species to form amorphous lipid clumps. In many cases, the lipid clumps may take the form of, for example, condensed lipid bilayers, but the lipid clumps do not form stable vesicles with size distributions suitable, for example, for intravenous injection.

Figure 2A:
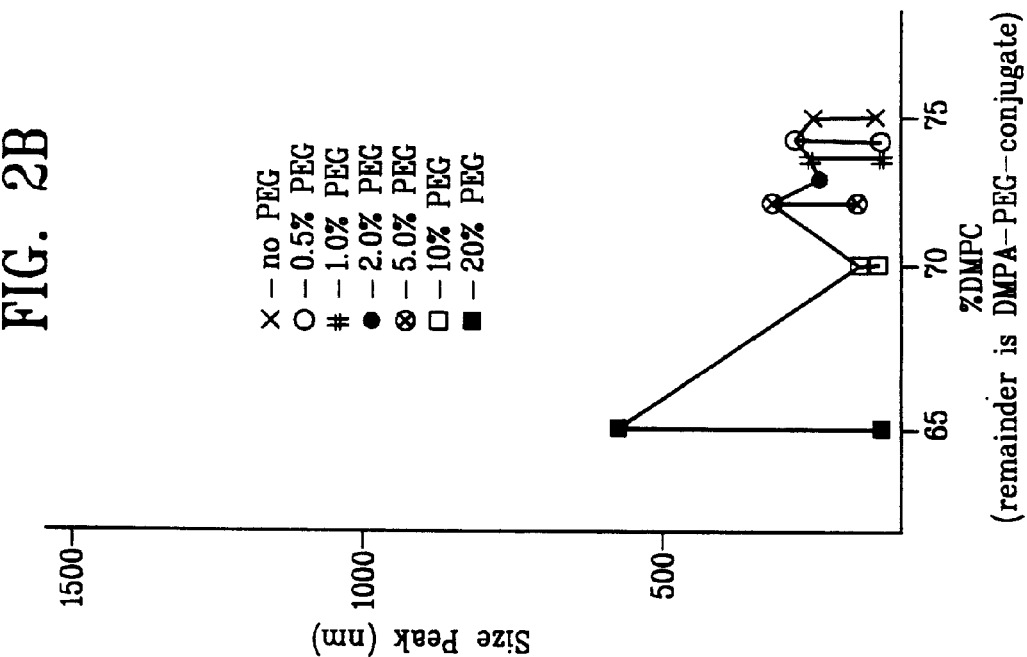
FIGS. 2A and 2B are sizing profiles of compositions prepared with variable amounts of dimyristoylphosphatidylcholine (DMPC), dimyristoylphosphatidic acid (DMPA) and dipalmitoylphosphatidylethanolamine-polyethylene glycol 5,000 (DPPE-PEG-5000) either in the absence of $CaCl_2$ (FIG. 2A) or with $CaCl_2$ added after liposome formation (FIG. 2B).
Figure 2B:
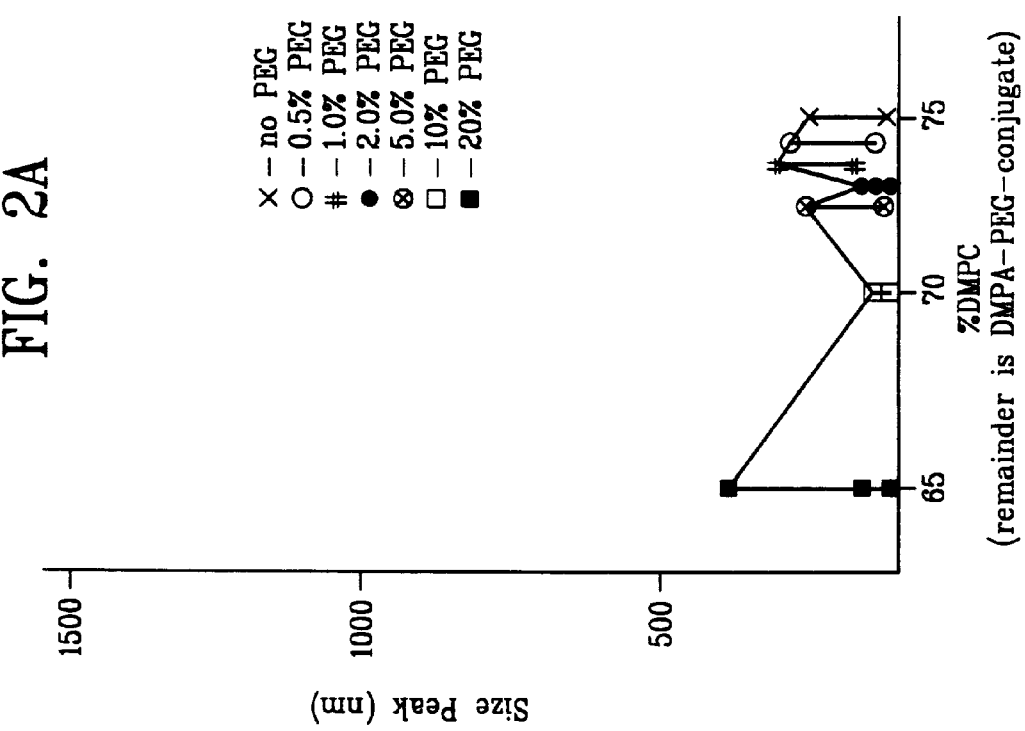

The lipid covalently bonded to a polymer (e.g., DPPE-PEG-5,000) causes compaction of the size of the composition in the presence of a counter ion, such as $Ca^{2+}$ (FIGS. 2B, 3B and 4B), when compared to the corresponding compositions that do not contain a counter ion (FIGS. 2A, 3A and 4A). The compaction effect caused by the lipid covalently bonded to the polymer is most notable when the counter ion is added at the initial incubation of the lipid mixture. Accordingly, in the methods described herein for preparing the compositions of the present invention, it is preferable to add the counter ion at the initial incubation of the lipid mixture. Increasing the amount of the lipid covalently bonded to a polymer allows the composition to stabilize at sizes generally under about 1.0 μm in the presence of a counter ion. When the lipid covalently bonded to the polymer is present in an amount less than about 5%, the composition is generally unstable and may precipitate. As shown in FIG. 2B, if a counter ion is added after initial incubation of the lipid mixture, there does not appear to be any statistical difference in size of the composition, with or without a counter ion, and with or without the lipid covalently bonded to a polymer.

In the compositions of the present invention, the charged lipid may be anionic (i.e., negatively charged, that is, carrying a net negative charge) or cationic (i.e., positively charged, that is, carrying a net positive charge). Preferred anionic lipids include phosphatidic acid, phosphatidyl glycerol and fatty acid esters thereof. Other anionic lipids include amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, palmitic acid, stearic acid, arachidonic acid, oleic acid, linolenic acid, linoleic acid, myristic acid, sulfolipids and sulfatides, free fatty acids, both saturated and unsaturated, and negatively charged derivatives thereof. More preferably, the anionic lipid is a phosphatidic acid, a phosphatidyl glycerol, a phosphatidyl glyercol fatty acid ester, a phosphatidyl ethanolamine anandamide, a phosphatidyl ethanolamine methanandamide, a phosphatidyl serine, a phosphatidyl inositol, a phosphatidyl inositol fatty acid ester, a cardiolipin, a phosphatidyl ethylene glycol, an acidic lysolipid, a sulfolipid, a sulfatide, a saturated free fatty acid, an unsaturated free fatty acid, a palmitic acid, a stearic acid, an arachidonic acid, an oleic acid, a linolenic acid, a linoleic acid or a myristic acid. In a preferred embodiment, the anionic lipid in the composition of the present invention is a fluorinated anionic lipid. Any of the anionic lipids described herein may be fluorinated by replacing at least one hydrogen atom with a fluorine atom. One skilled in the art will recognize that countless other natural and synthetic variants carrying negative charged moieties will also function in the invention.

For the anionic lipids, the chain length of the fatty acyl moiety can vary from about 8 to about 26 carbon atoms in length. The lipids may be saturated, monounsaturated or polyunsaturated. Preferably, the lipid chain length ranges from about 10 to about 24 carbon atoms, more preferably about 16 carbon atoms. A wide variety of anionic lipids may be used but particularly preferred are dipalmitoylphosphatidic acid (DPPA) and dipalmitoylphosphatidyl glycerol. The carbon chain lengths of the various lipids in the compositions of the present invention (e.g., charged lipid, lipid covalently boned to polymer, neutral lipid) may be the same or different. Preferably, the chain length of the different lipids in the composition is similar. In a preferred embodiment, the anionic lipid in the composition of the present invention is a fluorinated anionic lipid. Any of the anionic lipids described herein may be fluorinated by replacing at least one hydrogen atom with a fluorine atom.

When the charged lipid is anionic, a cationic counter ion is used to form the compositions. Suitable cationic counter ions include, for example, alkaline earths, beryllium ($Be^{+2}$), magnesium ($Mg^{+2}$), calcium ($Ca^{+2}$), strontium ($Sr^{+2}$) and barium ($Ba^{+2}$); amphoteric ions: aluminum ($Al^{+3}$), gallium ($Ga^{+3}$), germanium ($Ge^{+3}$), tin ($Sn^{+4}$) and lead ($Pb^{+2}$ and $Pb^{+4}$); transition metals: titanium ($Ti^{+3}$ and $Ti^{+4}$), vanadium ($V^{+2}$ and $V^{+3}$), chromium ($Cr^{+2}$ and $Cr^{+3}$), manganese ($Mn^{+2}$ and $Mn^{+3}$), iron ($Fe^{+2}$ and $Fe^{+3}$), cobalt ($Co^{+2}$ and $Co^{+3}$), nickel ($Ni^{+2}$ and $Ni^{+3}$), copper ($Cu^{+2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W^{+4}$), osmium ($Os^{+2}$, $Os^{+3}$ and $Os^{+4}$), iridium ($Ir^{+2}$, $Ir^{+3}$ and $Ir^{+4}$), mercury ($Hg^{+2}$) and bismuth ($Bi^{+3}$); and rare earth lanthanides, exemplified by lanthanum ($La^{+3}$) and gadolinium ($Gd^{+3}$). Some of these ions, notably lead and nickel, may be inappropriate for in vivo use due to toxicity. Preferred cations are calcium ($Ca^{+2}$), magnesium ($Mg^{+2}$) and zinc ($Zn^{+2}$) and paramagnetic cations such as manganese (preferably $Mn^{+2}$) and gadolinium ($Gd^{+3}$). Most preferably the cation is calcium ($Ca^{+2}$).

When the charged lipids of the invention carry a net positive charge at pH 7, the lipid is a cationic lipid. Cationic lipids which may be used in the compositions of the present invention include, for example, phosphatidylethanolamine, phospatidylcholine, glycero-3-ethylphosphatidylcholine and fatty acyl esters thereof, di- and trimethyl ammonium propane, di- and tri-ethylammonium propane and fatty acyl esters thereof. A preferred derivative from this group is N-[1-(2,3-dioleoyloxy)propyl]-N,N,N-trimethyl-ammonium chloride ("DOTMA"). Additionally, a wide array of synthetic cationic lipids can function in the present invention. These include common natural lipids derivatized to contain one or more basic functional groups. Examples of lipids which can be so modified include, for example, dimethyldioctadecylammonium bromide, sphingolipids, sphingo-myelin, lysolipids, glycolipids such as ganglioside GM1, sulfatides, glycosphingolipids, cholesterol and cholesterol esters and salts, N-succinyldioleoyl-phosphatidylethanolamine, 1,2,-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoylhomocystiene. In a preferred embodiment, the cationic lipid in the composition of the present invention is a fluorinated cationic lipid. Any of the cationic lipids described herein may be fluorinated by replacing at least one hydrogen atom with a fluorine atom Specially synthesized cationic lipids also function in the present invention, including those compounds of formula (I), formula (II) and formula (III), described in U.S. patent application Ser. No. 08/391,938, filed Feb. 21, 1995, the disclosure of which is hereby incorporated by reference herein in its entirety.

The cationic lipid may be a compound of formula (I):

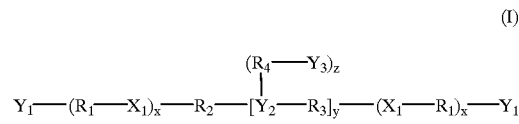

(I)

where each of x, y and z is independently an integer from 0 to about 100; each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—; each $X_2$ is independently O or S; each $Y_1$ is independently a phosphate residue, N($R_6$)$_a$—, S($R_6$)$_a$—, P($R_6$)$_a$— or —$CO_2R_6$, wherein a is an integer from 1 to 3; each $Y_2$ is independently —N($R_6$)$_b$—, —S($R_6$)$_b$— or —P($R_6$)$_b$—, wherein b is an integer from 0 to 2; each $Y_3$ is independently a phosphate residue, N($R_6$)$_a$—, S($R_6$)$_a$—, P($R_6$)$_a$— or —$CO_2R_6$, wherein a is an integer from 1 to 3; each of $R_1$, $R_2$, $R_3$ and $R_4$ is independently alkylene of 1 to about 20 carbons; each $R_5$ is independently hydrogen or alkyl of 1 to about 10 carbons; and each $R_6$ is independently —[$R_7$—$X_3$]$_c$—$R_8$ or —$R_9$—[$X_4$—$R_{10}$]$_d$—Q, wherein: each of c and d is independently an integer from 0 to about 100; each Q is independently a phosphate residue, —N($R_{11}$)$_q$, —S($R_{11}$)$_q$, —P($R_{11}$)$_q$ or —$CO_2R_6$, wherein q is an integer from 1 to 3; each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—; each $R_7$ is independently alkylene of 1 to about 20 carbons; each $R_8$ is independently hydrogen or alkyl of 1 to about 60 carbons; each of $R_9$ and $R_{10}$ is independently alkylene of 1 to about 20 carbons; and each $R_{11}$ is independently -[$R_7$—$X_3$]$_c$—$R_8$ or —$R_9$—[$X_4$—$R_{10}$]$_d$—W, wherein: each W is independently a phosphate residue, —N($R_{12}$)$_w$, —S($R_{12}$)$_w$, —P($R_{12}$)$_w$ or —$CO_2R_6$, wherein w is an integer from 1 to 3; and $R_{12}$ is —[$R_7$—$X_3$]$_c$—$R_8$, with the proviso that the compound of formula (I) comprises at least one, and preferably at least two, quaternary salts.

In the above formula (I), each of x, y and z is independently an integer from 0 to about 100. Preferably, each of x, y and z is independently an integer of from 0 to about 50, with integers from 0 to about 20 being more preferred. Even more preferably, each of x, y and z is independently an integer from 0 to about 10, with integers from 0 to about 5 being still more preferred. In certain particularly preferred embodiments, x is 1, y is 2 or 3 and z is 0 or 1.

In the above formula (I), each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—. Preferably, each $X_1$ is independently —C(=O)—$NR_5$—, —$NR_5$—C(=O)—, —C(=O)—O— or —O—C(=O)—.

Each $X_2$ in the definitions of $X_1$, $X_3$ and $X_4$ above is independently O or S. Preferably, $X_2$ is O.

In the above formula (I), each $Y_1$ is independently a phosphate residue, N($R_6$)$_a$—, S($R_6$)$_a$—, P($R_6$)$_a$— or —$CO_2R_6$, wherein a is an integer from 1 to 3. Preferably, each $Y_1$ is independently a phosphate residue, N($R_6$)$_a$— or —$CO_2R_6$, wherein a is 2 or 3. Preferably, a is 3.

Each $Y_2$ in formula (I) above is independently -N($R_6$)$_b$—, —S($R_6$)$_b$— or —P($R_6$)$_b$—, wherein b is an integer from 0 to 2. Preferably, $Y_2$ is —N($R_6$)$_b$—, wherein b is 1 or 2.

In the above formula (I), each $Y_3$ is independently a phosphate residue, N($R_6$)$_a$—, S($R_6$)$_a$—, P($R_6$)$_a$— or —$CO_2R_6$, wherein a is an integer from 1 to 3. Preferably, each $Y_3$ is independently a phosphate residue, N($R_6$)$_a$— or —$CO_2R_6$, where a is 2 or 3, preferably a is 3.

In the above formula (I), each of $R_1$, $R_2$, $R_3$ and $R_4$ is independently alkylene of 1 to about 20 carbons. Preferably, each of $R_1$, $R_2$, $R_3$ and $R_4$ is independently straight chain alkylene of 1 to about 10 carbons or cycloalkylene of about 4 to about 10 carbons. More preferably, each of $R_1$, $R_2$, $R_3$ and $R_4$ is independently straight chain alkylene of 1 to about 4 carbons or cycloalkylene of about 5 to about 7 carbons. Even more preferably, each of $R_1$, $R_2$, $R_3$ and $R_4$ is independently methylene, ethylene or cyclohexylene.

In the above definitions of $X_1$, $X_3$ and $X_4$, each $R_5$ is independently hydrogen or alkyl of 1 to about 10 carbons. Preferably, each $R_5$ is independently hydrogen or alkyl of 1 to about 4 carbons. More preferably, $R_5$ is hydrogen.

In the above definitions of $Y_1$, $Y_2$ and $Y_3$, each $R_6$ is independently —[$R_7$—$X_3$]$_c$—$R_8$ or —$R_9$—[$X_4$—$R_{10}$]$_d$—Q, wherein each of c and d is independently an integer from 0 to about 100. Preferably, each of c and d is independently an integer from 0 to about 50, with integers from 0 to about 20 being more preferred. Even more preferably, each of c and d is independently an integer from 0 to about 10, with integers from 0 to about 5 being still more preferred. In certain particularly preferred embodiments, c is 0 or 1 and d is 1.

Each Q in $R_6$ above is independently a phosphate residue, —N($R_{11}$)$_q$, —S($R_{11}$)$_q$, —P($R_{11}$)$_q$ or —$CO_2R_{11}$, wherein q is an integer from 1 to 3. Preferably, each Q is independently a phosphate residue, —N($R_{11}$)$_q$ or —$CO_2R_{11}$, where q is 2 or 3 preferably 3.

Also in the above definition of $R_6$, each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—, wherein each of $X_2$ and $R_5$ is independently as previously described. Preferably, each of $X_3$ and $X_4$ is independently —C(=O)—$NR_5$—, —$NR_5$—C(=O)—, —C(=O)—O— or —O—C(=O)—.

In the definitions of $R_6$, $R_{11}$ and $R_{12}$ above, each $R_7$ is independently alkylene of 1 to about 20 carbons. Preferably, each $R_7$ is independently alkylene of 1 to about 10 carbons, with alkylene of 1 to about 4 carbons being preferred. More preferably, each $R_7$ is independently methylene or ethylene.

Also in the definitions of $R_6$, $R_{11}$ and $R_{12}$ above, each $R_8$ is independently hydrogen or alkyl of 1 to about 60 carbons. Preferably, each $R_8$ is independently hydrogen or alkyl of 1 to about 40 carbons, with hydrogen or alkyl of 1 to about 20 carbons being more preferred. Even more preferred, each $R_8$ is independently hydrogen or alkyl of 1 to about 16 carbons. In certain particularly preferred embodiments, each $R_8$ is independently hydrogen, methyl, dodecyl or hexadecyl.

Each of $R_9$ and $R_{10}$ in the definitions of $R_6$ and $R_{11}$ above is independently alkylene of 1 to about 20 carbons. Preferably, each of $R_9$ and $R_{10}$ is independently alkylene of 1 to about 10 carbons. More preferably, each of $R_9$ and $R_{10}$ is independently alkylene of 1 to about 4 carbons. Even more preferably, each of $R_9$ and $R_{10}$ is independently methylene or ethylene.

Each $R_{11}$ in Q above is independently —[$R_7$—$X_3$]$_c$—$R_8$ or —$R_9$—[$X_4$—$R_{10}$]$_d$—W, wherein each of c, d, $X_3$, $X_4$, $R_7$, $R_8$, $R_9$ and $R_{10}$ is independently as previously described.

Each W in $R_{11}$ above is independently a phosphate residue, —N($R_{12}$)$_w$, —S($R_{12}$)$_w$, —P($R_{12}$)$_w$ or —$CO_2R_{12}$, wherein w is an integer from 1 to 3. Preferably, W is a phosphate residue, —N($R_{12}$)$_w$ or —$CO_2R_{12}$, wherein w is 2 or 3. Preferably, w is 3.

In the above definition of W, $R_{12}$ is —[$R_7$—$X_3$]$_c$—$R_8$, wherein each of c, $X_3$, $R_7$ and $R_8$ is independently as previously described.

Another cationic lipid compound is a compound of the formula (II):

$$Y_1—R_1—Y_1 \qquad (II)$$

where each $Y_1$ is independently a phosphate residue, N($R_2$)$_a$—, S($R_2$)$_a$—, P($R_2$)$_a$— or —$CO_2R_2$, wherein a is an integer from 1 to 3; $R_1$ is alkylene of 1 to about 60 carbons containing 0 to about 30 —O—, —S—, —$NR_3$— or —$X_2$—($R_3X_2$)P(=$X_2$)—$X_2$— heteroatoms or heteroatom groups; $R_2$ a residue of the formula —$R_4$—[($X_1$—$R_5$)$_x$—$Y_2$]$_y$—$R_6$, wherein each of x and y is independently an integer from 0 to about 100; each $X_1$ is independently a direct bond, —O—, —S—, —$NR_3$—, —C(=$X_2$)—, —C(=$X_2$)—N($R_3$)—, —N($R_3$)—C(=$X_2$)—, —C(=$X_2$)—O—, —O—C(=$X_2$)— or —$X_2$—($R_3X_2$)P(=$X_2$)—$X_2$—; each $X_2$ is independently O or S; each $Y_2$ is independently —S($R_2$)$_b$—, —N($R_2$)$_b$— or —P($R_2$)$_b$—, wherein b is an integer from 0 to 2; each $R_3$ is independently hydrogen or alkyl of 1 to about 10 carbons; each of $R_4$ and $R_5$ is independently a direct bond or alkylene of 1 to about 30 carbons containing 0 to about 15 —O—, —S—, —$NR_3$— or —$X_2$—($R_3X_2$)P(=$X_2$)—$X_2$— heteroatoms or heteroatom groups; and each $R_6$ is independently hydrogen or alkyl of 1 to about 60 carbons containing 0 to about 30 —O—, —S—, —$NR_3$— or —$X_2$—($R_3X_2$)P(=$X_2$)—$X_2$— heteroatoms or heteroatom groups; with the proviso that the compound of formula (II) comprises at least one, and preferably at least two, quaternary salts.

In the above formula (II), each $Y_1$ is independently a phosphate residue, $N(R_2)_a$—, $S(R_2)_a$—, $P(R_2)_a$— or —$CO_2R_2$, wherein a is an integer from 1 to 3. Preferably, each $Y_1$ is independently a phosphate residue, —$N(R_2)_a$— or —$CO_2R_2$, wherein a is 2 or 3. Preferably, a is 3.

Also in the above formula (II), $R_1$ is alkylene of 1 to about 60 carbons containing 0 to about 30 —O—, —S—, —$NR_3$— or —$X_2$—$(R_3X_2)P(=X_2)$—$X_2$— heteroatoms or heteroatom groups. Preferably, $R_1$ is alkylene of 1 to about 40 carbons, with alkylene of 1 to about 20 carbons being preferred. More preferably, $R_1$ is straight chain alkylene of 1 to about 10 carbons or cycloalkylene of about 4 to about 10 carbons. Even more preferably, $R_1$ is straight chain alkylene of 1 to about 4 carbons or cycloalkylene of about 5 to about 7 carbons.

In the above definition of $Y_1$, $R_2$ is a residue of the formula —$R_4$—$[(X_1$—$R_5)_x$—$Y_2]_y$—$R_6$, wherein each of x and y is independently an integer from 0 to about 100. Preferably, each of x and y is independently an integer from 0 to about 50, with integers from 0 to about 20 being more preferred. Even more preferably, each of x and y is independently an integer from 0 to about 10.

In the above definition of $R_2$, each $X_1$ is independently a direct bond, —O—, —S—, —$NR_3$—, —$C(=X_2)$—, —$C(=X_2)$—$N(R_3)$—, —$N(R_3)$—$C(=X_2)$—, —$C(=X_2)$—O—, —O—$C(=X_2)$— or —$X_2$—$(R_3X_2)P(=X_2)$—$X_2$—. Preferably, $X_1$ is a direct bond, —$C(=X_2)$—$N(R_3)$—, —$N(R_3)$—$C(=X_2)$—, —$C(=X_2)$—O— or —O—$C(=X_2)$—.

Each $X_2$ in the above definitions of $X_1$, $R_1$, $R_4$, $R_5$ and $R_6$ is independently O or S. Preferably, $X_2$ is O.

Each $Y_2$ in the above definition of $R_2$ is independently —$S(R_2)_b$—, —$N(R_2)_b$— or —$P(R_2)_b$—, wherein b is an integer of from 0 to 2. Preferably, $Y_2$ is —$N(R_2)_b$— and b is 1 or 2.

In the above definitions of $X_1$, $R_1$, $R_4$, $R_5$ and $R_6$, each $R_3$ is independently hydrogen or alkyl of 1 to about 10 carbons. Preferably, each $R_3$ is independently hydrogen or alkyl of 1 to about 4 carbons. More preferably, $R_3$ is hydrogen.

In the above definition of $R_2$, each of $R_4$ and $R_5$ is independently a direct bond or alkylene of 1 to about 30 carbons containing 0 to about 15 —O—, —S—, —$NR_3$— or —$X_2$—$(R_3X_2)P(=X_2)$—$X_2$— heteroatoms or heteroatom groups. Preferably, each of $R_4$ and $R_5$ is independently a direct bond or alkylene of 1 to about 20 carbons. More preferably, each of $R_4$ and $R_5$ is independently a direct bond, straight chain alkylene of 1 to about 10 carbons or cycloalkylene of 4 to about 10 carbons. Even more preferably, each of $R_4$ and $R_5$ is independently a direct bond, straight chain alkylene of 1 to about 4 carbons or cycloalkylene of about 5 to about 7 carbons.

Each $R_6$ in $R_2$ above is independently hydrogen or alkyl of 1 to about 60 carbons containing 0 to about 30 —O—, —S—, —$NR_3$— or —$X_2$—$(R_3X_2)P(=X_2)$—$X_2$— heteroatoms or heteroatom groups. Preferably, each $R_6$ is independently hydrogen or alkyl of 1 to about 40 carbons. More preferably, each $R_6$ is independently hydrogen or alkyl of 1 to about 20 carbons.

The cationic lipid may also be a compound of the formula (III):

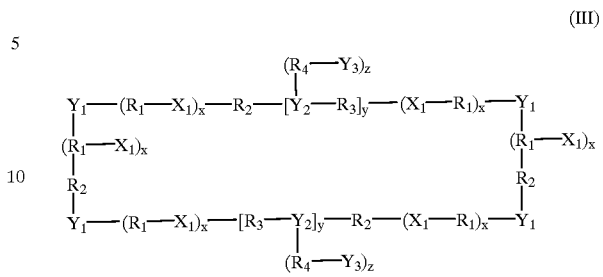

(III)

where each of x, y and z is independently an integer from 0 to about 100; each $X_1$ is independently —O—, —S—, —$NR_5$—, —$C(=X_2)$—, —$C(=X_2)$—$N(R_5)$—, —$N(R_5)$—$C(=X_2)$—, —$C(=X_2)$—O—, —O—$C(=X_2)$— or —$X_2$—$(R_5X_2)P(=X_2)$—$X_2$—; each $X_2$ is independently O or S; each $Y_1$ independently —O—, —$N(R_6)_a$—, —$S(R_6)_a$— or —$P(R_6)_a$—, wherein a is an integer from 0 to 2; each $Y_2$ is independently —$N(R_6)_a$—, —$S(R_6)_a$— or —$P(R_6)_a$—, wherein a is an integer from 0 to 2; each $Y_3$ is independently a phosphate residue, $N(R_6)_b$—, $S(R_6)_b$—, $P(R_6)_b$— or —$CO_2R_6$, wherein b is an integer from 1 to 3; each of $R_1$, $R_2$, $R_3$ and $R_4$ is independently alkylene of 1 to about 20 carbons; each $R_5$ is independently hydrogen or alkyl of 1 to about 10 carbons; and each $R_6$ is independently —$[R_7$—$X_3]_c$—$R_8$ or —$R_9$—$[X_4$—$R_{10}]_d$—Q, where each of c and d is independently an integer from 0 to about 100; each Q is independently a phosphate residue, —$N(R_{11})_q$, —$S(R_{11})_q$, —$P(R_{11})_q$ or —$CO_2R_{11}$, wherein q is an integer from 1 to 3; each of $X_3$ and $X_4$ is independently —O—, —S—, —$NR_5$—, —$C(=X_2)$—, —$C(=X_2)$—$N(R_5)$—, —$N(R_5)$—$C(=X_2)$—, —$C(=X_2)$—O—, —O—$C(=X_2)$— or —$X_2$—$(R_5X_2)P(=X_2)$—$X_2$—; each $R_7$ is independently alkylene of 1 to about 20 carbons; each $R_8$ is independently hydrogen or alkyl of 1 to about 60 carbons; each of $R_9$ and $R_{10}$ is independently alkylene of 1 to about 20 carbons; and each $R_{11}$ is independently —$[R_7$—$X_3]_c$—$R_8$ or —$R_9$—$[X_4$—$R_{10}]_d$—W, where each W is independently a phosphate residue, —$N(R_{12})_w$, —$S(R_{12})_w$, —$P(R_{12})_w$ or —$CO_2R_{12}$, wherein w is an integer from 1 to 3; and $R_{12}$ is —$[R_7$—$X_3]_c$—$R_8$; with the proviso that the compound of formula (III) comprises at least one, and preferably at least two, quaternary salts.

In the above formula (III), each of x, y and z is independently an integer from 0 to about 100. Preferably, each of x, y and z is independently an integer from 0 to about 50, with integers from 0 to about 20 being more preferred. Even more preferably, each of x, y and z is independently an integer from 0 to about 10. Still more preferably, each of x, y and z is independently an integer from 0 to about 5. In certain particularly preferred embodiments, x is 1, y is 2 or 3 and z is 0 or 1.

In the above formula (III), each $X_1$ is independently —O—, —S—, —$NR_5$—, —$C(=X_2)$—, —$C(=X_2)$—$N(R_5)$—, —$N(R_5)$—$C(=X_2)$—, —$C(=X_2)$—O—, —O—$C(=X_2)$— or —$X_2$—$(R_5X_2)P(=X_2)$—$X_2$—. Preferably, each $X_1$ is independently —$C(=O)$—$NR_5$—, —$NR_5$—$C(=O)$—, —$C(=O)$—O— or —O—$C(=O)$—.

In the above definitions of $X_1$, $X_3$ and $X_4$, each $X_2$ is independently O or S. Preferably, $X_2$ is O.

Each $Y_1$ in formula (III) above is independently —O—, —$N(R_6)_a$—, —$S(R_6)_a$— or —$P(R_6)_a$—, wherein a is an integer from 0 to 2. Preferably, $Y_1$ is —$N(R_6)_a$—, where a is 1 or 2.

Each $Y_2$ in formula (III) above is independently —$N(R_6)_a$—, —$S(R_6)_a$— or —$P(R_6)_a$—, wherein a is an integer from 0 to 2. Preferably, $Y_2$ is —$N(R_6)_a$—.

In the above formula (III), each $Y_3$ is independently a phosphate residue, $N(R_6)_b$—, $S(R_6)_b$—, $P(R_6)_b$— or —$CO_2R_6$, wherein b is an integer from 1 to 3. Preferably, each $Y_3$ is independently a phosphate residue or $N(R_6)_b$—, wherein b is 2 or 3. Preferably, b is 3.

In the above formula (III), each of $R_1$, $R_2$, $R_3$ and $R_4$ is independently alkylene of 1 to about 20 carbons. Preferably, each of $R_1$, $R_2$, $R_3$ and $R_4$ is independently straight chain alkylene of 1 to about 10 carbons or cycloalkylene of about 4 to about 10 carbons. More preferably, each of $R_1$, $R_2$, $R_3$ and $R_4$ is independently straight chain alkylene of 1 to about 4 carbons or cycloalkylene of about 5 to about 7 carbons. Even more preferably, each of $R_1$, $R_2$, $R_3$ and $R_4$ is independently methylene, ethylene or cyclohexylene.

In the above definitions of $X_1$, $X_3$ and $X_4$, each $R_5$ is independently hydrogen or alkyl of 1 to about 10 carbons. Preferably, each $R_5$ is independently hydrogen or alkyl of 1 to about 4 carbons. More preferably, $R_5$ is hydrogen.

In the above definitions of $Y_1$, $Y_2$ and $Y_3$, each $R_6$ is independently —$[R_7$—$X_3]_c$—$R_8$ or —$R_9$—$[X_4$—$R_{10}]_d$—Q, wherein each of c and d is independently an integer from 0 to about 100. Preferably, each of c and d is independently an integer from 0 to about 50, with integers from 0 to about 20 being more preferred. Even more preferably, each of c and d is independently an integer from 0 to about 10, with integers from 0 to about 5 being still more preferred. In certain particularly preferred embodiments, c is 0 or 1 and d is 1.

Each Q in $R_6$ above is independently a phosphate residue, —$N(R_{11})_q$, —$S(R_{11})_q$, —$P(R_{11})_q$ or —$CO_2R_{11}$, wherein q is an integer from 1 to 3. Preferably, each Q is independently a phosphate residue, —$N(R_{11})_q$ or —$CO_2R_{11}$, wherein q is 2 or 3, preferably 3.

Also in the above definition of $R_6$, each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—, wherein $X_2$ and $R_5$ are as previously described. Preferably, each of $X_3$ and $X_4$ is independently —C(=O)—$NR_5$—, —$NR_5$—C(=O)—, —C(=O)—O— or —O—C(=O)—.

In the definitions of $R_6$, $R_{11}$, and $R_{12}$ above, each $R_7$ is independently alkylene of 1 to about 20 carbons. Preferably, each $R_7$ is independently alkylene of 1 to about 10 carbons, with alkylene of 1 to about 4 carbons being preferred. More preferably, each $R_7$ is independently methylene or ethylene.

Also in the definitions of $R_6$, $R_{11}$ and $R_{12}$ above, each $R_8$ is independently hydrogen or alkyl of 1 to about 60 carbons. Preferably, each $R_8$ is independently hydrogen or alkyl of 1 to about 40 carbons, with hydrogen or alkyl of 1 to about 20 carbons being more preferred. In certain particularly preferred embodiments, each $R_8$ is independently hydrogen, methyl, dodecyl or hexadecyl.

Each of $R_9$ and $R_{10}$ in the definitions of $R_6$ and $R_{11}$ above is independently alkylene of 1 to about 20 carbons. Preferably, each of $R_9$ and $R_{10}$ is independently alkylene of 1 to about 10 carbons. More preferably, each of $R_9$ and $R_{10}$ is independently alkylene of 1 to about 4 carbons. Even more preferably, each of $R_9$ and $R_{10}$ is independently methylene or ethylene.

In Q above, each $R_{11}$ is independently —$[R_7$—$X_3]_c$—$R_8$ or —$R_9$—$[X_4$—$R_{10}]_d$—W, wherein each of c, d, $X_3$, $X_4$, $R_7$, $R_8$, $R_9$ and $R_{10}$ is independently as previously described.

Each W in $R_{11}$ above is independently a phosphate residue, —$N(R_{12})_w$, —$S(R_{12})_w$, —$P(R_{12})_w$ or —$CO_2R_{12}$, wherein w is an integer from 1 to 3. Preferably, each W is independently a phosphate residue, —$N(R_{12})_w$ or —$CO_2R_{12}$, wherein w is 2 or 3. Preferably, w is 3.

In W above, $R_{12}$ is —$[R_7$—$X_3]_c$—$R_8$, wherein each of c, $X_3$, $R_7$ and $R_8$ is independently as previously described.

In the above formulas (I), (II) and (III), it is intended that when any symbol appears more than once in a particular formula or substituent, its meaning in each instance is independent of the other. Also in the above formulas (I), (II) and (III), it is intended that when each of two or more adjacent symbols is defined as being "a direct bond" to provide multiple, adjacent direct bonds, the multiple and adjacent direct bonds devolve into a single direct bond.

Specific examples of the above cationic lipids include, for example, N,N'-Bis (dodecyaminocarbonylmethylene)-N,N'-bis (β-N,N,N-trimethylammoniumethyl-aminocarbonylmethylene)-ethylenediamine tetraiodide; N,N"-Bis (hexadecylamino-carbonylmethylene)-N,N',N"-tris (β-N,N,N-trimethylammoniumethylaminocarbonyl-methylenediethylenetriamine hexaiodide; N,N'-Bis (dodecylaminocarbonylmethylene)-N,N"-bis(β-N,N,N-trimethylammoniumethylaminocarbonylmethylene) cyclohexylene-1,4-diamine tetraiodide; 1,1,7,7-tetra-(β-N,N,N-tetramethylammoniummethylamino-carbonylmethylene)-3-hexadecylaminocarbonylmethylene-1,3,7-triaazaheptane heptaiodide; and N,N,N'N'-tetra (β-N,N,N-trimethylammoniumethylaminocarbonylmethylene)-N'-(1,2-dioleoylglycero-3-phosphoethanolaminocarbonylmethylene)-diethylenetriamine tetraiodide. In a preferred embodiment, the cationic lipid in the composition of the present invention is a fluorinated cationic lipid. Any of the cationic lipids described herein may be fluorinated by replacing at least one hydrogen atom with a fluorine atom. One skilled in the art will recognize that countless other natural and synthetic variants carrying positive charged moieties will also function in the invention.

Anionic counter ions which be used with the cationic lipids include, for example, ethylene diamine tetraacetic acid (EDTA) and diethylene triamine pentaacetic acid (DTPA), and 1, 4, 7, 10-tetraazocyclododecane-N', N', N", N"-tetraacetic acid (DOTA). Other negatively charged species which function as counter ions include, for example, monatomic and polyatomic anions such as dicarboxylic acids, teraphthalic acid, sulfide ions, sulfite ions, sulfate ions, oxide ions, nitride ions, carbonate ions and phosphate ions; polymers and copolymers of acrylic acid, methacrylic acid, other derivatives of acrylic acid, polymers with pendant $SO_3H$ groups such as sulfonated polystyrene and polystyrene with carboxylic acid groups. Preferably, the negatively charged counter ions are divalent, trivalent or multivalent.

In the compositions of the present invention, the lipids covalently bonded to polymers include, for example, lipids covalently bonded to hydrophilic polymers. Suitable hydrophilic polymers for covalent bonding to lipids include, for example, polyalkyleneoxides such as, for example, polyethylene glycol (PEG) and polypropylene glycol (PPG), polyvinyl-pyrrolidones, polyvinylalkylethers, such as a polyvinylmethyl ether, polyacrylamides, such as, for example, polymethacrylamides, polydimethylacrylamides and polyhydroxy-propylmethacrylamides, polyhydroxyalkyl(meth)acrylates, such as polyhydroxyethyl acrylates, polyhydroxypropyl methacrylates, polyalkyloxazolines, such as polymethyloxazolines and polyethyloxazolines, polyhydroxyalkyloxazolines, such as polyhydroxyethyloxazolines, polyhyhydroxypropyloxazolines, polyvinyl alcohols, polyphosphazenes, poly(hydroxy-alkylcarboxylic acids), polyoxazolidines, polyaspartamide, and polymers of sialic acid (polysialics). Preferably, the hydrophilic polymers are polyethylene glycol, polyvinyl pyrrolidone, polyvinyl alcohol, polypropylene glycol, a polyvinylalkylether, a polyacrylamide, a polyalkyloxazoline, a polyhydroxyalkyloxazoline, a polyphosphazene, a polyoxazolidine, a polyaspartamide, a polymer of sialic acid, a polyhydroxyalkyl(meth)acrylate or a poly (hydroxyalkylcarboyxlic acid). More preferably, the hydrophilic polymers are PEG, PPG, polyvinylalcohol, polyvinylpyrrolidone and copolymers thereof, with PEG and PPG polymers being more preferred and PEG polymers being even more prefered. The polyethylene glycol may be, for example, PEG 2000, PEG 5000 or PEG 8000, which have weight average molecular weights of 2000, 5000 and 8000 daltons, respectively. Preferably, the polyethylene glycol has a molecular weight of about 500 to about 20,000, more preferably from about 1,000 to about 10,000. Other suitable polymers, hydrophilic and otherwise, will be apparent to one skilled in the art based on the present disclosure. Polymers which may be attached to the lipid via alkylation or acylation reactions onto the surface of the liposome are particularly useful for improving the stability and size of the distribution of the liposomes. Exemplary lipids which are covalently bonded to hydrophilic polymers include, for example, dipalmitoylphosphatidylethanolamine-PEG, dioleoylphosphatidylethanolamine-PEG and distearylphosphatidylethanolamine-PEG, more preferably dipalmitoylphosphatidylethanolamine-PEG.

In addition to the anionic and cationic lipids described above, other suitable lipids which may be used in the present invention include, for example, fatty acids, lysolipids, fluorinated lipids, phosphocholines, such as those associated with platelet activation factors (PAF) (Avanti Polar Lipids, Alabaster, AL), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine (DMPC); dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dimyristoylphosphatidylethanolamine (DMPE), dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; linolenic acid; linoleic acid; myristic acid; synthetic lipids described in U.S. Pat. No. 5,312,617, the disclosure of which is hereby incorporated by reference herein in its entirety; lipids bearing polymers, such as-chitin, hyaluronic acid, polyvinylpyrrolidone or polyethylene glycol (PEG), also referred to herein as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as the class of compounds referred to as TWEEN®, including, for example, TWEEN® 20, TWEEN® 40 and TWEEN® 80, commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including, glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)-hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)-carbonyl)methylamino)-octadecanoic acid; N-[12-(((7'-diethylaminocoumarin-3-yl)-carbonyl)methylamino)-octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycero-phosphoethanolamine and palmitoylhomocysteine, and/or any combinations thereof. One skilled in the art could readily determine the charge (e.g., cationic, anionic or neutral) of any of the lipids decribed herein. In a preferred embodiment, the lipids described herein are fluorinated lipids. As one skilled in the art will recognize, any of the neutral lipids described herein may be modified to cationic lipids or anionic lipids by methods that are well-known to one skilled in the art. For example, any modifiable group on a neutral lipid, such as a secondary amine, an —OH group or an anionic group or cationic group that have a zwitterionic charge balance, may be chemically modified to add or subtract a charge to the neutral lipid. When a neutral lipid is used in the compositions of the present invention, the neutral lipid is preferably a phosphocholine, a sphingolipid, a glycolipid, a glycosphingolipid, a phospholipid or a polymerized lipid.

Examples of polymerized lipids include unsaturated lipophilic chains such as alkenyl or alkynyl, containing up to about 50 carbon atoms. Further examples are phospholipids such as phosphoglycerides and sphingolipids carrying polymerizable groups; and saturated and unsaturated fatty acid derivatives with hydroxyl groups, such as for example triglycerides of d-1 2-hydroxyoleic acid, including castor oil and ergot oil. Polymerization may be designed to include hydrophilic substituents such as carboxyl or hydroxyl groups, to enhance dispersability so that the backbone residue resulting from biodegradation is water soluble. Suitable polymerizable lipids are also described, for example, by Klaveness et al, U.S. Pat. No. 5,536,490, the disclosure of which is hereby incorporated by reference herein in its entirety.

Suitable fluorinated lipids that my be used in the compositions of the present include, for example, compounds of the formula:

$C_nF_{2n+1}(CH_2)_mC(O)OOP(OO^-)O(CH_2)_wN^+(CH_3)_3C_nF_{2n+1}(CH_2)_mC(O)O$ where m is 0 to about 18, n is 1 to about 12; and w is 1 to about 8. Examples of and methods for the synthesis of these, as well as other fluorinated lipids useful in the present invention, are set forth in U.S. application Ser. No. 08/465,868, filed Jun. 6, 1995, Reiss et al, U.S. Pat. No. 5,344,930, Frezard et al, *Biochem Biophys Acta*, 1192:61–70 (1994), and Frezard et al, Art. *Cells Blood Subs and Immob Biotech.*, 22:1403–1408 (1994), the disclosures of each of which are incorporated herein by reference in their entirety. One specific example of a difluoroacyl glycerylphosphatidylcholine, nonafluorinated diacyl glycerylphosphatidylcholine, is represented by compound A, below. One skilled in the art will appreciate that analogous fluorinated derivatives of other common phospholipids (diacylphosphatidyl serine, diacylphosphatidyl ethanolamine, diacylphosphatidyl glycerol, diacylphosphatidyl glycerol, and the like) as well as fluorinated derivatives of fatty acyl esters and free fatty acids may also function in accordance with the scope of the invention. Additionally lipid based and fluorinated (including perfluorinated) surfactants may be used as stabilizing materials in the present invention.

Exemplary polymerizable and/or fluorinated lipid compounds which may be used in the compositions of the present invention are presented below.

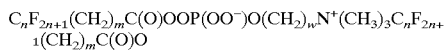

A

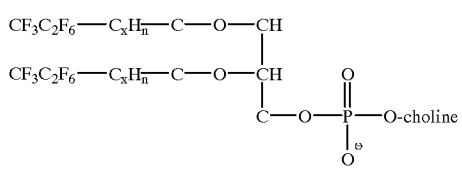

B

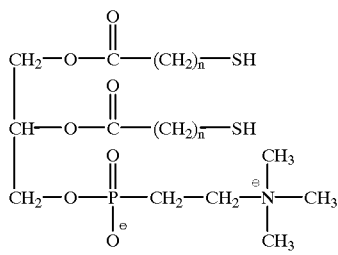

C

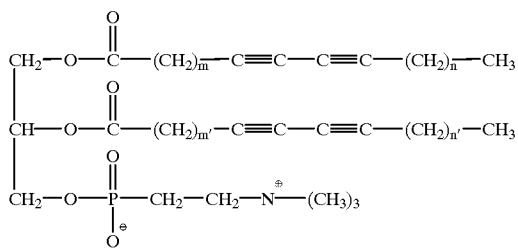

D

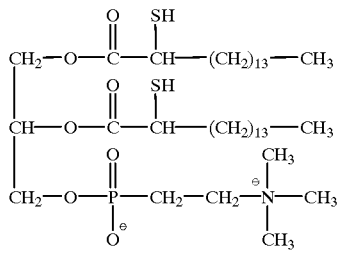

E
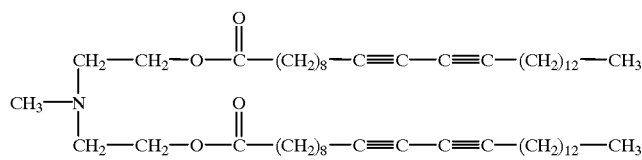
F
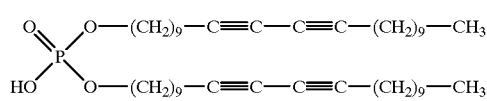
G
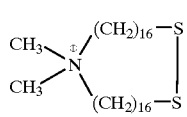
H
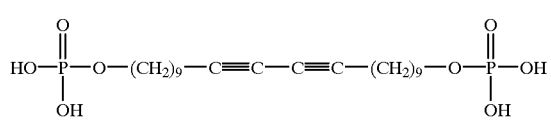
I
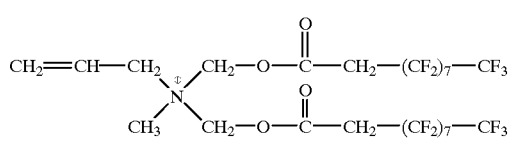
J
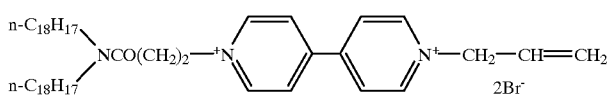
K
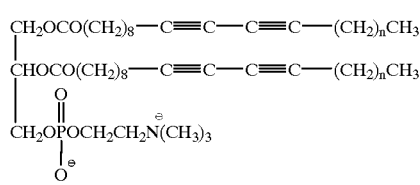
L
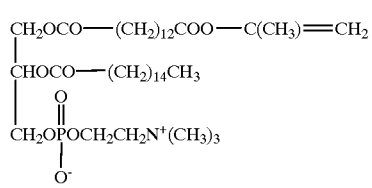
M
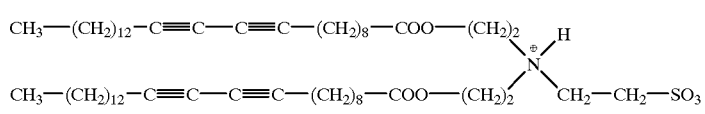
N
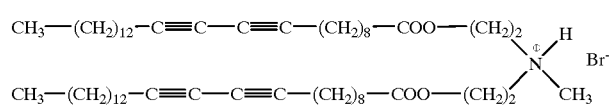
O
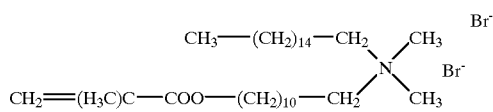
P
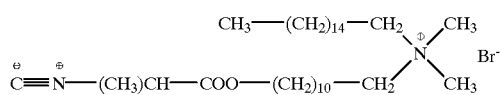

-continued

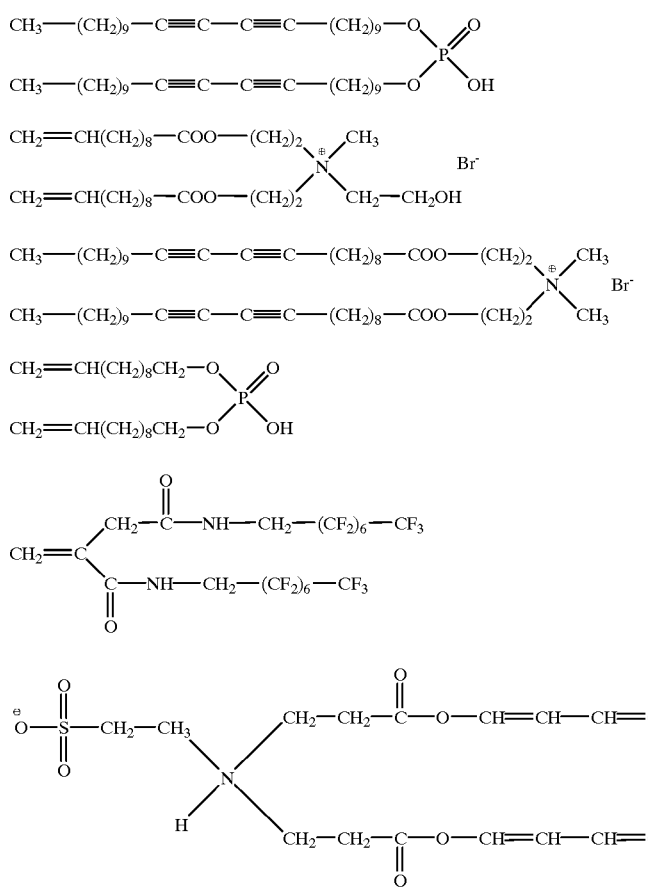

In formula A, above, x is an integer from about 8 to about 18, and n is 2x. Most preferably x is 12 and n is 24. In formulas B, C, K and L, above, m, n, m' and n' are, independently, an integer of from about 8 to about 18, preferably about 10 to about 14.

Other lipids which may be used in the present invention include fluorinated (including perfluorinated) lipid compounds. Suitable fluorinated lipid compounds include, for example, fluorinated surfactants, including alkyl surfactants, and amphiphilic compounds. A wide variety of such compounds may be employed, including, for example, the class of compounds which are commercially available as ZONYL® fluorosurfactants (the DuPont Company, Wilmington, Del.), including the ZONYL® phosphate salts (e.g., $[F(CF_2CF_2)_{3-8}CH_2CH_2O]_{1,2}P(O)(O^-NH_4^+)_{2,1}$) which have terminal phosphate groups and ZONYL® sulfate salts which have terminal sulfate groups (e.g., $F(CF_2CF_2)_{3-8}CH_2CH_2SCH_2CH_2N^+(CH_3)_3{}^-OSO_2OCH_3$). Suitable ZONYL® surfactants also include, for example, ZONYL® fluorosurfactants identified as Telomer B, including Telomer B fluorosurfactants which are pegylated (i.e., have at least one polyethylene glycol group attached thereto), also known as PEG-Telomer B, available from the DuPont Company. Other suitable fluorosurfactants are described in U.S. Pat. Nos. 5,276,146, 5,344,930, and 5,562,893, and U.S. application Ser. No. 08/465,868, filed Jun. 6, 1995, the disclosures of each of which are hereby incorporated by reference herein in their entirety.

It may also be desirable to use a fluorinated liquid compound, especially a perfluorocarbon compound or a perfluoroether compound, which is in the liquid state at the temperature of use, including, for example, the in vivo temperature of the human body, to assist or enhance the stability of the lipid and/or vesicle compositions, and especially, gas filled vesicles. Suitable liquid perfluorocarbons and liquid perfluoroethers include, for example, perfluorohexane, perfluorocyclohexane, perfluoroheptane, perfluorooctane, perfluorononane, perfluorodecane, perfluorodecalin, perfluorododecalin, perfluorooctyliodide, perfluorooctylbromide, perfluorotripropylamine, perfluorotributylamine, perfluorobutylethyl ether, bis (perfluoroisopropyl) ether, and bis(perfluoropropyl) ether. In general, perfluorocarbons and perfluoroethers comprising about six or more carbon atoms will be liquids at normal human body temperature. Among these, perfluorooctylbromide and perfluorohexane, which are liquids at room temperature, are preferred. Although not intending to be bound by any theory of operation, in the case of vesicle compositions, the liquid fluorinated compound may be situated at the interface between the gas and the membrane or wall surface of the vesicle. Thus, an additional stabilizing layer of liquid fluorinated compound may be formed on the internal surface of the stabilizing composition, and this perfluorocarbon layer may also prevent the gas from diffusing through the vesicle membrane. Preferred perfluorinated surfactants are partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the stabilizing materials and/or vesicles of the present invention.

Suitable fluorinated lipids that may be used in the compositions of the present invention also include the fluorinated compounds described in U.S. application Ser. No. 08/887,215 filed Jul. 2, 1997, the disclosure of which is hereby incorporated by reference herein in its entirety, which include the following compounds of formula (IV), formula (V), formula (VI), formula (VII), formula (VIII), formula (IX) and formula (X).

The fluorinated lipid may be a fluorinated fatty acyl derivative, such as, for example, that of formula (IV):

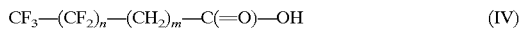

(IV)

where n is an integer of from about 7 to about 13, preferably from about 9 to about 11; and m is an integer of from 1 to about 4, preferably 1 to about 2.

The fluorinated lipid be a fluorinated surfactant, such as, for example, a PEG Telomer type compound of formula (V):

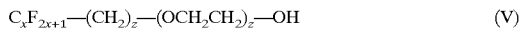

(V)

where x is an integer of from about 6 to about 12, preferably from about 8 to about 10, more preferably about 9; and z is an integer of from about 8 to about 20; preferably from about 8 to about 16; still more preferably from about 8 to about 12; even more preferably about 8 to about 10; most preferably about 9.

Further, the fluorinated lipid may be a fluorinated carbohydrate derivative, such as, for example, that of formula (VI):

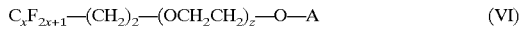

(VI)

where x is an integer of from about 6 to about 12; preferably from about 8 to about 10; more preferably 9; z is an integer of from about 8 to about 20; preferably from about 8 to about 16; more preferably from about 8 to about 12; still more preferably from about 8 to about 10; most preferably about 9; and A is a monosaccharide or a disaccharide. Suitable monosaccharides and disaccharides include, for example, allose, altrose, glucose, dextrose, mannose, glycerose, gulose, idose, galactose, talose, fructose, psicose, sorbose, rhamnose, tagatose, ribose, arabinose, xylose, lyxose, ribulose, xylulose, erythrose, threose, erythrulose, fucose, sucrose, lactose, maltose, isomaltose, trehalose, cellobiose and the like. Preferably, the monosaccharide or disaccharide is glucose, dextrose, fructose, mannose, galactose, glucosamine, galactosamine, maltose, sucrose or lactose.

The fluorinated lipid may also be a fluorinated lipophilic derivative, such as, for example, that of formula (VII), which includes the compounds described in U.S. application Ser. No. 08/465,868, filed Jun. 6, 1995, the disclosure of which is hereby incorporated by reference herein in its entirety:

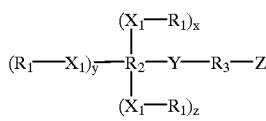

(VII)

where each of x, y and z is independently 0 or 1; each $X_1$ is independently —O—, —S—, —SO—, —SO$_2$—, —NR$_4$—, —C(=X$_2$)—, —C(=X$_2$)—O—, —O—C(=X$_2$)—, —C(=X$_2$)—NR$_4$— or —NR$_4$—C(=X$_2$)—; $X_2$ is O or S; Y is a direct bond or —X$_3$—M(=O)(OR$_5$)$_q$—O—, where q is 1 or 2; $X_3$ is a direct bond or —O—; M is P or S; Z is hydrogen, the residue of a hydrophilic polymer, a saccharide residue or —N(R$_6$)$_r$, where r is 2 or 3; each $R_1$ is independently an alkyl group of 1 to about 30 carbon atoms or a fluorinated alkyl group of 1 to about 30 carbon atoms; $R_2$ is a direct bond or an alkylene linking group of 1 to about 10 carbon atoms; $R_3$ is a direct bond or an alkylene diradical of 1 to about 10 carbon atoms; each of $R_4$ and $R_5$ is independently hydrogen or an alkyl group of 1 to about 8 carbon atoms; and each $R_6$ is independently hydrogen, an alkyl group of 1 to about 8 carbon atoms or a residue of a hydrophilic polymer; provided that at least one of x, y and z is 1, at least one of $R_1$ is a fluorinated alkyl group of 1 to about 30 carbon atoms; provided that when $R_2$ is a direct bond, two of x, y and z are each 0.

In formula (VII), each of x, y and z is independently 0 or 1, provided that at least one of x, y and z is 1. In some embodiments, two of x, y and z are each 0. In other embodiments, one of x, y and z is 0 or 1 and the other two of x, y and z are each 1, with one of x, y and z being 0 and the other two of x, y and z being 1 being more preferred. In other embodiments, each of x, y and z is 1.

Each $X_1$ is independently —O—, —S—, —SO—, —SO$_2$—, —NR$_4$—, —C(=X$_2$)—, —C(=X$_2$)—O—, —O—C(=X$_2$)—, —C(=X$_2$)—NR$_4$— or —NR$_4$—C(=X$_2$)—. Preferably, each $X_1$ is independently —O—, —S—, —C(=X$_2$)—, —C(=X$_2$)—O—, —O—C(=X$_2$)—, —C(=X$_2$)—NR$_4$— or —NR$_4$—C(=X$_2$)—. More preferably, each $X_1$ is independently —C(=X$_2$)—O— or —O—C(=X$_2$)—, most preferably —C(=X$_2$)—O—.

Each $X_2$ is O or S, preferably O.

Y is a direct bond or —X$_3$—M(=O)(OR$_5$)$_q$—O—, where q is 1 or 2. Preferably, Y is —X$_3$—M(=O)(OR$_5$)$_q$—O—. M is P or S, preferably P. $X_3$ is a direct bond or —O—, preferably, a direct bond.

Z is hydrogen atom, the residue of a hydrophilic polymer, a saccharide residue or —N(R$_6$)$_r$, where r is 2 or 3. In preferred embodiments, Z is —N(R$_6$)$_r$.

Each $R_1$ is independently an alkyl group of 1 to about 30 carbon atoms or a fluorinated alkyl group of 1 to about 30 carbon atoms, provided that at least one of $R_1$ is a fluorinated alkyl group of 1 to about 30 carbon atoms. Thus, when only one of x, y and z is 1, $R_1$ is necessarily a fluorinated alkyl group of 1 to about 30 carbon atoms. In preferred embodiments, where one or none of x, y and z is 0, and preferably where one of x, y and z is 0 and the other two of x, y and z are each 1, at least one of $R_1$ is an alkyl group of 1 to about 30 carbon atoms and at least one of $R_1$ is a fluorinated alkyl group of 1 to about 30 carbon atoms. In other embodiments, each $R_1$ is independently a fluorinated alkyl group of 1 to about 30 carbon atoms. When a fluorinated alkyl group of 1 to about 30 carbon atoms, $R_1$ is preferably a polyfluorinated alkyl group of 1 to about 30 carbon atoms, with a perfluorinated alkyl group of 1 to about 30 carbon atoms being more preferred. When a fluorinated alkyl group of 1 to about 30 carbon atoms, $R_1$ is preferably $C_nF_{2n+1}$—(CH$_2$)$_m$—, where n is 1 to about 16, preferably about 9 to about 14, and m is 0 to about 18, preferably 1 to about 10, more preferably 1 to about 4.

$R_2$ is a direct bond or an alkylene linking group of 1 to about 10 carbon atoms, provided that when $R_2$ is a direct bond, two of x, y and z are each 0. Preferably, $R_2$ is a direct bond or an alkylene linking group of 1 to about 4 carbon atoms. More preferably, $R_2$ is an alkylene linking group of about 3 carbons. Even more preferably, $R_2$ is —CH$_2$—CH$_2$—CH$_2$—.

$R_3$ is a direct bond or an alkylene diradical of 1 to about 10 carbons. Preferably, $R_3$ is a direct bond or an alkylene diradical of 1 to about 4 carbon atoms. More preferably, $R_3$ is an alkylene diradical of about 2 carbon atoms. Even more preferably, $R_3$ is —$CH_2CH_2$—.

Each of $R_4$ and $R_5$ is independently a hydrogen atom or an alkyl group of 1 to about 8 carbon atoms, preferably of 1 to about 4 carbon atoms. More preferably, each of $R_4$ and $R_5$ is a hydrogen atom.

$R_6$ is a hydrogen atom, an alkyl group of 1 to about 8 carbon atoms or a residue of a hydrophilic polymer. Preferably, $R_6$ is a hydrogen atom or an alkyl group of 1 to about 4 carbon atoms. More preferably, $R_6$ is a hydrogen atom or a methyl group, with a methyl group being even more preferred.

When any symbol appears more than once in a particular formula or substituent, such as in formula (VII), its meaning in each instance is independent of the other, unless otherwise indicated. This independence of meaning is subject to any of the stated provisos. When each of two or more adjacent symbols is defined as being "a direct bond" to provide multiple, adjacent direct bonds, the multiple and adjacent direct bonds devolve into a single direct bond.

Z and $R_6$ in the definition of Z in formula (VII), can be the residue of a hydrophilic polymer. Exemplary polymers from which Z and/or $R_6$ can be derived include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates. The molecular weight of the polymers from which Z and/or $R_6$ are derived may vary, and is generally about 50 to about 5,000,000, with polymers having a molecular weight of about 100 to about 50,000 being preferred. More preferred polymers have a molecular weight of about 150 to about 10,000, with molecular weights of 200 to about 8,000 being even more preferred.

Preferred polymers from which Z and/or $R_6$ are derived include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers will be apparent to one skilled in the art in view of the present disclosure. Generally, polymers from which Z and/or $R_6$ are derived include polymers that can be incorporated in the fluorinated lipids via alkylation or acylation reactions.

As with the various polymers exemplified above, the polymeric residues can contain functional groups in addition to those typically involved in linking the polymeric residues to the fluorinated lipids. Such functionalities include, for example, carboxyl, amine, hydroxy and thiol groups. These functional groups on the polymeric residues can be further reacted, if desired, with materials which are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins and nucleosides.

In addition to residues of hydrophilic polymers, Z in formula (VII) can be a saccharide residue. Exemplary saccharides from which Z can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides from which Z is derived include saccharides that can be incorporated in the fluorinated lipids via alkylation or acylation reactions.

Preferred fluorinated lipids that are within the scope of formula (VII) are the fluorinated compounds of the formula (VIIa):

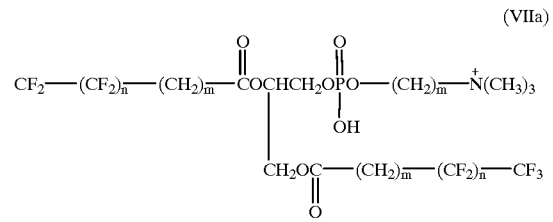

where n is an integer of from about 7 to about 13, preferably from about 9 to about 11; and m is an integer of from about 1 to about 4, preferably 1 to about 2.

The fluorinated compound may also be a compound of formula (VIII):

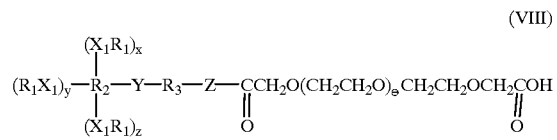

where $R_1$, $R_2$, $R_3$, $X_1$, Y, Z, x, y and z are as defined in formula (VII), including the preferred embodiments thereof, and where e is an integer of from 1 to about 30, preferably about 3 to about 20, more preferably about 4 to about 16, still more preferably about 4 to about 12, most preferably about 7 to about 9.

In a preferred embodiment, the compound of formula (VIII) may be a compound of the formula (VIIIa):

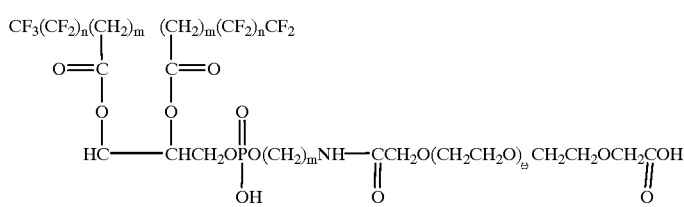

(VIIIa)

where n and m are as defined above in formula (VIIa) and where e is as defined above in formula (VIII).

Additionally, the fluorinated compound may be a fluorinated fatty acyl derivative, such as, for example, that of formula (IX):

$$CF_3\text{—}J\text{—}T\text{—}C(\text{=}O)\text{—}OH \quad (IX)$$

Still further, the fluorinated compound may be a fluorinated lipophilic derivative, such as, for example, that of formula (X):

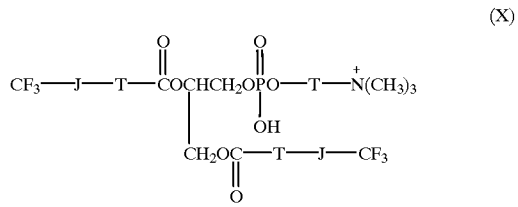

In the above formulas (IX) and (X), J is $(-(C=C)_{p1}-(CF_2)_{p2}-(C=C)_{p3}-(CF_2)_{p4}-(C=C)_{p5}-(CF_2)_{p6}-(C=C)_{p7}-(CF_2)_{p8}-(C=C)_{p9}-(CF_2)_{p10}-(C=C)_{p11}-(CF_2)_{p12}-(C=C)_{p13}-)$, where p1, p2, p3, p4, p5, p6, p7, p8, p9, p10, p11, p12 and p13 are independently an integer of 0, 1 or 2; providedthatthe sum of (p1+p2+p3+p4+p5+p6+p7+p8+p9+p10+p11+p12+p13) is an integer of from about 7 to about 13, and provided that at least one of p2, p4, p6, p8, p10 or p12 is an integer of at least 1; and where T is $-(C=C)_{t1}-(CH_2)_{t2}-(C=C)_{t3}-(CH_2)_{t4}-$, where t1, t2, t3, and t4 are independently an integer of 0, 1 or 2; provided that the sum of (t1+t2+t3+t4) is an integer of from 1 to about 4.

Other suitable fluorinated compounds for use as the stabilizing materials and/or vesicles of the present invention are described in U.S. Pat. No. 5,562,893, the disclosure of which is hereby incorporated herein by reference in its entirety. For example, synthetic organic monomeric repeating units may be used to form polymers suitable as stabilizing materials, including hydroxyacids, lactones, lactides, glycolides, acryl containing compounds, aminotriazol, orthoesters, anyhdrides, ester imides, imides, acetals, urethanes, vinyl alcohols, enolketones, and organosiloxanes.

The method of introducing fluorine into any of these materials is known in the art. For example, the introduction of perfluoro-t-butyl moieties is described in U.S. Pat. No. 5,234,680, the disclosure of which is hereby incorporated by reference herein in its entirety. These methods generally involve the reaction of perfluoroalkyl carbanions with host molecules, such as $(CF_3)_3C^-+R\text{—}X\rightarrow(CF_3)_3C\text{—}R$, where R is a host molecule and X is a good leaving group, such as bromine, chlorine, iodine or a sulfonato group. After adding a leaving group to the foregoing stabilizing material using methods well known in the art, perfluoro-t-butyl moieties can then be easily introduced to these derivatized stabilizing materials as described above. Additional methods are known in the art for the introduction of trifluoromethyl groups into various organic compounds. For example, trifluoromethyl groups may be introduced by nucleophilic perfluoroalkylation using perfluoroalkyl-trialkylsilanes. Fluorine can be introduced into any of the aforementioned stabilizing materials or vesicles either in their monomeric or polymeric form. Preferably, fluorine moieties are introduced into monomers, such as fatty acids, amino acids or polymerizable synthetic organic compounds, which are then polymerized for subsequent use as stabilizing materials and/or vesicles.

The introduction of fluorine into stabilizing materials and/or vesicles may also be accomplished by forming vesicles in the presence of a perfluorocarbon gas. For example, when vesicles are formed from proteins, such as human serum albumin in the presence of a perfluorocarbon gas, such as perfluoropropane, using mechanical cavitation, fluorine from the gas phase becomes bound to the protein vesicles during formation. The presence of fluorine in the vesicles and/or stabilizing materials can be detected by NMR of vesicle debris which has been purified from disrupted vesicles. Fluorine can also be introduced into stabilizing materials and/or vesicles using other methods, such as sonication, spray-drying or emulsification techniques.

Another way in which fluorine can be introduced into the stabilizing material and/or vesicle is by using a fluorine-containing reactive compound. The term "reactive compound" refers to compounds which are capable of interacting with the stabilizing material and/or vesicle in such a manner that fluorine moieties become covalently attached to the stabilizing material and/or vesicle. When the stabilizing material is a protein, preferred reactive compounds are either alkyl esters or acyl halides which are capable of reacting with the protein's amino groups to form an amide linkage via an acylation reaction. The reactive compound can be introduced at any stage during vesicle formation, but is preferably added to the gas phase prior to vesicle formation. For example, when vesicles are to be made using mechanical or ultrasound cavitation techniques, the reactive compound can be added to the gas phase by bubbling the gas to be used in the formation of the vesicles (starting gas) through a solution of the reactive compound into the gas phase. The resultant gas mixture, which now contains the starting gas and the reactive compound, is then used to form vesicles. The vesicles are preferably formed by sonication of human serum albumin in the presence of a gas mixture, as described in U.S. Pat. No. 4,957,656, the disclosure of which is hereby incorporated herein by reference in its entirety.

Suitable fluorine containing alkyl esters and acyl halides for use as stabilizing materials and/or vesicle forming materials in the present invention include, for example, diethyl hexafluoroglutarate, diethyl tetrafluorosuccinate, methyl heptafluorobutyrate, ethyl heptafluorobutyrate, ethyl pentafluoropropionate, methyl pentafluoropropionate, ethyl perfluorooctanoate, methyl perfluorooctanoate, nonafluoropentanoyl chloride, perfluoropropionyl chloride, hexafluoroglutaryl chloride and heptafluorobutyiyl chloride.

Other fluorine containing reactive compound can also be synthesized and used as the stabilizing materials and/or vesicle forming materials in the present invention, including, for example, aldehydes, isocyanates, isothiocyanates, epoxides, sulfonyl halides, anhydrides, acid halides and alkyl sulfonates, which contain perfluorocarbon moieties, including —$CF_3$, —$C_2F_5$, —$C_3F_4$ and —$C(CF_3)_3$. These reactive compounds can be used to introduce fluorine moieties into any of the above stabilizing materials by choosing a combination which is appropriate to achieve covalent attachment of the fluorine moiety.

Sufficient fluorine should be introduced to decrease the permeability of the vesicle to the aqueous environment. This will result in a slower rate of gas exchange with the aqueous environment which is evidenced by enhanced pressure resistance. Although the specific amount of fluorine necessary to stabilize the vesicle will depend on the components of the vesicle and the gas contained therein, after introduction of fluorine the vesicle will preferably contain 0.01 to 20% by weight, and more preferably about 1.0 to 10% by weight fluorine.

Additionally, oils and fluorinated oils may be used as stabilizing materials and/or to stabilize the compositions of the present invention. Suitable oils include, for example, soybean oil, peanut oil, canola oil, olive oil, safflower oil, corn oil, almond oil, cottonseed oil, ethyl oleate, isopropyl myristate, isopropyl palnitate, mineral oil, myristyl alcohol, octyldodecanol, persic oil, sesame oil, squalene, myristyl oleate, cetyl oleate, myristyl palmitate, or any other known ingestible oil. The oils described herein may be fluorinated, such as triolein with a fluorine ($F_2$) gas. A "fluorinated oil" refers to an oil in which at least one hydrogen atom of the oil is replaced with a fluorine atom. Preferably, at least two or more of the hydrogen atoms in the oil are replaced with fluorine atoms. Other suitable fluorinated oils are described, for example, in U.S. Pat. No. 5,344,930, the disclosure of which is hereby incorporated by reference herein in its entirety.

The stability of vesicles may be attributable, at least in part, to the materials from which the vesicles are made, and it is often not necessary to employ additional stabilizing materials, although it is optional and may be preferred to do so. In addition to the lipids discussed above, the compositions described herein may comprise one or more other stabilizing materials. Exemplary stabilizing materials include, for example, surfactants, fluorosurfactants and polymers. The stabilizing materials may be employed to assist in the formation of vesicles and/or to assure substantial encapsulation of the gases, gaseous precursors and/or bioactive agents. Even for relatively insoluble, non-diffusible gases, such as perfluoropropane or sulfur hexafluoride, improved vesicle compositions may be obtained when one or more stabilizing materials are utilized in the formation of the gas and/or gaseous precursor filled vesicles. These compounds may help improve the stability and the integrity of the vesicles with regard to their size, shape and/or other attributes. Suitable surfactants and fluorosurfactants useful as stabilizing materials for preparing the gas and/or gaseous precursor filled vesicles include the surfactants and fluorosurfactants described in detail herein.

Polymers useful to stabilize the vesicles of the present invention may be of natural, semi-synthetic (modified natural) or synthetic origin. Suitable natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolyner or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics®, commercially available from BASF, Parsippany, N.J.), polyoxyethylene, and polyethylene terephthlate), polypropylenes (such as, for example, polypropylene glycol), polyurethanes (such as, for example, polyvinyl alcohol (.PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of vesicles which employ polymers to stabilize vesicle compositions will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

The compositions of the present invention may be modified and further stabilized, for example, by the addition of one or more of a wide variety of (i) viscosity modifiers, including, for example, carbohydrates and their phosphorylated and sulfonal:ed derivatives; polyethers, preferably with molecular weight ranges between 400 and 100,000; and di- and trihydroxy alkanes and their polymers, preferably with molecular weight ranges between 200 and 50,000; (ii) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, and poloxamer 181, Pluronics® (BASF, Parsippany, N.J.), polyoxyethylene 50 stearate, polyoxyl 35 castor oil, polyoxl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, and emulsifying wax; (iii) suspending and/or viscosity-increasing agents, including, for example, acacia, agar, alginic acid, aluminum monostearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, Zeolites®, methylcellulose, pectin, polyethylene oxide, povidone, propylene glycol alginate, silicon dioxide, sodium alginate, tragacanth, xanthin gum, α-d-gluconolactone, glycerol and mannitol; (iv) synthetic suspending agents, such as polyethylene glycol (PEG), polyvinylpyrrolidone (PVP), polyvinylalcohol (PVA), polypropylene glycol (PPG), and polysorbate; and (v) tonicity raising agents which stabilize and add tonicity, including, for example, sorbitol, mannitol, trehalose, sucrose, propylene glycol and glycerol.

The compositions of the present invention are desirably formulated in an aqueous environment which can induce the lipids, because of their hydrophobichydrophilic nature, to form vesicles, which may be the most stable configuration which can be achieved in such an environment. Diluents which may be used to create such an aqueous environment include, for example, water, normal saline, physiological saline, deionized water and water containing one or more dissolved solutes, such as salts or sugars.

The present stabilizing materials or compositions preferably comprise a gas, such as an inert gas. The gas provides the stabilizing materials or compositions with enhanced reflectivity, particularly in connection with stabilizing materials or compositions in which the gas is entrapped within the stabilizing materials or compositions. This may increase their effectiveness as drug delivery vehicles or contrast agents.

Preferred gases are inert and biocompatible, and include, for example, air, noble gases, such as helium, rubidium hyperpolarized xenon, hyperpolarized argon, hyperpolarized helium, neon, argon and xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases, and mixtures thereof. Paramagnetic gases, such as $^{17}O_2$ may also be used in the stabilizing materials and vesicles. It may also be desirable to incorporate a precursor to a gaseous substance in the stabilizing materials or compositions. Such gaseous precursors include materials that are capable of being converted to a gas in vivo, preferably where the gaseous precursor and gas produced are biocompatible.

Preferably, the gaseous precursor materials comprise compounds that are sensitive to changes in temperature. Exemplary of suitable gaseous precursors which are sensitive to changes in temperature are the perfluorocarbons and perfluoro ethers. As the artisan will appreciate, a particular perfluorocarbon or perfluoro ether may exist in the liquid state when the stabilizing materials are first made, and are thus used as a gaseous precursor. Alternatively, the perfluorocarbon or perfluoro ether may exist in the gaseous state when the stabilizing materials are made, and are thus used directly as a gas. Whether the perfluorocarbon or perfluoro ether is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As known to one of ordinary skill in the art, the effective boiling point of a substance may be related to the pressure to which that substance is exposed. This relationship is exemplified by the ideal gas law: $PV=nRT$, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

A wide variety of materials can be used as liquids, gases and gaseous precursors in combination with the stabilizing materials and compositions of the present invention. For gaseous precursors, it is only required that the material be capable of undergoing a phase transition to the gas phase upon passing through the appropriate temperature. Suitable liquids, gases and/or gaseous precursors for use in the present invention include, for example, hexafluoroacetone, 1,3-dichlorotetrafluoroacetone, tetrafluoroallene, boron trifluoride, 1,2,3-trichloro-2-fluoro-1,3-butadiene, hexafluoro-1,3-butadiene, 1-fluorobutane, perfluorobutane, decafluorobutane, perfluoro-1-butene, perfluoro-2-butene, 2-chloro-1,1,1,4,4,4-hexafluorobutyne, 2-chloro-1,1,1,4,4,4-hexafluoro- 2-butene, perfluoro-2-butyne, octafluorocyclobutane, perfluorocyclobutene., perfluorocyclobutane, perfluorocyclopentane, octafluorocyclopentene, perfluorocyclopropane, 1,1,1-trifluorodiazoethane, hexafluorodimethylamine, perfluoroethane, perfluoropropane, perfluoropentane, hexafluoroethane, hexafluoropropylene, 1,1,2,2,3,3,4,4-octafluorobutane, 1,1,1,3,3-pentafluorobutane, octafluoropropane, octafluorocyclopentene, 1,1-dichlorofluoroethane, hexafluoro-2-butyne, octafluoro-2-butene, hexafluorobuta-1,3-diene, perfluorodimethylamine, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1,1-trichloro-2,2,2-trifluoroethane, 1,1-dichloro-1,2-difluoroethylene, 1,1-dichloro-1,2,2,2-tetrafluoroethane, 1-chloro-1,1,2,2,2-pentafluoroethane, 1,1-difluoro-2-chloroethane, 1,1-dichloro-2-fluoroethane, dichloro-1,1,2,2-tetrafluoroethane, 1-chloro-1,1,2,2-tetrafluoroethane, 2-chloro-1,1-difluoroethane, 1,1,2-trifluoro-2-chloroethane, 1,2-difluorochloroethane, chloropentafluoroethane, dichlorotrifluoroethane, fluoroethane, nitropentafluoroethane, nitrosopentafluoroethane, perfluoroethylamine, 1,2-dichloro-2,2-difluoroethane, 1,1-dichloro-1,2-difluoroethane, 1,2-dichloro-1,1,3-trifluoropropane, 1,2-difluoroethane, 1,2-difluoroethylene, trifluoromethanesulfonylchloride, trifluoromethanesulfenylchloride, (pentafluorothio) trifluoromethane, trifluoromethanesulfonylfluoride, bromodifluoronitroso-methane, bromofluoromethane, bromochlorodifluoromethane, bromochlorofluoromethane, bromotrifluoromethane, bromotrifluoroethane, chlorodifluoronitromethane, chlorofluoromethane, chlorotrifluoromethane, chlorodifluoromethane, dibromofluoromethane, dibromodifluoromethane, dichlorodifluoromethane, dichlorofluoromethane, 1-bromoperfluorobutane, difluoromethane, difluoroiodomethane, fluoromethane, perfluoromethane, iodotrifluoromethane, iodotrifluoroethylene, nitrotrifluoromethane, nitrosotrifluoromethane, tetrafluoromethane, trichlorofluoromethane, trifluoromethane, perfluoropent-1-ene, 1,1,1,2,2,3-hexafluoropropane, 2,2-difluoropropane, heptafluoro-1-nitropropane, heptafluoro-1-nitrosopropane, heptafluoro-2-iodopropane, perfluoropropane, hexafluoropropane, 1,1,1,2, 3,3-hexafluoro-2,3-dichloropropane, 1-bromo-1,1,2,3,3,3-hexafluoropropane, 1-bromoperfluoropropane, 2-chloropentafluoro-1,3-butadiene, 3-fluoropropane, 3-fluoropropylene, perfluoropropylene, perfluorotetrahydropyran, perfluoromethyltetrahydrofuran, perfluorobutylmethyl ether, perfluoromethyl-n-butyl ether, perfluoromethylisopropyl ether, perfluoromethyl-t-butyl ether, perfluorobutyl ethyl ether, perfluoromethylpentyl ether, 3,3,3-trifluoropropyne, 3-fluorostyrene, sulfur (di)decafluoride ($S_2F_{10}$), sulfur hexafluoride, selenium hexafluoride, trifluoroacetonitrile, trifluoromethyl peroxide, trifluoromethyl sulfide, tungsten hexafluoride, 1-bromononafluorobutane, 1-chloro-1-fluoro-1-bromomethane, 1-bromo-2,4-difluorobenzene, 2-iodo-1,1,1-trifluoroethane, bromine pentafluoride, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, bis(perfluoroisopropyl) ether, bis(perfluoropropyl) ether, perfluoro isobutyl methyl ether, perfluoro n-propyl ethyl ether, perfluoro cyclobutyl methyl ether, perfluoro cyclopropyl ethyl ether, perfluoro isopropyl methyl ether, perfluoro n-propyl methyl ether, perfluorodiethyl ether, perfluoro cyclopropyl methyl ether, perfluoro methyl ethyl ether, perfluoro dimethyl ether, air, noble gases, such as helium, rubidium hyperpolarized xenon, hyperpolarized argon, hyperpolarized helium, neon, argon, xenon, carbon dioxide, nitrogen, isopropyl acetylene, allene, 1,2-butadiere, 2,3-butadiene, 1,3-butadiene, 2-methyl-1,3-butadiene, butadiene, 2-methylbutane, 1-butene, 2-butene, 2-methyl-1-butene, 3-methyl-1-butene, 4-phenyl-3-butene-2-one, 2-methyl-1-butene-3-yne, butyl nitrate, 1-butyne, 2-butyne, 3-methyl-1-butyne, 2-bromobutyraldehyde, carbonyl sulfide, crotononitrile, cyclobutane, methylcyclobutane, cyclopropane, 3-chlorocyclopentene, dimethylamine, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, dimethylethylamine, bis(dimethylphosphine) amine, dimethyloxonium chloride, 2,3-dimethyl-2-norbomane, 1,3-dioxolane-2-one, 1,1-dichloroethane, 1,1-dichloroethylene, chloroethane, 1,1-dichloroethane, methane, chlorodinitromethane, iodomethane, disilanomethane, 2-methylbutane, metbyl ether, methyl isopropyl ether, methyllactate, methylnitrite, methylsulfide, methyl vinyl ether, neon, neopentane, nitrogen, nitrous oxide, 1,2,3-nonadecanetricarboxylic acid 2-hydroxytrimethyl ester, 1-nonene-3-yne, 1,4-pentadiene, n-pentane, 4-amino-4-methylpentan-2-one, 1-pentene, 2-pentene (cis and trans), 3-bromopent-1-ene, 2-chloropropane, tetrachlorophthalic acid, 2,3,6-trimethylpiperidine, propane, 1-chloropropane, 1-chloropropylene, chloropropylene-(trans), chloropropane-(trans), 2-chloropropylene, 2-aminopropane, 1,2-epoxypropane, propene, propyne, 2,4-diaminotoluene, vinyl acetylene, vinyl ether, ethyl vinyl ether, 5-bromovaleryl chloride, 1-bromoethane, 6-bromo-1-hexene, 2-bromo-2-nitropropane, 2-bromo-5-nitrothiopbene, 2-bromopropene, 3-chloro-5,5-dimethyl-2-cylohexene, 2-chloro-2-methylpropane and mixtures thereof. One skilled in the art could determine whether any compound is a gas, a gaseous precursor or a liquid at any given temperature, in view of the present disclosure.

Preferably, the gas, gaseous precursor and/or liquid compound is perfluoropropane, perfluorobutane, 1-chloro-1-fluoro-1-bromomethane; 1,1,1-trichloro-2,2,2-trifluoroethane; 1,2-dichloro-2,2-difluoroethane; 1,1-dichloro-1,2-difluoroethane; 1,2-dichloro-1,1,3-trifluoropropane; 1,1,2,2,3,3,4,4-octafluorobutane; 1,1,1,3,3-pentafluorobutane; 1-bromoperfluorobutane; perfluorocyclohexane; 1-bromo-2,4-difluorobenzene; 2-iodo-1,1,1-trifluoroethane; 5-bromovaleryl chloride; 1,3-dichlorotetrafluoroacetone; bromine pentafluoride; 1-bromo-1,1,2,3,3,3-hexafluoropropane; 2-chloro-1,1,1,4,4,4-hexafluoro-2-butene; 2-chloropentafluoro-1,3-butadiene; iodotrifluoroethylene; 1,1,2-trifluoro-2-chloroethane; 1,2-difluorochloroethane; 1,1-difluoro-2-chloroethane; 1,1-dichloroflouroethane; heptafluoro-2-iodopropane; 3-fluorobenzaldehyde; 2-fluoro-5-nitrotoluene; 3-fluorostyrene; perfluoro-2-methyl-2-pentene; 3,5-difluoroaniline; 2,2,2-trifluoroethylacrylate; 3-(trifluoromethoxy)-acetophenone; 1,1,2,2,3,3,4,4-octafluorobutane; 1,1,1,3,3-pentafluorobutane; perfluorocyclohexane; perfluoromethyl-n-butyl either; perfluoromethylisopropyl ether; perfluoromethyl-t-butyl ether; 1-fluorobutane; 1-bromoethane; 6-bromo-1-hexene; 2-bromo-2-nitropropane; 2-bromo-5-nitrothiophene; 2-bromopropene; 3-chloro-5,5-dimethyl-2-cyclohexene and 2-chloro-2-methyl-propane. Under conditions of shaking or emulsification followed optionally by lyophilization these compounds will partition into the internal space of the compositions and becomed entrapped against rapid diffusion.

Preferred gases and gaseous precursors are compounds which are sparingly soluble in water but which may, in some cases, be liposoluble, such as low molecular weight alkanes and their fluorinated analogs. In preferred embodiments, the gas comprises a fluorinated gas, which includes gases containing one or more fluorine atoms. Preferred are gases which contain more than one fluorine atom, with perfluorocarbons (fully fluorinated fluorocarbons) being more preferred. Preferred gases and gaseous precursors include, for example, fluorinated carbons, perfluorocarbons, sulfur hexafluoride, perfllioro ethers and combinations thereof.

Preferred perfluorocarbons generally have from 1 to about 4 carbon atoms and from about 4 to about 10 fluorine atoms, most preferably perfluorobutane ($C_4F_{10}$). Preferred gaseous precursors generally have from about 4 to about 8 carbon atoms, more preferably about 5 or about 6 carbon atoms, and from about 12 to about 15 fluorine atoms. The perfluorocarbon gas may be saturated, unsaturated or cyclic, including, for example, perfluoromethane, perfluoroethane, perfluoropropane, perfluorocyclopropane, perfluorobutane, perfluorocyclobutane, perfluoropentane, perfluorocylcopentane, and mixtures thereof. More preferably, the perfluorocarbon gas is perfluoropentane, perfluoropropane or perfluorobutane, with perfluoropropane being particularly preferred.

Preferred ethers for use in the present invention include partially or fully fluorinated ethers, preferably having a boiling point of from about 36° C. to about 60° C. Fluorinated ethers are ethers in which one or more hydrogen atoms is replaced by a fluorine atom. Fluorinated ethers have the general formula $CX_3(CX_2)_n$—O—$(CX_2)_nCX_3$, wherein X is a hydrogen atom, a fluorine atom or another halogen atom provided that at least one of X is a fluorine atom. Generally, fluorinated ethers containing about 4 to about 6 carbon atoms will have a boiling point within the preferred range for the invention, although smaller or larger chain fluorinated ethers may also be employed in appropriate circumstances. Preferred fluorinated ethers for use in the present invention include, for example, perfluorotetrahydropyran, perfluoromethyltetrahydrofuran, perfluorobutylmethyl ether (e.g., perfluoro t-butylmethyl ether, perfluoro isobutyl methyl ether, perfluoro n-butyl methyl ether), perfluoropropylethyl ether (e.g., perfluoro isopropyl ethyl ether, perfluoro n-propyl ethyl ether), perfluorocyclobutylmethyl ether, perfluorocyclopropyl ethyl ether, perfluoropropylmethyl ether (e.g., perfluoro isopropyl methyl ether, perfluoro n-propyl methyl ether), perfluorodiethyl ether, perfluorocyclopropylmethyl ether, perfluoromethylethyl ether and perfluorodimethyl ether.

Other preferred fluoroether compounds contain between 4 and 6 carbon atoms, and optionally contain one halide ion, preferably $Br^{1-}$. For example, compounds having the structure $C_nF_yH_xOBr$, where n is an integer of from 1 to about 6, y is an integer of from 0 to about 13, and x is an integer of from 0 to about 13, are useful as gaseous precursors. Examples of useful gaseous precursors having this formula include perfluoropropyloxylbromide and 2-bromooxyperfluoropropane.

Another preferable gas is sulfur hexafluoride. Yet another preferable gas is heptafluoropropane, including 1,1,1,2,3,3,3-heptafluoropropane and its isomer, 1,1,2,2,3,3,3-heptafluoropropane. Other compounds that may be used as gaseous precursors in the present invention include compounds comprising a sulfur atom, including compounds of the formula $CF_3$—$(CF_2)_n$—$SF_5$ or $SF_5$—$(CF_2)_n$—$SF_5$, where n is an integer of from 1 to about 10. Mixtures of different types of gases, such as mixtures of a perfluorocarbon or a perfluoro ether and another type of gas, such as, for example, air or nitrogen, can also be used in the compositions of the present invention. Other gases, including the gases exemplified above, would be apparent to one skilled in the art in view of the present disclosure.

Other gaseous precursors which are suitable for use in stabilizing materials and compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof Carbonic acid ($H_2CO_3$) is an example of a suitable inorganic acid, and aminomalonic acid is an example of a suitable organic acid. Other acids, including inorganic and organic acids, would be apparent to one skilled in the art in view of the present disclosure.

Gaseous precursors derived from salts are preferably selected from the group consisting of alkali metal salts, ammonium salts and mixtures thereof More preferably, the salt is selected from the group consisting of carbonate, bicarbonate, sesquecarbonate, aminomalonate and mixtures thereof Suitable gaseous precursor materials which are derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, 9(3):525–532 (1970); Fitzpatrick et al., *Inorganic Chemistry*, 13(3):568–574 (1974); and Stelmashok et al., *Koordinatsionnaya Khimiya*, 3(4):524–527 (1977). The disclosures of each of these publications are hereby incorporated herein by reference in their entirety.

The gaseous precursor materials may be also photoactivated materials, such as a diazonium ion and aminomalonate. As discussed more fully hereinafter, certain stabilizing materials and/or vesicles, particularly vesicles, may be formulated so that gas is formed at the target tissue or by the action of sound on the stabilizing materials. Examples of gaseous precursors are described, for example, in U.S. Pat. Nos. 5,088,499 and 5,149,319, the disclosures of each of which are hereby incorporated herein by reference in their entirety. Other gaseous precursors, in addition to those exemplified above, will be apparent to one skilled in the art in view of the present disclosure.

The gases and/or gaseous precursors are preferably incorporated in the stabilizing materials and/or compositions irrespective of the physical nature of the composition. Thus, the gases and/or gaseous precursors may be incorporated, for example, in stabilizing materials in which the stabilizing materials are aggregated randomly, such as emulsions, dispersions or suspensions, as well as in vesicles, including vesicles such as cochleates, micelles and liposomes. Incorporation of the gases and/or gaseous precursors in the stabilizing materials and/or compositions may be achieved by using any of a number of methods. For example, gas filled compositions can be produced by shaking or otherwise agitating an aqueous mixture which comprises a gas and/or gaseous precursor and one or more lipids. This promotes the formation of stabilized compositions within which the gas and/or gaseous precursor is encapsulated.

In addition, a gas may be bubbled directly into an aqueous mixture of stabilizing materials and/or vesicle-forming compounds. Alternatively, a gas instillation method can be used as disclosed, for example, in U.S. Pat. Nos. 5,352,435 and 5,228,446, the disclosures of each of which are hereby incorporated herein by reference in their entirety. Suitable methods for incorporating the gas and/or gaseous precursor in cationic lipid compositions are disclosed also in U.S. Pat. No. 4,865,836, the disclosure of which is hereby incorporated herein by reference in its entirety. Other methods would be apparent to one skilled in the art based on the present disclosure. Preferably, the gas may be instilled in the stabilizing materials and/or other compositions after or during the addition of the stabilizing material and/or during formation of vesicles.

It is preferred that the stabilizing materials, and especially the vesicles, be formulated from lipids and optional stabilizing compounds to promote the formation of stable vesicles, as discussed above. Additionally, it is preferred that the stabilizing materials and/or vesicles comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

Compositions employed herein may also include, with respect to their preparation, formation and use, gaseous precursors that can be activated to change from a liquid or solid into a gas by temperature, pH, light, and energy (such as ultrasound). The gaseous precursors may be made into gas by storing the precursors at reduced pressure. For example, a vial stored under reduced pressure may create a headspace of perfluoropentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified droplets that would be required to form a vesicle of a maximum size of 10 μm.

TABLE 1

Physical Characteristics of Gaseous Precursors and
Diameter of Emulsified Droplet to Form a 10 μm Vesicle

| Compound | Molecular Weight | Boiling Point (° C.) | Density | Diameter (μm) of emulsified droplet to make 10 μm vesicle |
|---|---|---|---|---|
| perfluoropentane | 288.04 | 28.5 | 1.7326 | 2.9 |
| 1-fluorobutane | 76.11 | 32.5 | 0.67789 | 1.2 |
| 2-methyl butane | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluorocyclobutane | 200.04 | −5.8 | 1.48 | 2.8 |
| decafluorobutane | 238.04 | −2 | 1.517 | 3.0 |
| hexafluoroethane | 138.01 | −78.1 | 1.607 | 2.7 |

Source: Chemical Rubber Company Handbook of Chemistry and Physics, Robert C. Weast and David R. Lide, eds., CRC Press Inc. Boca Raton Florida (1989–1990)

As noted above, it is preferred to optimize the utility of the stabilizing materials and/or vesicles, especially vesicles formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book*, 1966, Matheson Company Inc. More preferably, the gas entrapped in the vesicle possesses a solubility in water less than that of air; and even more preferably, the gas entrapped in the vesicle possesses a solubility in water less than that of nitrogen.

In the present invention, the lipids are typically prepared in a mixture and the counter ion is added to the mixture at any stage in the preparation of the lipid composition. For example, the counter ion may be added during one or another agitating procedures including, for example, shaking, microemulsification and/or sonication. Preferably, the counter ion is added along with the lipids at the initial stage of the preparation of the composition. Accordingly, in any of the methods described throughout the present disclosure, a counter ion may be used in the preparation of the stabilizing materials, compositions, vesicles, liposomes, gas filled vesicles, gaseous precusor filled vesicles, and the like. Preferably, in the methods described throughout the present disclosure, the counter ion is added along with the lipids at the initial stage of the preparation of the compositions.

One or more bioactive agents may be incorporated into the lipid compositions described herein. The bioactive agent may be added to the mixture of lipids at the initial stage of preparation of the lipid composition, prior to the addition of the counter ion or after the compositions are formed. For example, in the delivery of deoxyribonucleic acid (DNA), preformed compositions, composed of phosphatidic acid, a lipid covalently bonded to a polymer, and calcium, bind DNA to the compositions. Also the DNA can be incorporated into the compositions by adding the DNA to the lipids at the same time as the counter ion is added to the lipid mixture. Relatively small amounts of energy are necessary to produce the particles of very small size under the appropriate conditions (e.g. appropriate concentrations of lipid materials).

A wide variety of bioactive agents may be entrapped in the compositions of the present invention. Suitable bioactive agents include, for example, contrast agents, genetic materials, chemotherapeutics, peptides and nucleic acids. The compositions of the present invention may also be used for stabilizing gas bodies for use in ultrasound and drug delivery. Preferably, the bioactive agent is genetic material, which includes, for example, nucleic acids, RNA and DNA, of either natural or synthetic origin, including recombinant RNA and DNA and antisense RNA and DNA, hammerhead RNA, ribozymes, hammerhead ribozymes, antigene nucleic acids, both single and double stranded RNA and DNA and analogs thereof, ribooligonucleotides, deoxyribooligonucleotides, antisense ribooligonucleotides, and antisense deoxyribooligonucleotides.

Other bioactive agents that may be used in the compositions of the present invention include, for example, LHRH analogs, 5-lipooxygenase inhibitors, immunosuppressants or bronchodilators; especially preferred materials include leuprolide acetate. The LHRH Ac-D-2-Nal-D-4-Cl-Phe-D-3-Pal-Ser-N-MeTyr-D-Lys(Nic)-Leu-Lys(N-Isp)-Pro-D-Ala-NH$_2$ (hereinafter "D-2-Nal"), the 5-lipoxygenase inhibitor N-[3-[5-(4-fluorophenylmethyl)-2-thienyl]-1methyl-2-propynyl]-N-hydroxyurea, the immunosuppressant cyclosporin A, and the adrenergic bronchodilators isoproterenol arid albuterol. (As used herein, the terms "5-lipoxygenase inhibitor" or "5-LO inhibitor" refer to any physiologically active compound capable of affecting leukotriene biosynthesis.)

The compositions of the present invention are also suitable for the administration of a wide variety of peptide and non-peptide bioactive agents. Some examples of peptides which may be incorporated into the compositions are interferons and other macrophage activation factors, such as lymphokines, muramyl dipeptide (MDP), γ-interferon, α-interferon and β-interferon, and related antiviral and tumoricidal agents; opioid peptides and neuropeptides, such as enkaphalins, endorphins and dynorphins, and related analgesics; renin inhibitors including new-generation antihypertensive agents; cholecystokinins (CCK analogs) such as CCK, ceruletide and eledoisin, and related cardiovascular-targeting agents and CNS-targeting agents; leukotrienes and prostaglandins, such as oxytocin, and related anti-inflammatory, oxytocid and abortifacient compounds; erythropoietin and analogs thereof, as well as related haematinics; LHRH analogs, such as leuprolide, buserelin and nafarelin, and related down-regulators of pituitary receptors; parathyroid hormone and other growth hormone analogs; enzymes, such as Dnase, catalase and alpha-1 antitrypsin; immunosuppressants such as cyclosporin; GM-CSF and other immunomodulators; and insulin.

Non-peptides which may be used in the compositions and methods of the present invention include, for example, beta-agonists, such as isoproterenol, albuterol, isoetherine and metoproteronol, and related anti-asthmatics; steroids, such as flunisolide, and similar anti-asthmatics; cholinergic agents, such as cromolyn, and related anti-asthmatics; and 5-lipoxygenase inhibitors, such as zileuton and the hydroxyurea compound described above, and related leukotriene inhibitors.

Bioactive agents that act as antineoplastics and antibiotics may also be delivered using the compositions of the present invention. Among these are included, for example, antibiotics such as p-aminosalicylic acid, isoniazid, capreomycin sulfate cycloserine, ethambutol hydrochloride ethionamide, pyrazinamide, rifampin and streptomycin sulfate, dapsone, chloramphenicol, neomycin, ceflacor, cefadroxil, cephalexin, cephadrine erythromycin, clindamycin, lincomycin, amoxicillin, ampicillin, bacampicillin, carbenicillin, dicloxicillin, cyclacillin, picloxicillin, hetacillin, methicillin, nafcillin, oxacillin, penicillin (G and V), ticarcillin rifampin, tetracycline and amphotericin B; and antitumor drugs such as methotrexate, fluorourcil, adriamycin, mitomycin, ansamitomycin, bleomycin, cystiene arabinoside, arabinosyl adenine, mercaptopolylysine, vincristine, busulfan, chlorambucil, azidothymidine, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase, etoposide (VP-16), interferon α-2a, interferon α-2b, teniposide (VM-26), vinblastine sulfate (VLB), vincristine sulfate, hydroxyurea, procarbazine, and dacarbazine; mitotic inhibitors such as the vinca alkaloids, and steroids such as dexamethasone.

Charged bioactive agents, such as DNA, can be readily incorporated into the compositions through noncovalent interactions, such as ionic or electrostatic interactions, between the charged bioactive agent, the counter ion and the charged lipid. Hydrophobic bioactive agents, such as sterols, can be added to the lipid mixture and then when the counter ion is added this can be employed to incorporate the lipophilic bioactive agent into the core of the noncovalently crosslinked compositions. Bioactive agents, such as peptides, can also be incorporated when they are hydrophobic, neutral or charged. In many cases by using the appropriate lipids, an interaction can be formed between the soluble lipid and peptide or other bioactive agent. For lipophilic drugs, the interaction may be hydrophobic or van der Waals forces. For charged drugs and lipid head groups, the interaction may be electrostatic interactions. When the counter ion is added, the bioactive agent is then generally entrapped within the lipid composition. Additionally, the counter ions themselves may be employed as the therapeutic agents, such as, for example, $Ca^{+2}$ for the treatment of calcium deficiency.

The compositions of the present invention may also comprise a targeting moiety, such as a targeting ligand. Targeting ligands are preferably associated with the compositions covalently or non-covalently. The targeting ligand may be bound, for example, via a covalent or non-covalent bond, to at least one of the lipids in the composition. Preferably, the targeting ligand is bound to the compositions covalently. In the case of lipid compositions which comprise cholesterol, the targeting ligand is preferably bound to the cholesterol substantially only non-covalently, and/or the targeting ligand is bound covalently to a component of the composition, for example, another lipid, such as a phospholipid, other than the cholesterol.

The targeting ligands which are incorporated in the compositions of the present invention are preferably substances which are capable of targeting receptors and/or tissues in vivo and/or in vitro. With respect to the targeting of tissue, the targeting ligands are desirably capable of targeting heart tissue and membranous tissues, including endothelial and epithelial cells. In the case of receptors, the targeting ligands are desirably capable of targeting GPIIbIIIa receptors or lymphocyte receptors, such as T-cells, B-cells or interleukin-2 receptors. Preferred targeting ligands for use in targeting tissues and/or receptors, including the tissues and receptors exemplified above, are selected from the group consisting of proteins, including antibodies, antibody fragments, hormones, hormone analogues, glycoproteins and lectins, peptides, polypeptides, amino acids, sugars, such as saccharides, including monosaccharides and polysaccharides, and carbohydrates, vitamins, steroids, steroid analogs, hormones, cofactors, and genetic material, including nucleosides, nucleotides, nucleotide acid constructs and polynucleotides, with peptides being particularly preferred.

An example of a protein which may be preferred for use as a targeting ligand is Protein A, which is protein that is produced by most strains of *Staphylococcus aureus*. Protein A is commercially available, for example, from Sigma Chemical Co. (St. Louis, Mo.). Protein A may then be used for binding a variety of IgG antibodies. Generally speaking, peptides which are particularly useful as targeting ligands include natural, modified natural, or synthetic peptides that incorporate additional modes of resistance to degradation by vascularly circulating esterases, amidases, or peptidases. A useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization or end-to-side chain cyclization is also useful in inducing stability. In addition, the substitution of an L-amino acid for a D-amino acid in a strategic region of the peptide may offer resistance to biological degradation.

Preferred targeting ligands in the present invention include cell adhesion molecules (CAM), among which are, for example, cytokines, integrins, cadherins, immunoglobulins and selecting, all of which are discussed in detail below.

In connection with the targeting of endothelial cells, suitable targeting ligands include, for example, one or more of the following: growth factors, including, for example, basic fibroblast growth factor (bFGF), acidic fibroblast growth factor (aFGF), transforming growth factor-alpha (TGF-α), transforming growth factor-beta (TGF-β), platelet-derived endothelial cell growth factor (PD-ECGF) vascular endothelial growth factor (VEGF) and human growth factor (HGF); angiogenin; tumor necrosis factors, including tumor necrosis factor-alpha (TNF-α) and tumor necrosis factor-beta (TNF-β), and receptor antibodies and fragments thereof to tumor necrosis factor (TNF) receptor 1 or 2 family, including, for example, TNF-R1, TNF-R2, FAS, TNFR-RP, NGF-R, CD30, CD40, CD27, OX40 and 4-1BB; copper-containing polyribo-nucleotide angiotropin with a molecular weight of about 4,500, as well as low molecular weight non-peptide angiogenic factors, such as 1-butyryl glycerol; the prostaglandins, including, for example, prostaglandin $E_1$ ($PGE_1$) and prostaglandin $E_2$ ($PGE_2$); nicotinamide; adenosine; dipyridamole; dobutamine; hyaluronic acid degradation products, such as, for example, degradation products resulting from hydrolysis of β linkages, including hyalobiuronic acid; angiogenesis inhibitors, including, for example, collagenase inhibitors; minocycline; medroxy-progesterone; chitin chemically modified with 6-O-sulfate and 6-O-carboxy-methyl groups; angiostatic steroids, such as tetrahydrocortisol; and heparin, including fragments of heparin, such as, for example, fragments having a molecular weight of about 6,000, admixed with steroids, such as, for example, cortisone or hydrocortisone; angiogenesis inhibitors, including angioinhibin (AGM-1470—an angiostatic antibiotic); platelet factor 4; protamine; sulfated polysaccharide peptidoglycan complexes derived from the bacterial wall of an Arthobacter species; fungal-derived angiogenesis inhibitors, such as fumagillin derived from *Aspergillus fumigatus*; D-penicillamine; gold thiomalate; thrombospondin; vitamin $D_3$ analogues, including, for example, 1-α, 25-dihydroxyvitamin $D_3$ and a synthetic analogue 22-oxa-1-α, 25-dihydroxy-vitamin $D_3$; interferons, including, for example, α-interferon, β-interferon and γ-interferon; cytokines and cytokine fragments, such as the interleukins, including, for example, interleukin-1 (IL-1), interleukin-2 (IL-2), interleukin-3 (IL-3), interleuikin-4 (IL-4), interleukin-5 (IL-5), interluekin-6 (IL-6), interleukin-7 (IL-7) and interleukin-8 (IL-8); erythropoietin; a 20-mer peptide or smaller for binding to receptor or antagonists to native cytokines; granulocyte macrophage colony stimulating factor (GMCSF); $LTB_4$ leukocyte receptor antagonists; heparin, including low molecular weight fragments of heparin or analogues of heparin; simple sulfated polysaccharides, such as cyclodextrins, including α-cyclodextrin, β-cyclodextrin, and γ-cyclodextrin; tetradecasulfate; transferrin; ferritin; platelet factor 4; protamine; Gly-His-Lys complexed to copper; ceruloplasmin; (12R)-hydroxyeico-satrienoic acid; okadaic acid; lectins; antibodies; CD11a/CD18; and Very Late Activation Integrin-4 (VLA-4).

In another embodiment, small peptides which bind the interluekin-1 (IL-1) receptor may be used. For example, peptides generated by phage display core sequences of QPY have been shown to be essential for peptide binding, including, for example, AF12198, a 15-mer with a core sequence of WYQJY, where J is azetidine; and IL-1 antagonists with $K_d$ $10^{-10}$ to $10^{-12}$M, such as AcPhe-Glu, Trp-Pro-Gly-Trp-Tyr-Gln-Aze-Tyr-Ala-Leu-Pro-Leu-$CONH_2$ or Ac-Phe-Glu-Trp-Pro-Gly-Trp-Tyr-Gln-Aze-Tyr-Ala-Leu-Pro-Leu-.

Endothelial-leukocyte adhesion molecules (ELAM's) are antigens which are expressed by endothelial cells under conditions of stress which then facilitate the migration of the leukocytes across the endothelium lining the vasculature into the surrounding tissues. These same endothelial-leukocyte adhesion molecules may also be advantageously exploited as receptors for targeting of vesicles. These endothelial cell adhesion molecules belong to a family known as selectins in which the known members, such as GMP-140, all participate in endothelial-leukocyte adhesion and include ELAM-1, LAM-1 and the granule membrane protein 140 (GMP-140) also known as platelet activation-dependent granule-external membrane protein (PADGEM), VCAM-1/INCAM-110 (Vascular Adhesion Molecule/Inducible Adhesion Molecule) and ICAM-1 (Intercellular Adhesion Molecule).

The cadherin family of cell adhesion molecules may also be used as targeting iligands, including for example, the E-, N-, and P-cadherins, cadherin-4, cadherin-5, cadherin-6, cadherin-7, cadherin-8, cadherin-9, cadherin-10, and cadherin-11; and most preferably cadherin C-5. Further, antibodies directed to cadherins, such as, for example, the monoclonal antibody Ec6C10, may be used to recognize cadherins expressed locally by specific endothelial cells.

A wide variety of different targeting ligands can be selected to bind to the cytoplasmic domains of the ELAM molecules. Targeting ligands in this regard may include lectins, a wide variety of carbohydrate or sugar moieties, antibodies, antibody fragments, Fab fragments, such as, for example, Fab'2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of techniques known in the art. Targeting ligands derived or modified from human leukocyte origin, such as CD11a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting ligand. VLA-4, derived from human monocytes, may be used to target VCAM-1. Antibodies and other targeting ligands may be employed to target endoglin, which is an endothelial cell proliferation marker. Endoglin is upregulated on endothelial cells in miscellaneous solid tumors. A targeting ligand which may be used to target endoglin is the antibody TEC-11. Thorpe et al, *Breast Cancer Research and Treatment*, 36:237–51 (1995).

Endothelial cell activation in the setting of atherosclerosis is used in this invention to target the compositions to regions of arteriosclerosis including, for example, atherosclerotic plaque. One such target that can be used is the inducible mononuclear leukocyte endothelial adhesion molecule recognized by Rb1/9 as an ATHERO-ELAM. The monoclonal antibodies, H4/18 and H18/7, may be used to target endothelial cell surface antigens which are induced by cytokine mediators. As a preferred embodiment, gas filled compositions are targeted to atherosclerotic plaque to non-invasively detect diseased blood vessels before severe damage has occurred, for example, prior to stroke or myocardial infarction, so that appropriate medical or surgical intervention may be implemented. ATHERO-ELAM is a preferred target and ligands, such as antibodies, peptides, or lectins or combinations thereof may be used to target this cell surface epitope expressed on endothelial cells in the context of atherosclerosis. Alternatively, lipoproteins or lipoprotein fragments derived from low or high density lipoprotein proteins may be used as targeting ligands. Additionally, cholesterol may be used to target the endothelial cells and localize the lipids, vesicles, and the like, to regions of atherosclerotic plaque. In embodiments which involve the use of cholesterol as a targeting ligand, the cholesterol is preferably unmodified (non-derivatized) with other chemical groups, moieties and ligands.

A targeting ligand directed toward thrombotic material in plaque may be used to differentiate between active and inactive regions of atherosclerotic plaque. Active plaques in the process of generating thrombi are more dangerous since they may ultimately occlude a vessel or result in emboli. In this regard, in addition to low molecular weight heparin fragments, other targeting ligands, such as, for example, anti-fibrin antibody, tissue plasminogen activator (t-PA), anti-thrombin antibody and fibrin antibodies directed to platelet activation factions, may be used to target active plaque with evolving clots. Most preferred targeting ligands are those which will target a plasma membrane associated GPIIbIIIa in activated platelets in addition to targeting P-selectin, and an antibody or associated antibody fragment directed to GPIIbIIIa. The present invention is also useful for detecting regions of acute myocardial infarction. By attaching anti-myosin (particularly cardiomyosin) antibody or anti-actin antibodies to the lipids, infarcted myocardium may be detected by the methods of the present invention. For targeting to granulation tissue (healing wounds), many of the above targeting ligands may be useful, The wound healing tripeptide, arginine-glycine-aspartic acid (RGD), may also be used is a targeting ligand in this regard.

As with the endothelial cells discussed above, a wide variety of peptides, proteins and antibodies may be employed as targeting ligands for targeting epithelial cells. Preferably, a peptide, including synthetic, semi-synthetic or naturally-occurring peptides, with high affinity to the epithelial cell target receptor may be selected, with synthetic peptides being more preferred. In connection with these preferred embodiments, peptides having from about 5 to about 15 amino acid residues are preferred. Antibodies may be used as whole antibody or antibody fragments, for example, Fab or Fab'2, either of natural or recombinant origin. The antibodies of natural origin may be of animal or human origin, or may be chimeric (mouse/human). Human recombinant or chimeric antibodies are preferred and fragments are preferred to whole antibody.

Examples of monoclonal antibodies which may be employed as targeting ligands in the present compositions include CALAM 27, which is formed by immunizing BALEI/c mice with whole human squamous cell carcinoma of the tongue and forming hybridomtas by crossing extracted spleen cells with those of an NS1 syngeneic myeloma cell line. Gioanni et al, *Cancer Research*, 47: 4417–4424 (1987). CALAM 27 is directed to surface epitopes of both normal and malignant epithelial cells. Normal lymph nodes generally do not contain cells expressing these epitopes. See *Cancer Research*, 47:4417–4424 (1987). Accordingly, compositions comprising this antibody can be used to target metastases in the lymph nodes. The monoclonal antibody 3C2 may be employed as a targeting ligarld for targeting malignant epithelial cells of serious ovarian carcinoma and endometrioid carcinoma. Another exemplary targeting ligand is Mab 4C7 (see *Cancer Research*, 45:2358–2362 (1985)), which may be used to target mucinous carcinoma, endometriod carcinoma and mesonephroid carcinoma. For targeting squamous cell carcinoma in head and neck cancer, Mab E48 (*Biological Abstract*, Vol. 099 Issue. 066 Ref 082748) may be used as a targeting ligand. For targeting malignant melanoma, the monoclonal antibody 225.28s (*Pathol. Biol.*, 38 (8):866–869 (1990)) may be employed. The monoclonal antibody mAb2E$_1$, which is targeted to EPR-1 (effector cell protease 1), may also be used.

Targeting ligands may be selected for targeting antigens, including antigens associated with breast cancer, such as epidermal growth factor receptor (EGFR), fibroblast growth factor receptor, erbB2/HER-2 and tumor associated carbohydrate antigens (*Cancer*, 74 (3):1006–12 (1994)). CTA 16.88, homologous to cytokeratins 8, 18 and 19, is expressed by most epithelial-derived tumors, including carcinomas of the colon, pancreas, breast, ovary and lung. Thus, antibodies directed to these cytokeratins, such as 16.88 (IgM) and 88BV59 (IgG3k), which recognize different epitopes on CTA 16.88 (*Semin. Nucl. Med.*, 23 (2):165–79 (1993)), may be employed as targeting ligands. For targeting colon cancer, anti-CEA IgG Fab' fragments may be employed as targeting ligands. Chemically conjugated bispecific anti-cell surface antigen, anti-hapten Fab'-Fab antibodies may also be used as targeting ligands. The MG series monoclonal antibodies may be selected for targeting, for example, gastric cancer (*Chin. Med. Sci. J.*, 6 (1):56–59 (1991).

There are a variety of cell surface epitopes on epithelial cells for which targeting ligands may be selected. For example, the protein human papilloma virus (HPV) has been associated with benign and malignant epithelial proliferations in skin and mucosa. Two HPV oncogenic proteins, E6 and E7, may be targeted as these may be expressed in certain epithelial derived cancers, such as cervical carcinoma. See *Curr. Opin. Immunol.*, 6(5):746–54 (1994). Membrane receptors for peptide growth factors (PGF-R), which are involved in cancer cell proliferation, may also be selected as tumor antigens. Anticancer Drugs, 5(4):379–93 (1994). Also, epidermal growth factor (EGF) and interleukin-2 may be targeted with suitable targeting ligands, including peptides, which bind these receptors. Certain melanoma associated antigens (MAA), such as epidermal growth factor receptor (EGFR) and adhesion molecules (*Tumor Biol.*, 15 (4):188–202 (1994)), which are expressed by malignant melanoma cells, can be targeted with the compositions provided herein. The tumor associated antigen FAB-72 on the surface of carcinoma cells may also be selected as a target.

A wide variety of targeting ligands may be selected for targeting myocardial cells. Exemplary targeting ligands include, for example, anticardiomyosin antibody, which may comprise polyclonal antibody, Fab'2 fragments, or be of human origin, anima origin, for example, mouse origin, or of chimeric origin. Additional targeting ligands include dipyridamole; digitalis; nifedipine; apolipoprotein; low density lipoproteins (LDL), including α-LDL, vLDL and methyl LDL; ryanodine; endothelin; complement receptor type 1; IgG Fc; beta 1-adrenergic; dihydropyridine; adenosine; mineralocorticoid; nicotinic acetylcholine and muscarinic acetylcholine; antibodies to the human alpha 1A-adrenergic receptor; bioactive agents, such as drugs, including the alpha 1-antagonist prazosin; antibodies to the anti-beta-receptor; drugs which bind to the anti-beta-receptor; anti-cardiac RyR antibodies; endothelin-1, which is an endothelial cell-derived vasoconstrictor peptide that exerts a potent positive inotropic effect on cardiac tissue (endothelin-1 binds to cardiac sarcolemmal vesicles); monoclonal antibodies which may be generated to the T-cell receptor α-β receptor and thereby employed to generate targeting ligands; the complement inhibitor sCR1; drugs, peptides or antibodies which are generated to the dihydropyridine receptor; monoclonal antibodies directed towards the anti-interleukin-2 receptor may be used as targeting ligands to direct the present compositions to areas of myocardial tissue which express this receptor and which may be up-regulated in conditions of inflammation; cyclosporine for directing similarly the compositions to areas of inflamed myocardial tissue; methylisobutyl isonitrile; lectins which bind to specific sugars on membranes of cardiac myocytes and cardiac endotheli,al cells; adrenomedullin (ADM), which is an endogenous hypotensive and vasorelaxing peptide; atrial natriuretic peptide (ANP); C-type natriuretic peptide (CNP), which is a 22 amino acid peptide of endothelial cell origin and is structurally related to atrial natriuretic peptide but genetically distinct, and possesses vasoactive and antimitogenic activity; vasonatrin peptide (VNP) which is a chimera of atrial natriuretic peptide (ANP) and C-type natriuretic peptide (CNP) and comprises 27 amino acids; thrombin; endothelium-derived relaxing factor (EDRF); neutral endopeptidase 1 (NEP-1); competitive inhibitors to EDRF, including, for example, NG-monomethyl-L-arginine (L-NMMA); potassium channel antagonists, such as charybdotoxin and glibenclamide; antiheart antibodies, which may be identified in patients with idiopathic dilated cardiomyopathy but which preferably do not elicit cytolysis in the myocardium; antibodies directed against the adenine nucleotide translocator, the branched-chain keto acid dehydrogenase or cardiac myosin; specific antagonists for the endothelin-A receptor, which may be referred to as BQ-123; and antibodies to the angiotensin II receptor.

Two of the major antigens of heart sarcolemmal are calcium binding glycoproteins which copurify with the dihydropyridine receptor. Antisera may be raised, including polyclonal or monoclonal antibodies, against purified sarcolemma. These antibodies may also be employed as targeting ligands. Purified fractions of the calcium binding glycoproteins may be isolated from the plasma membranes of the sarcolemma and then used to generate antibodies. ANP, which, as noted above, may be used as a targeting ligand, can be obtained from cultures of human aortic endothelial cells. ANP is generally localized in endothelium, but also may localize to the endothelial or myocardial tissue. ANP may be prepared, for example, using recombinant techniques, as well as by synthesis of the peptide using peptide synthesis techniques well known to one skilled in the art. It is also possible to use an antibody, either polyclonal or monoclonal, directed towards ANP. Similarly, a peptide directed to ANP may be used for targeting endothelial and/or myocardial cells. Both the β and α forms of atrial natriuretic factor may be used as targeting ligands for directing the present compositions to myocardial tissue.

A wide variety of targeting ligands may be employed to direct the present compositions to the GPIIbIIIa receptor. Compositions which are directed to the GPIIbIIIa receptor are highly useful for targeting vascular thromboses or clots, and are useful for diagnosing and treating such clots. Included among such targeting ligands are, for example, peptides, such as Arg-Gly-Asp-Ser (RGDS), Gly-Arg-Gly-Asp-Ser-Pro (GRGDSP), and Gly-Pro-Arg-Pro (GPRP). Pentapeptides containing the sequence Arg-Gly-Asp (RGD) are also useful including, for example, G4120, which is a cyclic peptide containing the amino acid sequence Arg-Gly-Asp (RGD). Also useful are peptides derived from human coagulation Factor XIIIA including, for example, fragments such as NKLIVRRGQSFYVQIDFSRPYDPRRDLF RVEYVIGRYPQENKGTYIPVPIVSELQS GKW-GAKIVEDRSVRLSIQSS PKCIVGKFRMYVAVWT-PYGVLRTSRNP ETDTYILFNPWCEDDAVYLDNEKER EEYVLNDIGVIFYGEVNDIKTRSWSYGQF-R' where R' is —CONH₂ or —NH₂. In addition, peptides which are fragments of the Factor XIIIA fragment, which include in their sequence the sequence NKLIVRRGOSFYVQIDF SRPYDPRRD or DDAVYLDNE KEREEYVLNDIGVIFY-GEVNDIKTRSWSYGQF.

Additional peptides which may be useful as targeting ligands for targeting the GPIIbIIIa receptor include, for example, peptides comprising the tripeptide sequence of arginine-tyrosine-aspartic acid (Arg-Tyr-Asp; also abbreviated RGD), linked from amino-to-carboxy-terminus and which may bind to the GPIIbIIIa binding region on activated platelets. Exemplary of such peptides include, for example, peptides of the general formula $R^1-(X^1)_n$-Arg-Tyr-Asp-$(Y)_o$-$(X^2)_m$-$R^2$, wherein each of $X^1$, $X^2$ and Y may independently be one or more amino acid residues while, in certain cases, it is preferred that Y is other than a serine or alanine residue, and each of m, n and o is independently 0 or 1, provided, in certain cases, that when m is 1, then o is 1, and $R^1$ is a protected or unprotected terminal amino group and $R^2$ is a protected or unprotected terminal carboxy group. In a preferred embodiment, $X^1$ is the peptide Ala-Arg-Arg-Ser-Ser-Pro-Ser-Tyr-Tyr and $X^2$ is the peptide Gly-Ala-Gly-Pro-Tyr-Tyr-Ala-Met-Asp-Tyr. Useful peptides include Arg-Ser-Pro-Ser-Tyr-Tyr-Arg-Tyr-Asp-Gly-Ala-Gly-Pro-Tyr-Tyr-Ala-Met-Asp-Tyr and Ala-Arg-Arg-Ser-Pro-Ser-Tyr-Tyr-Arg-Tyr-Asp-Gly-Ala-Gly-Pro-Tyr-Tyr-Ala-Met-Asp-Tyr.

Synthetic compounds which combine a natural amino acid sequence with synthetic amino acids can also be used as the targeting ligand, such as a fibrinogen receptor antagonist compound which comprises the sequence XX-Gly-Asp, wherein XX is a synthetic α-amino acid containing a linear side chain, such as

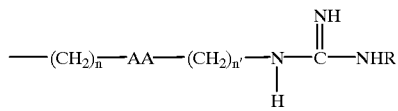

wherein n+n' is 3; AA is a single bond; and R is phenyl or benzyl; or —(CH₂)ₙ—AA—(CH₂)ₙ'—NHR wherein n is an integer of 1 to 4; n' is an integer of 2 to 4; AA is oxygen, sulfur or a single bond; and R is H, $C_{1-6}$ alkyl, optionally substituted aryl, optionally substituted arylmethyl or optionally substituted cycloalkyl, provided, in certain cases, that when AA is a single bond and R is H, then n+n' is other than 3 or 4.

Another such compound comprises a fibrinogen receptor antagonist of the formula:

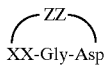

wherein XX is a synthetic α-amino acid containing a linear side chain having the formula

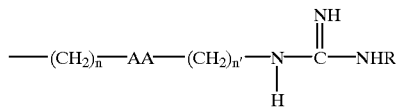

wherein n+n' is 3; AA is a single bond; and R is phenyl or benzyl; or —(CH₂)ₙ—AA—(CH₂)ₙ'—NHR, wherein n is an integer of 1 to 4; n' is an integer of 2 to 4; AA is oxygen, sulfur or a single bond; and R is H, $C_{1-6}$ alkyl, optionally substituted cycloalkyl, provided that, in certain cases, when AA is a single bond and R is H, then n+n' is other than 3 or 4, and ZZ is a sequence of 1 to 4 optionally substituted amino acids.

Other useful peptides for use as targeting ligands include, for example, Elegantin, which has the following sequence: Gly-Glu-Glu-Cys-Asp-Cys-Gly-Ser-Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu- Cys-Cys-Asp-Gln-Cys-Arg-Phe-Lys-R-R'-Arg-Thr-Ile-Cys-Arg-Arg-Ala-Arg-Gly-Asp-Asn-Pro-Asp-Asp-Arg-Cys-Thr-Gly-Gln-Ser-Ala-Asp-Cys-Pro-Arg-Asn-Gly-Tyr, wherein each of R and R' is independently any amino acid; Albolabrin, which has the following sequence: Glu-Ala-Gly-Glu-Asp-Cys-Asp-Cys-Gly-Ser-Pro-Ala-Asn-Pro-Cys- Cys-Asp-Ala-Ala-Thr-Cys-Lys-Leu-Leu-Pro-Gly-Ala-Gln-Cys-Gly-Glu-Gly-Leu-Cys- Cys-Asp-Gln-Cys-Ser-Phe-Met-Lys-Lys-Gly-Thr-Ile-Cys-Arg-Arg-Ala-Arg-Gly-Asp- Asp-Leu-Asp-Asp-Tyr-Cys-Asn-Gly-Ile-Ser-Ala-Gly-Cys-Pro-Arg-Asn-Pro-Leu-His-Ala-Batroxostatin, which has the following sequence: Glu-Ala-Gly-Glu-Glu-Cys-Asp-Cys- Gly-Thr-Pro-Glu-Asn-Pro-Cys-Cys-Asp-Ala-Ala-Thr-Cys-Lys-Leu-Arg-Pro-Gly-Ala-Gln-Cys-Ala-Glu-Gly-Leu-Cys-Cys-Asp-Gln-Cys-Arg-Phe-Lys-Gly-Ala-Gly-Lys-Ile- Cys-Arg-Arg-Ala-Arg-Gly-Asp-Asn-Pro-Asp-Asp-Cys-Thr-Gly-Gln-Ser-Ala-Asp-Cys-Pro-Arg-Phe; and Flavoridin, which has the following sequence: Gly-Gly-Glu-Cys-Asp-Cys-Gly-Ser-Pro-Glu- Asn-Pro-Cys-Cys-Asp-Ala-Ala-Thr-Cys-Lys-Leu-Arg-Pro-Gly- Ala-Gln-Cys-Ala-Asp-Gly-Leu-Cys-Cys-Asp-Gln-Cys-Arg-Phe-Lys-R-R'-Arg-Thr-Ile- Cys-Arg-Ile-Ala-Arg-Gly-Asp-Phe-Pro-Asp-Asp-Arg-Cys-Thr-Gly-Leu-Ser-Ala-Asp-Cys-Pro-Arg-R-Asn-Asp-Leu, wherein each of R and R' is independently any amino acid.

Other ligands useful for targeting the GPIIbIIIa receptor include synthetic compounds, such as Ac-(D)Phe-Pro-boroArg and the cyclic peptidomimetic cyclo(D-2-aminobutyrate-N-Methyl-L-Arginyl-Glycyl-L-Aspartyl-3-amino-methyl-benzoic acid) methanesulfonate salt. Peptides that can also be used include a library of hexapeptides flanked by cysteine residues (capable of forming cyclic disulfides) and cyclic, disulfide-bonded forms of peptides with the sequence Arg-Gly-Asp or Lys-Gly-Asp, as well as the carboxyl-terminal derived peptide, REYVVMWK. Certain matrix glycoproteins such as Thrombospondin are also useful in this regard. Members of the serpin family of serine protease inhibitors, such as Plasminogen activator inhibitor type 1 (PAI-1) are other useful ligands.

Generally, it is preferred to employ, as targeting ligands for the GPIIbIIIa receptor, a peptide having from about 3 to about 20 amino acids, with peptides having from about 4 to about 15 amino acids being more preferred. Even more preferably, targeting ligands for the GPIIbIIIa receptor may comprise peptides having from about 4 to about 8 amino acids, with peptides having from about 4 to about 6 amino acids or about 5 amino acids being still more preferred. If desired, the peptides may be cyclized, for example, by (1) side chain-to-side chain covalent linkages, including, for example, by the formation of a disulfide linkage via the oxidation of two thiol containing amino acids or analogs thereof, including, for example, cysteine or penicillamine; (2) end-to-side chain covalent linkages, including, for example, by the use of the amino terminus of the amino acid sequence and a side chain carboxylate group, such as, for example, a non-critical glutamic acid or aspartic acid group. Alternatively, the end-to-side chain covalent linkage may involve the carboxylate terminus of the amino acid sequence and a side chain amino, amidine, guanidine, or other group in the side chain which contains a nucleophilic nitrogen atom, such side chain groups including, for example, lysine, arginine, homoarginine, homolysine, or the like; (3) end-to-end covalent linkages that are covalent amide linkages, or the like. Such processes are well known to one skilled in the art. In addition, "pseudo-cyclization" may be employed, in which cyclization occurs via non-covalent interactions, such as electrostatic interactions, which induces a folding of the secondary structure to form a type of cyclic moiety. Metal ions may aid the induction of a "pseudocyclic" formation. This type of pseudocyclic formation may be analogous to "zinc fingers." As known to one of ordinary skill in the art, zinc fingers involve the formation due to electrostatic interactions between a zinc ion ($Zn^{2+}$) and cysteine, penicillamine and/or homocysteine, of a region in the shape of a loop (the finger). In the case of homocysteine, the RGD sequence would reside at the tip of the finger. Of course, it is recognized that, in the context of the present invention, any type of stabilizing cyclization would be suitable as long the recognition and binding peptide ligand, such as, for example, RGD, maintains the proper conformation and/or topography to bind to the appropriate receptor in clots with a reasonable Michaelis-Menten constant ($k_m$) or binding constant. As used herein, the term "conformation" refers to the three-dimensional organization of the backbone of the peptide, peptoid, or pseudopeptide, and the term "topography" refers to the three-dimensional organization of the sidechain of the peptide, peptoid, or pseudopeptide.

Other suitable targeting ligands include the following compounds: Ac-Cys-Arg-Gly-Asp-Met-Phe-Gly-Cys-$CONH_2$; Ac-Cys-Arg-Gly-Asp-Met-Leu-Arg-Cys-$CONH_2$; Ac-Cys-Arg-Gly-Asp-Phe-Leu-Asn-Cys-$CONH_2$; Ac-Cys-Asn-Thr-Leu-Lys-Gly-Asp- Cys-$CONH_2$; Ac-Cys-Asn-Trp-Lys-Arg-Gly-Asp-Cys-$CONH_2$; and Ac-Cys-N-methyl-Arg-Gly-Asp-Pen-$CONH_2$, where "Pen" refers to penicillamine (β,β-dimethylcysteine).

Other compounds which may be used as targeting ligands include peptides, or derivatives thereof, represented by the formula

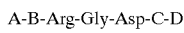

wherein A is proline, thioproline, hydroxyproline, dehydroproline, 2-oxo-4-thiazolidine carboxylic acid, N-alkyl glycine or an amino acid derivative of the formula

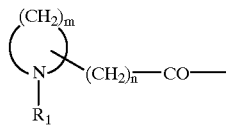

tryptophan, or a tryptophan derivative of the formula

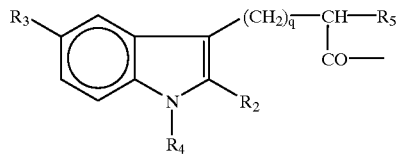

pyroglutamic acid or 2-azetidinone-4-carboxylic acid

B is serine, glycine, valine, alanine, threonine or β-alanine; C is an amino acid group having a hydrophobic functional group; and D is hydroxy or amino; wherein $R_1$ is hydrogen, —$(CH_2)_pCH_3$ or —CO—$(CH_2)_pCH_3$; $R_2$ is hydrogen or alkyl; $R_3$ is hydrogen or alkoxy; $R_4$ is hydrogen or alky; $R_5$ is hydrogen, amino or acylamino; m is an integer of 2 to 5; n is an integer of 0 to 2; p is an integer of 0 to 5; and q is an integer of 0 to 3.

Another targeting ligand which may be suitable for use in connection with the present compositions is a peptide, a peptide derivative, or a salt thereof having the formula

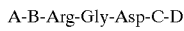

where A is arotic acid or hydroorotic acid; B is an amino acid; C is an amino acid having a hydrophobic functional group; and D is hydroxy or amino. In the above compounds, examples of amino acids having hydrophobic functional groups in the definition of "C" are tryptophan and phenylalanine.

Various peptides which would be suitable for use as a targeting ligand in the present invention, especially for targeting GPIIbIIIa, are described, for example, in U.S. Pat. No. 5,498,601 and European Patent Applications: 0 368 486 A2, 0 382 451 A2, and 0 422 938 B1, the disclosures of which are hereby incorporated herein by reference in their entirety. Other targeting ligands which may be used in the compositions of the present invention, in addition to those exemplified above, would be apparent to one of ordinary skill in the art in view of the present disclosure. Other suitable targeting ligands include, for example, conjugated peptides, such as, for example, glycoconjugates and lectins, which are peptides attached to sugar moieties. The compositions may comprise a single targeting ligand, as well as two or more different targeting ligands.

The targeting ligand is preferably covalently bound to the surface of the composition by a spacer including, for example, hydrophilic polymers, preferably polyethylene glycol. Preferred molecular weights of the polymers are from 1000 da to 10,000 da, with 500 da being most preferred. Preferably the polymer is bifunctional with the targeting ligand bound to a terminus of the polymer. Generally, the targeting ligand will range from about 0.1 to about 20 mole % of the exterior components of the vesicle. In the case of gas-filled lipid vesicles, this amount is preferably between about 0.5 and about 10 mole % with about 1 to about 10 mole % most preferred. The exact ratio will depend upon the particular targeting ligand.

In another embodiment, the targeting ligands are directed to lymphocytes which may be T-cells or B-cells, with T-cells being the preferred target. Depending on the targeting ligand, the composition may be targeted to one or more classes or clones of T-cells. To select a class of targeted lymphocytes, a targeting ligand having specific affinity for that class is employed. For example, an anti CD-4 antibody can be used for selecting the class of T-cells harboring CD-4 receptors, an anti CD-8 antibody can be used for selecting the class of T-cells harboring CD-8 receptors, an anti CD-34 antibody can be used for selecting the class of T-cells harboring CD-34 receptors, etc. A lower molecular weight ligand is preferably employed, e.g., Fab or a peptide fragment. For example, an OKT3 antibody or OKT3 antibody fragment may be used. When a receptor for a class of T-cells or clones of T-cells is selected, the composition will be delivered to that class of cells. Using HLA-derived peptides, for example, will allow selection of targeted clones of cells expressing reactivity to HLA proteins.

The ultimate purpose of the linkage between the targeting ligand and the target may be the delivery of the composition to the cell for endocytosis or fusion. Although not intending to be bound by any particular theory of operation, once the composition has linked to its target, the composition may gain access to the interior of the target cell either through a fusion-initiated capping and patching mechanism, the intervention of clathrin-coated pits or through classical endocytosis, depending on the mechanisms for engulfment peculiar to the target cell, or by other natural or induced means. One skilled in the art will recognize the potential for targeted uses of bioactive agents which gain access to the target cells or tissue via ligand-receptor binding.

The following tables illustrate ligands from the major histocompatability complex (MHC) and their receptors in the class of T-cells for which they have affinity. All the ligands, T-cell receptors and peptide sequences in the table below may be used in the present invention.

TABLE 2

MHC LIGANDS AND T-CELL RECEPTORS

| T-Cell Receptor | Ligand | Peptide Sequence |
|---|---|---|
| HTB157.7 | $K^b$(Q10b hybrid) | Heterogeneous |
| HTB157.7 | $pK^b$163–174 | NA |
| 2C | $L^d$/p2Ca | LSPFPFDL* |
| 2C | $L^d$/p2Ca-A5 | LSPFAFDL |
| 2C | $L^d$/p2Ca-A3 | LSAFPFDL |
| 2C | $L^d$/p2Ca-A8 | LSPFPFDA |
| 2C | $L^d$/SL9 | SPFPFDLLL |
| 2C | $K^b$/p2Ca | LSPFPFDL |

TABLE 2-continued

MHC LIGANDS AND T-CELL RECEPTORS

| T-Cell Receptor | Ligand | Peptide Sequence |
|---|---|---|
| 2C | $L^d$/QL9 | QLSPSPDL |
| 4G3 | $K^b$/pOV8 | SIINFEKL |
| 2C | $L^d$/p2Ca-Y4 | LSPYPFDL |
| 2C | $L^d$/p2Ca-A1 | ASPFPFDL |
| Clone 30 | $K^b$/IgG (bivalent) | Heterogeneous |
| 14.3d | 1-$E^d$/pHA | SSFGAFGIFPK |
| 5C.C7 | 1-$E^k$/MCC | ANERADLIAYLKQATK |
| 228.4 | 1-$E^k$/MCC-K99A | ANERADLIAYLKQATK |
| 2B4 | 1-$E^k$/MCC | ANERADLIAYLKQATK |
| 2B4 | 1-$E^k$/PCC | ANERADLIAYLKQATAK |
| 2B4 | 1-$E^k$/MCC-T102S | ANERADLIAYLKQASK |
| HA1.7 | SEB | |
| 14.3d β | SEC1 | |
| 14.3d β | SEC2 | |
| 14.3d β | SEC3 | |
| 14.3d β | SEB | |
| 14.3d β | SPEA | |

*Single-letter code for amino acids. Summarized from Fremont et al, Current Opinion In Immunology, (1996) 8:93–100, page 96, Table 2, the disclosure of which is hereby incorporated herein by reference in its entirety.

Another major area for targeted delivery involves the interlekin-2 (IL-2) system. L-2 is a t-cell growth factor produced following antigen or mitogen induced stimulation of lymphoid cells. Among the cell types which produce IL-2 are $CD4^+$ and $CD8^+$ t-cells and large granular lymphocytes, as well as certain t-cell tumors. IL-2 receptors are glycoproteins expressed on responsive cells. They are notable in connection with the present invention because they are readily endocytosed into lysosomal inclusions when bound to IL-2. The ultimate effect of this endocytosis depends on the target cell, but among the notable in vivo effects are regression of transplantable murine tumors, human melanoma or renal cell cancer. IL-2 has also been implicated in antibacterial and antiviral therapies and plays a role in allograft rejection. In addition to IL-2 receptors, preferred targets include the anti-IL-2 receptor antibody, natural IL-2 and an IL-2 fragment of a 20-mer peptide or smaller generated by phage display which binds to the IL-2 receptor.

Although not intending to be bound by any particular theory of operation, IL-2 can be conjugated to the compositions and thus mediate the targeting of cells bearing IL-2 receptors. Endocytosis of the ligand-receptor complex would then deliver the composition to the targeted cell, thereby inducing its death through apoptosis—independent and superceding any proliferative or activiating effect which IL-2 would promote alone.

Additionally, an IL-2 peptide fragment which has binding affinity for IL-2 receptors can be incorporated either by direct attachment to a reactive moiety on the composition or via a spacer or linker molecule with a reactive end such as an amine, hydroxyl, or carboxylic acid functional group. Such linkers are well known in the art and may comprise from 3 to 20 amino acid residues. Alternatively, D-amino acids or derivatized amino acids may be used which avoid proteolysis in the target tissue.

Still other systems which can be used in the present invention include IgM-mediated endocytosis in B-cells or a variant of the ligand-receptor interactions described above wherein the T-cell receptor is CD2 and the ligand is lymphocyte function-associated antigen 3 (LFA-3), as described, for example, by Wallner et al, *J. Experimental Med.*, 166:923–932 (1987), the disclosure of which is hereby incorporated by reference herein in its entirety.

The targeting ligand may be incorporated in the present compositions in a variety of ways. Generally speaking, the targeting ligand may be incorporated in the present compositions by being associated covalently or non-covalently with one or more of the lipids which are included in the compositions.

Exemplary covalent bonds by which the targeting ligands are associated with the compositions include, for example, amide (—CONH—); thioamide (—CSNH—); ether (ROR'), where R and R' may be the same or different and are other than hydrogen); ester (—COO—); thioester (—COS—); —O—; —S—; —$S_n$—, where n is greater than 1, preferably about 2 to about 8, and more preferably about 2; carbamates; —NH—; —NR—, where R is alkyl, for example, alkyl of from 1 to about 4 carbons; urethane; and substituted imidate; and combinations of two or more of these. Covalent bonds between targeting ligands and lipids may be achieved through the use of molecules that may act as spacers to increase the conformational and topographical flexibility of the ligand. Examples of such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like. In addition, in the case of targeting ligands which comprise peptide moieties, side chain-to-side chain crosslinking may be complemented with side chain-to-end crosslinking and/or end-to-end crosslinking. Also, small spacer molecules, such as dimethylsuberimidate, may be used to accomplish similar objectives. The use of agents, including those used in Schiffs base-type reactions, such as gluteraldehyde, may also be employed. The Schiffs base linkages, which may be reversible linkages, can be rendered more permanent covalent linkages via the use of reductive amination procedures. This may involve, for example, chemical reducing agents, such as lithium aluminum hydride reducing agents or their milder analogs, including lithium aluminum diisobutyl hydride (DIBAL), sodium borohydride ($NaBH_4$) or sodium cyanoborohydride ($NaBH_3CN$).

The covalent linking of the targeting ligands to the present compositions may be accomplished using synthetic organic techniques which would be readily apparent to one of ordinary skill in the art in view of the present disclosure. For example, the targeting ligands may be linked to the materials, including the lipids, via the use of well known coupling or activation agents. As known to the skilled artisan, activating agents are generally electrophilic, which can be employed to elicit the formation of a covalent bond. Exemplary activating agents which may be used include, for example, carbonyldiimidazole (CDI), dicyclohexylcarbodiimide (DCC), diisopropylcarbodiimide (DIC), methyl sulfonyl chloride, Castro's Reagent, and diphenyl phosphoryl chloride.

The covalent bonds may involve crosslinking and/or polymerization. Cross-linking preferably refers to the attachment of two chains of polymer molecules by bridges, composed of either an element, a group, or a compound, which join certain carbon atoms of the chains by covalent chemical bonds. For example, crosslinking may occur in polypeptides which are joined by the disulfide bonds of the cystine residue. Crosslinking may be achieved, for example, by (1) adding a chemical substance (crosslinking agent) and exposing the mixture to heat, or (2) subjecting a polymer to high energy radiation. A variety of crosslinking agents, or "tethers", of different lengths and/or functionalities are described, for example, by Lunbland, *Techniques in Protein Modification*, CRC Press, Inc., Ann Arbor, Mich., pp. 249–68 (1995), the disclosures of which is hereby incorporated herein by reference in its entirety. Exemplary crosslinkers include, for example, 3,3'-dithiobis (succinimidylpropionate), dimethyl suberimidate, and its variations thereof, based on hydrocarbon length, and bis-N-maleimido-1,8-octane.

The targeting ligands may be linked or attached to the compositions of the present invention via a linking group. A variety of linking groups are available and would be apparent to one skilled in the art in view of the present disclosure. Preferably, the linking group comprises a hydrophilic polymer. Suitable hydrophilic polymers include, for example, polyalkyleneoxides such as, for example, polyethylene glycol (PEG) and polypropylene glycol (PPG), polyvinylpyrrolidones, polyvinylmethylethers, polyacrylamides, such as, for example, polymethacrylamides, polydimethylacrylamides and polyhydroxypropylmethacrylamides, polyhydroxyethyl acrylates, polyhydroxypropyl methacrylates, polyalkyloxazolines, such as polymethyloxazolines and polyethyloxazolines, polyhydroxyalkyloxazolines, such as polyhydroxyethyloxazolines, polyhyhydroxypropyloxazolines, polyvinyl alcohols, polyphosphazenes, poly(hydroxyalkylcarboxylic acids), polyoxazolidines, polyaspartamide, and polymers of sialic acid (polysialics). The hydrophilic polymers are preferably selected from the group consisting of PEG, PPG, polyvinylalcohol and polyvinylpyrrolidone and copolymers thereof, with PEG and PPG polymers being more preferred and PEG polymers being even more prefered. Thus, in embodiments involving lipid compositions which comprise lipids bearing polymers including, for example, DPPE-PEG, the targeting ligand may be linked directly to the polymer which is attached to the lipid to provide, for example, a conjugate of DPPE-PEG-TL, where TL is a targeting ligand. Thus, using the example DPPE-PEG, such as, for example, DPPE-PEG5000, the aforementioned conjugate may be represented as DPPE-PEG5000-TL. The hydrophilic polymer used as a linking group is preferably a bifunctional polymer, for example, bifunctional PEG, such as diamino-PEG. In this case, one end of the PEG group is linked, for example, to a lipid compound, and is bound at the free end to the targeting ligand via an amide linkage. A hydrophilic polymer, for example, PEG, substituted with a terminal carboxylate group on one end and a terminal amino group on the other end, may also be used. These latter bifunctional hydrophilic polymer may be preferred since they possess various similarities to amino acids.

Standard peptide methodology may be used to link the targeting ligand to the lipid when utilizing linker groups having two unique terminal functional groups. Bifunctional hydrophilic polymers, and especially bifunctional PEGs, may be synthesized using standard organic synthetic methodologies. In addition, many of these materials are available commercially, such as, for example, α-amino-ω-carboxy-PEG which is commercially available from Shearwater Polymers (Huntsville, Ala.). An advantage of using a PEG material as the linking group is that the size of the PEG can be varied such that the number of monomeric subunits of ethylene glycol may be as few as, for example, about 5, or as many as, for example, about 500 or more. Accordingly, the "tether" or length of the linkage may be varied, as desired. This may be important depending, for example, on the particular targeting ligand employed. For example, a targeting ligand which comprises a large protein molecule may require a short tether, such that it will simulate a membrane bound protein. A short tether would also allow for a vesicle to maintain a close proximity to the cell. This can be used advantageously in connection with vesicles which also comprise a bioactive agent in that the concentration of bioactive agent which is delivered to the cell may be advantageously increased.

Another suitable linking group which may provide a short tether is glyceraldehyde. Glyceraldehyde may be bound, for example, to DPPE via a Schiff's base reaction. Subsequent Amadori rearrangement can provide a substantially short linking group. The β carbonyl of the Schiff's base may then react with a lysine or arginine of the targeting protein or peptide to form the targeted lipid.

More specifically, the compositions of the present invention may contain various functional groups, such as, for example, hydroxy, thio and amine groups, which can react with a carboxylic acid or carboxylic acid derivative of the hydrophilic polymeric linker using suitable coupling conditions which would be apparent to one of ordinary skill in the art in view of the present disclosure. After the carboxylic acid group (or derivative thereof) reacts with the functional group, for example, hydroxy, thio or amine group to form an ester, thioester or amide group, any protected functional group may be deprotected utilizing procedures which would be well known to one skilled in the art. The term protecting group refers to any moiety which may be used to block the reaction of a functional group and which may be removed, as desired, to afford the unprotected functional group. Any of a variety of protecting groups may be employed and these will vary depending, for example, as to whether the group to be protected is an amine, hydroxyl or carboxyl moiety. If the functional group is a hydroxyl group, suitable protecting groups include, for example, certain ethers, esters and carbonates. Such protecting groups are described, for example, in Greene, TW and Wuts, PGM "Protective Groups in Organic Synthesis" John Wiley, New York, 2nd Edition (1991), the disclosure of which is hereby incorporated herein by reference in its entirety. Protecting groups for amine groups include, for example, t-butyloxycarbony (Boc), allyloxycarbonyl (Alloc), benzyloxycarbonyl(Cbz), o-nitrobenzyloxycarbonyl and and trifluoroacetate (TFA).

Amine groups which may be present, for example, on a backbone of a polymer which is included in the vesicles, may be coupled to amine groups on a hydrophilic polymer by forming a Schiff s base, for example, by using coupling agents, such as glutaraldehyde. An example of this coupling is described by Allcock et al, *Macromolecules*, 19(6):1502–1508 (1986), the disclosure of which is hereby incorporated herein by reference in its entirety. If, for example, vesicles are formulated from polylysine, free amino groups may be exposed on the surface of the vesicles, and these free amine groups may be activated as described above. The activated amine groups can be used, in turn, to couple to a functionalized hydrophilic polymer, such as, for example, α-amino-ω-hydroxy-PEG in which the ω-hydroxy group has been protected with a carbonate group. After the reaction is completed, the carbonate group can be cleaved, thereby enabling the terminal hydroxy group to be activated for reaction to a suitable targeting ligand. In certain embodiments, the surface of a vesicle may be activated, for example, by displacing chlorine atoms in chlorine-containing phosphazene residues, such as polydichlorophosphazene. Subsequent addition of a targeting ligand and quenching of the remaining chloride groups with water or aqueous methanol will yield the coupled product.

In addition, poly(diphenoxyphosphazene) can be synthesized (Allcock et al., *Macromolecules*, 19(6):1502–1508 (1986)) and immobilized, for example, on DPPE, followed by nitration of the phenoxy moieties by the addition of a mixture of nitric acid and acetic anhydride. The subsequent nitro groups may then be activated, for example, by (1) treatment with cyanogen bromide in 0.1 M phosphate buffer (pH 11), followed by addition of a targeting ligand containing a free amino moiety to generate a coupled urea analog, (2) formation of a diazonium salt using sodium nitrite/HCl, followed by addition of the targeting ligand to form a coupled ligand, and/or (3) the use of a dialdehyde, for example, glutaraldehyde as described above, to form a Schiff's base. After linking the DPPE to the hydrophilic polymer and the targeting ligand, the vesicles may be formulated utilizing the procedures described herein.

Aldehyde groups on polymers can be coupled with amines as described above by forming a Schiff's base. An example of this coupling procedure is described in Allcock and Austin, *Macromolecules*, 14:1616 (1981), the disclosure of which is hereby incorporated herein by reference in its entirety.

In the above procedures, the polymer or terminus of the lipid, for example, phosphatidylglycerol or phosphatidylethanolamine, is preferably activated and coupled to the hydrophilic polymeric linker, the terminus of which has been blocked in a suitable manner. As an example of this strategy, α-amino-ω-carboxy-PEG4000 having a t-Boc protected terminal amino group and a free carboxylate end, may be activated with 1,1'-carbonyl-diimidazole in the presence of hydroxybenzotriazole in N-methylpyrollidone. After the addition of phosphatidylethanolamine, the t-Boc group may be removed by using trifluoro-acetic acid (TFA), leaving the free amine. The amine may then be reacted with a targeting ligand which may comprise, for example, a peptide, protein, alkaloid, or other moiety, by similar activation of the ligand, to provide the lipid-linker-targeting ligand conjugate. Other strategies, in addition to those exemplified above, may be utilized to prepare the lipid-linker-targeting ligand conjugates. Generally speaking, these methods employ synthetic strategies which are generally known to one skilled in the art of synthetic organic chemistry.

As known to one of ordinary skill in the art, immunoglobulins typically comprise a flexible region which is identified as the "hinge" region. See, e.g., "Concise Encyclopedia of Biochemistry", Second Edition, Walter de Gruyter & Co., pp. 282–283 (1988). Fab' fragments can be linked to the present compositions using the well-defined sites of the thiols of the hinge region. This is a preferred region for coupling Fab' fragments as the potential binding site is remote from the antigen-recognition site. Generally, it may be difficult to utilize the thiols of the hinge group unless they are adequately prepared. In particular, as outlined by Shahinian and Salvias (*Biochimica et Biophysica Acta*, 1239:157–167 (1995)) it may be important to reduce the thiol group so that they are available for coupling, for example, to maleimide derivatized linking groups. Examples of reducing agents commonly used are ethanedithiol, mercaptoethanol, mercaptoethylamine or the more commonly used dithiothreitol, commonly referred to as Cleland's reagent. However, it should be noted that care should be exercised when utilizing certain reducing agents, such as dithiothreitol, as over-reduction may result. Discriminating use of reducing agents may be necessary in connection with proteins whose activity or binding capacity may be compromised due to overreduction and subsequent denaturation or conformational change. See, Shahinian et al, *Biochim. Biophys. Acta*, 1239:157–167 (1995), the disclosure of which is hereby incorporated herein by reference in its entirety.

F(ab')$_2$ antibody fragments may be prepared by incubating the antibodies with pepsin (60 μg/ml) in 0.1 M sodium acetate (pH 4.2) for 4 h at 37° C. Digestion may be terminated by adding 2 M Tris (pH 8.8) to a final concentration of 80 mM. The F(ab')$_2$ fragments may then be obtained by centrifugation (10,000×g. 30 min. 4° C.). The supernatant may then be dialyzed at 4° C. against 150 mM NaCl, 20 mM phosphate at pH 7.0. This then may be chromatographed on a column of Protein A-Sepharose CL-4B to remove any undigested IgG. The Fab' fragments may then be prepared by extensively degassing the solutions and purging with nitrogen prior to use. The F(ab')$_2$ fragments may be provided at a concentration of 5 mg/ml and reduced under argon ink 30 mM cysteine. Alternatively, cysteamine may be employed. 100 mM Tris, pH 7.6 may be used as a buffer for 15 min at 37° C. The solutions may then be diluted 2-fold with an equal volume of the appropriate experimental buffer and spun through a 0.4 ml spin column of Bio-Gel P-6DG. The resulting Fab' fragments may be more efficient in their coupling to maleimide linkers. Note also that the same procedure may be employed with other macromolecules containing cysteine residues for coupling, for example, to the maleimide spacers. Also, peptides may be utilized provided that they contain a cysteine residue. If the peptides have not been made fresh and there is a possibility of oxidation of cysteine residues within the peptide structure, it may be necessary to regenerate the thiol group using the approach outlined above.

Additional linkers would include other derivatives of lipids useful for coupling to a bifunctional spacer. For example, phosphatidylethanolamine (PE) may be coupled to a bifunctional agent. For example N-succinimidyl 4-(p-maleimidophenyl)-butyrate (SMPB) and N-succinimidyl 3-(2-pyridyldithiol) propionate (SPDP), N-succinimidyl trans-4-(N-maleimidylmethyl)cyclohexane-1-carboxylate (SMCC), and N-succinimidyl 3-maleimidyl-benzoate (SMB) may be used among others, to produce, for example the functionalized lipids MPB-PE and PDP-PE.

The free end of the hydrophilic spacer, such as polyethylene glycol ethylamine, which contains a reactive group, such as an amine or hydroxyl group, could be used to bind a cofactor or other targeting ligand. For example, polyethylene glycol ethylamine may be reacted with N-succinimidylbiotin or p-nitrophenylbiotin to introduce onto the spacer a useful coupling group. For example, biotin may be coupled to the spacer and this will readily bind non-covalently proteins. As an example, MPB-PEG-DPPE may be synthesized as follows. DPPE-PEG with a free amino group at the terminus of the PEG will be provided as described previously. Synthesis of the SMPB:PEG-DPPE may then be carried out with 1 equivalent of triethylamine in chloroform at a molar ratio of 1:5 SMPB:DPPE-PEG. After 3 hours, the reaction mixture will be evaporated to dryness under argon. Excess unreacted SMPB and major by products will be removed by preparative thin layer chromatography (TLC, silica gel developed with 50% acetone in chloroform). The upper portion of the lipid band can be extracted from the silica with about 20–30% methanol in chloroform (V:V) resulting in the isolation of pure intact MPB-Peg-DPPE. Streptavidin may then be coupled to proteins so that the proteins in turn may then be coupled to the MPB-PEG-DPPE. Briefly SPDP would be incubated with streptavidin at room temperature for 30 minutes and chromatography employed to remove unreacted SPDP. Dithiothreitol (DTT) was added to the reaction mixture and 10 minutes later 2-thiopyridone at a concentration of 343 nM. The remainder of the reaction mixture is reduced with DTT (25 mM for 10 min.). The thiolated product is isolated by gel exclusion. The resulting streptavidin labeled proteins may then be used to bind to the biotinylated spacers affixed to the lipid moieties.

In preferred embodiments, the targeted compositions may be used to form targeted emulsions and/or targeted vesicles, including, for example, targeted cochleates, targeted emulsions, targeted micelles, and/or targeted liposomes. The targeting ligand which is attached to the compositions from which the vesicles are prepared may be directed, for example, outwardly from the surface of the vesicle. Thus, there is provided a targeted vesicle which can be used to target receptors and. tissues.

In certain embodiments, the targeting ligands may be incorporated in the present compositions via non-covalent associations. As known to one skilled in the art, non-covalent association is generally a function of a variety of factors, including, for example, the polarity of the involved molecules, the charge (positive or negative), if any, of the involved molecules, the extent of hydrogen bonding through the molecular network, and the like. Non-covalent interactions may be employed to bind the targeting ligand to the lipid, or directly to the surface of a vesicle. For example, the amino acid sequence Gly-Gly-His may be bound to the surface of a vesicle, preferably by a linker, such as PEG, and copper, iron or vanadyl ion may then be added. Proteins, such as antibodies which contain histidine residues, may then bind to the vesicle via an ionic bridge with the copper ion, as described in U.S. Pat. No. 5,466,467, the disclosure of which is hereby incorporated herein by reference in its entirety. An example of hydrogen bonding involves cardiolipin lipids which can be incorporated into the lipid compositions.

In preferred embodiments of the present invention, which may involve vesicles, changes, for example, in pH and/or temperature in vivo, may be employed to promote a change in location in the targeting ligands, for example, from a location within the vesicle, to a location external to the outer wall of the vesicle. This may promote binding of the targeting ligands to targeting sites, for example, receptors, such as lymphocytes, and tissues, including myocardial, endothelial and epithelial cells, since the targeting ligand has a greater likelihood of exposure to such targeting sites. In addition, high energy ultrasound can be used to promote rupturing of the vesicles. This can also expose the targeting ligand to the desired binding site.

As an example, a targeting ligand incorporated into the compositions of the present invention may be of the formula:

L-P-T wherein L is a lipid, surfactant, bioactive agent or the like; P is a hydrophilic polymer; and T is a targeting ligand.

In a preferred embodiment, L is a lipid selected from the group consisting of lecithins, phosphatidylcholines, phosphatidylserines, phosphatidylinositols, cardiolipins, cholesterols, cholesterolamines, lysophosphatides, erythrosphingosines, sphingomyelins, ceramides, cerebrosides, saturated phospholipids, unsaturated phospholipids, and krill phospholipids. More preferably, L is a lipid is selected from the group consisting of lecithins, phosphatidylcholines, phosphatidylserines and phosphatidylinositols. In other preferred embodiments, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidyl-cholines, lysophosphatidylglycerols, 1,2-diacyl-sn-glycerols, 1,2-diacyl-ethylene glycols, N-(n-caproylamine)-1,2-diacyl-sn-glycero-3-phosphoethanolamines, N-dodecanylamine-1,2-diacyl-sn-glycero-3-phosphoethanol-amines, N-succinyl-1,2-diacyl-sn-glycero-3-phosphoethanolamines, N-glutaryl-1,2-diacyl-sn-glycero-3-phosphoethanolamines and N-dodecanyl-1,2-diacyl-sn-glycero-3-phosphoethanol-amines. More preferably, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidylcholines, lysophosphatidyl-glycerols and 1,2-diacyl-sn-glycerols.

In other preferred embodiments, L is a surfactant, preferably a fluorosurfactant, and more preferably a fluorosurfactant having polyethylene glycol attached thereto.

In the above compounds, P is a hydrophilic polymer. Preferably, P is a hydrophilic polymer selected from the group consisting of polyalkyleneoxides, polyvinyl alcohol, polyvinylpyrrolidones, polyacrylamides, polymethacrylamides, polyphosphazenes, phosphazene, poly(hydroxyalkylcarboxylic acids) and polyoxazolidines. More preferably, P is a polyalkyleneoxide polymer, with polyethylene glycol and polypropylene glycol being even more preferred and polyethylene glycol being particularly preferred.

In the above formula, T is a targeting ligand. Preferably, T is a targeting ligand selected from the group consisting of proteins, peptides, saccharides, steroids, steroid analogs, and genetic material, with proteins, peptides and saccharides being more preferred.

In the case of targeting ligands which comprise saccharide groups, suitable saccharide moieties include, for example, monosaccharides, disaccharides and polysaccharides. Exemplary monosaccharides may have six carbon atoms and these saccharides include allose, altrose, glucose, dextrose, mannose, gulose, idose, galactose, talose, fructose, psicose, verbose and tagatose. Five carbon saccharides include ribose, arabinose, xylose, lyxose, ribulose and xylulose. Four carbon saccharides include erythrose, threose and erythrulose. Disaccharides include sucrose, lactose, maltose, isomaltose and cellobiose. Saccharide bearing targeting lipids may be, synthesized through a multistep organic synthesis approach, as described more fully hereinafter. For example, lipids bearing targeting glucose moieties may be prepared by reacting, for example, α-glucopyranosyl bromide tetrabenzyl with ω-trifluoroacetyl-aminopolyethyleneglycol to obtain ω-glucopyranosyl tetrabenzyl-ω'-trifluoroacetyl-aminopolyethyleneglycol. This may then be hydrolyzed in a sodium carbonate or potassium carbonate solution and then hydrogenated to obtain ω-glucopyranpsyl-ω'amino-polyethyleneglycol. Aminoglyco-pyranosyl terminated polyethyleneglycol may then react with N-DPGS-succinimide to form the lipid bearing saccharide DPGS-NH-PEG-Glucose. In certain embodiments, the targeting ligands target cancer cells or tumor cells.

In another embodiment, the targeting ligand incorporated into the compositions of the present invention may be of the formula:

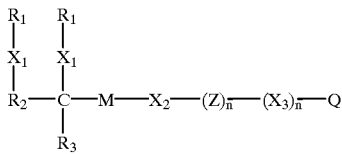

where each $X_1$ is independently —O—, —S—, —SO—, —$SO_2$—, —$NR_4$—, —$X_4$—C(=$X_5$)—, —C(=$X_5$)—$X_4$— or —C(=$X_5$)—; each of $X_2$ and $X_3$ is independently a direct bond, —$R_5$—$X_4$—C(=$X_5$)—, —$R_5$-C(=$X_5$)—$X_4$, —$X_4$—C(=$X_5$)—$R_5$—, —C(=$X_5$)—$X_4$—$R_5$—, —$X_4$—$R_5$—C(=$X_5$)—$X_4$—, —$R_5$—$X_4$—C(=$X_5$)—$R_5$—C(=$X_5$)—$X_4$— or —$R_5$—C(=$X_5$)—$X_4$—$R_5$—$X_4$—C(=$X_5$)—; each $X_4$ is independently —O—, —$NR_4$— or —S—; each $X_5$ is independently O or S; M is —$R_5$—$X_4$—C(=$X_5$)—, —$R_5$—C(=$X_5$)—$X_4$—, —$R_5$—$X_4$—(Y$X_5$)P(=$X_5$)—$X_4$— or —$X_4$—(Y$X_5$)P(=$X_5$)—$X_4$—$R_5$—; each n is, independently, 0 or 1; Y is hydrogen or a pharmaceutically acceptable counter ion; Z is a hydrophilic polymer; Q is a targeting ligand or a precursor to a targeting ligand; each $R_1$ is independently an alkyl group of 1 to about 50 carbons that may optionally be substituted with one or more halogen atoms; each $R_2$ is independently an alkylene group of 1 to about 30 carbons that may optionally be substituted with one or more halogen atoms; each of $R_3$ and $R_4$ is independently hydrogen or alkyl of 1 to about 10 carbons; and each $R_5$ is independently a direct bond or alkylene of 1 to about 30 carbons.

In the above formula, when any symbol appears more than once in a particular formula or substituent, its meaning in each instance is independent of the other. Also in the above formula, it is intended that when each of two or more adjacent symbols is defined as being a "direct bond" to provide multiple, adjacent direct bonds, the multiple and adjacent direct bonds devolve into a single direct bond.

In preferred embodiments, each $X_1$ is independently —$X_4$—C(=$X_5$)—, —C(=$X_5$)—$X_4$— or —C(=$X_5$)—. More preferably, each $X_1$ is independently —$X_4$—C(=$X_5$)— or —C(=$X_5$)—$X_4$—. Even more preferably, $X_1$ is —C(=$X_5$)—$X_4$—, for example, —C(=O)—O—.

In preferred embodiments, each of $X_2$ and $X_3$ is independently a direct bond, —$R_5$—$X_4$—C(=$X_5$)—, —$R_5$—C(=$X_5$)—$X_4$, —$X_4$—C(=$X_5$)—$R_5$—, —C(=$X_5$)—$X_4$—$R_5$—, —$X_4$—$R_5$—C(=$X_5$)—$X_4$— or —$R_5$—$X_4$—C(=$X_5$)—$R_5$—C(=$X_5$)—$X_4$—. More preferably, $X_2$ is —$CH_2CH_2$—C(=O)—NH— or —$CH_2CH_2NH$—C(=O)—$CH_2CH_2$—C(=O)—NH— and $X_3$ is a direct bond, —C(=O)—NH—, —NH—C(=O)—, —NH—C(=O)—$CH_2$, —$NHCH_2$—C(=O)—NH— or —NH—C(=O)—$CH_2CH_2$.

Preferably, each $X_4$ is independently —O— or —$NR_4$—.
Preferably, $X_5$ is O.

In certain preferred embodiments, M is —$R_5$—$X_4$—C(=$X_5$)— or —$R_5$—$X_4$—(Y$X_5$)P(=$X_5$)—$X_4$—, with M more preferably being —$CH_2$O—C(=O) or —$CH_2$O—(HO)P(=O)—O—. In certain other preferred embodiments, M is —$R_5$—$X_4$—C(=$X_5$)— or —$R_5$—C(=$X_5$)—$X_4$—. In yet other preferred embodiments, M is —$R_5$—$X_4$—(Y$X_5$)P(=$X_5$)—$X_4$— or —$X_4$—(Y$X_5$)P(=$X_5$)—$X_4$—$R_5$—. wherein at least one of $X_4$ or $X_5$ is S.

In the above formula, Z is a hydrophilic polymer. Preferably, Z is selected from the group consisting of polyalkyleneoxides, polyvinyl alcohol, polyvinylpyrrolidones, polyacrylamides, polymethacrylamides, polyphosphazenes, poly (hydroxyalkylcarboxylic acids) and polyoxazolidines. More preferably, Z comprises a polyalkyleneoxide. Even more preferably, Z is a polyalkyleneoxide selected from the group consisting of polyethylene glycol and polypropylene glycol, with polyethylene glycol being still more preferred. In certain other preferred embodiments, Z is a hydrophilic polymer other than polyalkylene-oxides, including polyethylene glycol and polypropylene glycol. The molecular weight of Z may vary, depending, for example, on the particular end-use of the compounds. Preferably, Z is a polymer having a molecular weight which ranges from about 100 to about 10,000, and all combinations and subcombinations of ranges therein. More preferably, Z is a polymer having a molecular weight of from about 1,000 to about 5,000. Also preferred are polymers which exhibit polydispersities ranging from greater than about 1 to about 3, and all combinations and subcombinations of ranges therein. More preferably, Z is a polymer having a polydispersity of from greater than about 1 to about 2, with polydispersities of from greater than about 1 to about 1.5 being even more preferred, and polydispersities of from greater than about 1 to about 1.2 being still more preferred.

In the above formula, Q is a targeting ligand or a precursor thereto. In embodiments where Q is a targeting ligand, Q is preferably selected from the group consisting of proteins, peptides, saccharides, steroids, steroid analogs, and genetic material. In these latter embodiments, Q is preferably selected from the group consisting of proteins, peptides and saccharides.

In the above formula, each $R_1$ is independently alkyl which ranges from 1 to about 50 carbons, and all combinations and subcombinations of ranges therein, or alkenyl of from about 2 to about 50 carbons, and all combinations and subcombinations of ranges therein. Preferably, each $R_1$ is independently alkyl of greater than 1 to about 40 carbons. More preferably, each $R_1$ is independently alkyl of about 5 to about 30 carbons. Even more preferably, each $R_1$ is independently alkyl of about 10 to about 20 carbons, with alkyl of about 15 carbons being still more preferred. In certain preferred embodiments, $R_1$ is a shorter chain alkyl of from 1 to about 20 carbons. In certain other preferred embodiments, $R_1$ is a longer chain alkyl of from about 20 to about 50 carbons, or about 30 to about 50 carbons. In other preferred embodiments, the alkyl group in $R_1$ may be substituted with one or more fluorine atoms, and may be perfluorinated.

In the above formula, each $R_2$ is independently alkylene which ranges from 1 to about 30 carbons, and all combinations and subcombinations of ranges therein. Preferably, each $R_2$ is independently alkylene of 1 to about 20 carbons. More preferably, each $R_2$ is independently alkylene of 1 to about 10 carbons. Even more preferably, each $R_2$ is independently alkylene of 1 to about 5 carbons, with methylene being especially preferred. In other preferred embodiments, the alkylene group in $R_2$ may be substituted with one or more fluorine atoms, and may be perfluorinated.

In the above formula, each of $R_3$ and $R_4$ is independently hydrogen or alkyl which ranges from 1 to about 10 carbons, and all combinations and subcombinations of ranges therein. Preferably, each of $R_3$ and $R_4$ is hydrogen or alkyl of 1 to about 5 carbons. More preferably, each of $R_3$ and $R_4$ is hydrogen.

In the above formula, each $R_5$ is independently a direct bond or alkylene which ranges from 1 to about 30 carbons, and all combinations and subcombinations of ranges therein. Preferably, each $R_5$ is independently a direct bond or alkylene of 1 to about 20 carbons. More preferably, each $R_5$ is independently a direct bond or alkylene of 1 to about 10 carbons. Even more preferably, each $R_5$ is independently a direct bond or alkylene of 1 to about 5 carbons. Still more preferably, each $R_5$ is a direct bond or —$(CH_2)_x$—, where x is 1 or 2.

The compositions of the present invention may be stored in an aqueous medium and used as preformed compositions prior to use. They may also be lyophilized with conventional techniques and cryopreserving agents. The compositions can then be rehydrated or reconstituted prior to administration to a patient. Cryopreserving agents prevent the compositions from being damaged from ice crystal intercalation during the sublimation of water. Agents suitable for cryoprotection include carbohydrates such as saccharides, such as sucrose, sugar alcohols such as mannitol and sorbitol, surface active agents such as polyoxyalkylene sorbitan fatty acid esters (such as the class of compounds referred to as TWEEN®, including TWEEN® 20, TWEEN® 40 and TWEEN® 80, commercially available from ICI Americans, Inc., Wilmington, Del.) and glycerol and dimethylsulfoxide.

A wide variety of methods are available for the preparation of the stabilizing materials and compositions, including vesicles. Included among these methods are, for example, shaking, drying, gas-installation, spray drying, and the like. Suitable methods for preparing vesicle compositions are described, for example, in U.S. Pat. No. 5,469,854, the disclosure of which is hereby incorporated herein by reference in its entirety. The compositions are preferably prepared from lipids which remain in the gel state.

Micelles may be prepared using any of a variety of conventional micellar preparatory methods which will be apparent to one skilled in the art. These methods typically involve suspension of the stabilizing material, such as a lipid compound, in an organic solvent, evaporation of the solvent, resuspension in an aqueous medium, sonication and centrifugation. The foregoing methods, as well as others, are described, for example, in Canfield et al, *Methods in Enzymology*, 189:418–422 (1990); El-Gorab et al, *Biochem. Biophys. Acta*, 306:58–66 (1973); *Colloidal Surfactant*, Shinoda, K., Nakagana, Tamamushi and Isejura, Academic Press, NY (1963) (especially "The Formation of Micelles", Shinoda, Chapter 1, pp. 1–88); *Catalysis in Micellar and Macromolecular Systems*, Fendler and Fendler, Academic Press, NY (1975). The disclosures of each of the foregoing publications are hereby incorporated herein by reference in their entirety.

In liposomes, the lipid compound(s) may be in the form of a monolayer, bilayer, or multi-layer (i.e., multilamellar) and the monolayer or bilayer lipids may be used to form one or more monolayers or bilayers. In the case of more than one monolayer or bilayer, the monolayers or bilayers are generally concentric. Thus, lipids may be used to form unilamellar compositions or liposomes (comprised of one monolayer or bilayer), oligolamellar compositions or liposomes (comprised of two or three monolayers or bilayers) or multilamellar compositions or liposomes (comprised of more than three monolayers or bilayers).

Additionally, the compositions may be prepared using any one of a variety of conventional liposomal preparatory techniques which will be apparent to one skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the compositions in various fashions. See, e.g., Madden et al., *Chemistry and Physics of Lipids*, 53:37–46 (1990), the disclosure of which is hereby incorporated herein by reference in its entirety. Suitable freeze-thaw techniques are described, for example, in International Application Serial No. PCT/US89/05040, filed Nov. 8, 1989, the disclosure of which is hereby incorporated herein by reference in its entirety. Methods. which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug™ (Crescent Dental, Lyons, Ill.), a Mixomat (Degussa AG Frankfurt, Germany), a Capmix (Espe Fabrik Pharmazeutischer Praeparate GMBH & Co., Seefeld, Oberay Germany), a Silamat Plus (Vivadent, Lechtenstein), or a Vibros (Quayle Dental, Sussex, England). Conventional microemulsification equipment, such as a Microfluidizer™ (Microfluidics, Woburn, Mass.) may also be used.

Spray drying may be employed to prepare gas filled vesicles. Utilizing this procedure, the stabilizing materials, such as lipids, may be pre-mixed in an aqueous environment and then spray dried to produce gas and/or gaseous precursor filled vesicles. The vesicles may be stored under a headspace of a desired gas.

Many liposomal preparatory techniques which may be adapted for use in the preparation of vesicle compositions are discussed, for example, in U.S. Pat. Nos. 4,728,578, 4,728,575, 4,737,323, 4,533,254, 4,162,282, 4,310,505, and 4,921,706; U.K. Patent Application GB 2193095A; International Application Serial Nos. PCT/US85/01161 and PCT/US89/05040; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, Investigative Radiology, 22:47–55 (1987); and *Liposome Technology*, Gregoriadis, G., ed., Vol. I, pp. 29–31, 51–67 and 79–108 (CRC Press Inc., Boca Raton, Fla. 1984), the disclosures of each of which are hereby incorporated by reference herein in their entirety.

In connection with stabilizing materials, and especially compositions in the form of vesicles, it may be advantageous to prepare the compositions at a temperature below the gel to liquid crystalline phase transition temperature of the lipids. This phase transition temperature is the temperature at which a lipid bilayer will convert from a gel state to a liquid crystalline state. See, for example, Chapman et al., *J. Biol. Chem.*, 249:2512–2521 (1974), the disclosure of which is hereby incorporated by reference herein in its entirety. Generally, vesicles that are prepared from lipids that possess higher gel state to liquid crystalline state phase transition temperatures tend to have enhanced impermeability at any given temperature. See Derek Marsh, *CRC Handbook. of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be apparent to one skilled in the art and are described, for example, by Gregoriadis, ed., *Liposome Technology*, Vol. I, 1–18 (CRC Press, 1984).

Compositions comprising a gas can be prepared by agitating an aqueous solution containing, if desired, a stabilizing material, in the presence of a gas. The term "agitating" means any shaking motion of an aqueous solution such that gas is introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay Germany) being preferred. It has been found that certain modes of shaking or vortexing can be used to make vesicles within a preferred size range. Shaking is preferred, preferably with the Espe Capmix mechanical shaker. With this method, it a reciprocating motion is preferably utilized to generate the lipid compositions, particularly vesicles. The reciprocating motion is preferably in the form of an arc. The rate of reciprocation, as well as the arc thereof, is particularly important in connection with the formation of vesicles. Preferably, the number of reciprocations or full cycle oscillations is from about 1000 to about 20,000 per minute, more preferably from about 2500 to about 8000 per minute, even more preferably from about 3300 to about 5000 per minute. The number of oscillations can be dependent upon the mass of the contents being agitated. Generally, a larger mass requires fewer oscillations. The action of gas emitted under high velocity or pressure is another means for producing shaking.

It will be understood that with a larger volume of aqueous solution, the total amount of force will be correspondingly increased. Vigorous shaking is defined as at least about 60 shaking motions per minute. Preferably, vortexing occurs at about 60 to about 300 revolutions per minute, more preferably at about 300 to about 1800 revolutions per minute.

In addition to the simple shaking methods described above, more elaborate methods can be employed, including, for example, liquid crystalline shaking gas instillation processes and vacuum drying gas instillation processes, such as those described in U.S. Pat. Nos. 5,469,854, 5,580,575, 5,585,112, and 5,542,935, and U.S. application Ser. No. 08/307,305, filed Sep. 16, 1994, the disclosures of which are incorporated herein by reference in their entirety. Emulsion processes may be employed in the preparation of the compositions of the present invention. Such emulsification processes are described, for example, in Quay, U.S. Pat. Nos. 5,558,094, 5,558,853, 5,558,854, and 5,573,751, the disclosures of which are hereby incorporated herein by reference in their entirety.

Although any number of techniques can be used, the compositions of the present invention are preferably prepared using a shaking technique. Preferably, the shaking technique involves agitation with a mechanical shaking apparatus, such as an Espe Capmix (Seefeld, Oberay Germany), using, for example, the techniques described in U.S. application Ser. No. 160,232, filed Nov. 30, 1993, the disclosure of which is hereby incorporated herein by reference in its entirety. In addition, after extrusion and sterilization procedures, which are discussed in detail below, agitation or shaking may provide compositions which contain substantially no or minimal residual anhydrous lipid phase in the remainder of the solution. (Bangham, et al, *J. Mol. Biol.*, 13:238–252 (1965).) Other preparatory techniques include those described in Unger, U.S. Pat. No. 5,205,290, the disclosure of which is hereby incorporated herein by reference in its entirety.

Foams can also be produced by shaking gas filled vesicles, wherein the foam appears on the top of the aqueous solution, and is coupled with a decrease in the volume of the aqueous solution upon the formation of foam. Preferably, the final volume of the foam is at least about two times the initial volume of the aqueous stabilizing material solution; more preferably, about three times the initial volume of the aqueous solution; even more preferably, about four times the initial volume of the aqueous solution; and most preferably, all of the aqueous stabilizing material solution is converted to foam.

The required duration of shaking time may be determined by detection of the formation of foam. For example, 10 ml of lipid solution in a 50 ml centrifuge tube may be vortexed for about 15–20 minutes or until the viscosity of the gas filled liposomes becomes sufficiently thick so that it no longer clings to the side walls as it is swirled. At this time, the foam may cause the solution containing the gas filled liposomes to raise to a level of 30 to 35 ml.

The concentration of lipid required to form a preferred foam level will vary depending upon the type of lipid used, and may be readily determined by one skilled in the art, in view of the present disclosure. For example, the concentration of 1,2-dipalmitoyl-phosphatidylcholine (DPPC) used to form gas filled liposomes according to the methods of the present invention is about 20 mg/ml to about 30 mg/ml saline solution. The concentration of distearoylphosphatidylcholine (DSPC) used is about 5 mg/ml to about 10 mg/ml saline solution. Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

Microemulsification is a common method of preparing an emulsion of a foam precursor. Temperature increases and/or lowered pressures will cause foaming as gas bubbles form in the liquid. The foam may be stabilized, for example, by surfactants, fluorosurfactants, detergents or polymers.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared by the methods described herein can range in size from less than about 1 $\mu$m to greater than about 100 $\mu$m. After extrusion and sterilization procedures, which are discussed herein, agitation or shaking provides vesicle compositions which provide substantially no or minimal residual anhydrous lipid phase in the remainder of the solution. (Bangham et al, *J. Mol. Biol.*, 13:238–252 (1965)). If desired, the compositions of the present invention may be used as they are formed, without any attempt at further modification of the size thereof For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 $\mu$m to about 100 $\mu$m.

The gas filled vesicles may be sized by a simple process of extrusion through filters wherein the filter pore sizes control the size distribution of the resulting gas filled vesicles. By using two or more cascaded or stacked sets of filters, for example, a, 10 $\mu$m filter followed by an 8 $\mu$m filter, the gas filled vesicles can be selected to have a very narrow size distribution of about 7 to about 9 $\mu$m. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by an extraction step which comprises extruding the vesicles from the barrel through the filter fitted to the syringe between the barrel and the needle, thereby sizing the vesicles before they are administered to a patient. The extraction step may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

In certain preferred embodiments, the vesicle compositions may be heat sterilized or filter sterilized and extruded through a filter prior to shaking. Generally, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and gaseous precursor filled vesicles provide sterile gas filled vesicles ready for administration to a patient. For example, a mixing vessel, such as a vial or syringe, may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to bout 5 $\mu$m, more preferably, about 0.1 to about 4 $\mu$m, even more preferably, about 0.1 o about 2 $\mu$m, and still more preferably, about 1 $\mu$m. Unhydrated compound, which is generally undesirable, appears as amorphous clumps of non-uniform size.

The sterilization step provides a composition that may be administered to a patient for therapeutic applications, such as drug delivery or diagnostic imaging. In preferred embodiments, sterilization may be accomplished by heat sterilization, such as autoclaving the solution at a temperature of at least about 100° C., preferably at about 100° C. to about 130° C., even more preferably about 110° C. to about 130° C., still more preferably about 120° C. to about 130°

C., and most preferably about 130° C. Heating occurs for at least about 1 minute, more preferably about 1 to about 30 minutes, even more preferably about 10 to about 20 minutes, and most preferably about 15 minutes. If desired, the extrusion and heating steps may be reversed or only one of the two steps can be used. Other modes of sterilization may be used, including, for example, exposure to gamma radiation.

In addition, gaseous precursors contained in vesicles can be formulated which, upon activation, for example, by exposure to elevated temperature, varying pH, or light, undergo a phase transition from, for example, a liquid, including a liquid entrapped in a vesicle, to a gas, expanding to create the gas filled vesicles described herein. This technique is described in U.S. application Ser. No. 08/159,687, filed Nov. 30, 1993, and U.S. Pat. No. 5,542,935, the disclosures of which are hereby incorporated herein by reference in their entirety.

The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors have boiling points in the range of about −100° C. to about 70° C. The activation temperature is particular to each gaseous precursor. An activation temperature of about 37° C., or about human body temperature, is preferred for gaseous precursors. Thus, a liquid gaseous precursor is activated to become a gas at about 37° C. or lower. The gaseous precursor may be in liquid or gaseous phase for use in the methods of the present invention.

The methods of preparing the gaseous precursor filled vesicles may be carried out below the boiling point of the gaseous precursor such that a liquid is incorporated in the composition. The methods may also be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, such that the process starts with a gaseous precursor as a liquid and ends with a gas.

The gaseous precursor may be selected to form the gas in situ in the targeted tissue or fluid, in vivo upon entering the patient or animal, prior to use, during storage, or during manufacture. The methods of producing the temperature-activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place when the temperature is allowed to exceed the boiling point of the precursor. The size of the vesicles, upon attaining the gaseous state, may be determined when the amount of liquid in a droplet of liquid gaseous precursor is known.

Alternatively, the gaseous precursors may be utilized to create stable gas filled vesicles which are pre-formed prior to use. In this embodiment, the gaseous precursor is added to a container housing a lipid composition at a temperature below the liquid-gaseous phase transition temperature of the gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the composition. For example, liquid perfluorobutane can be entrapped in the lipid vesicles and, as the temperature is raised above the boiling point of perfluorobutane (4° C.), perfluorobutane gas is entrapped in the vesicles.

Accordingly, the gaseous precursors may be selected to form gas filled vesicles in vivo or may be designed to produce the gas filled vesicles in situ, during the manufacturing process, on storage, or at some time prior to use. A water bath, sonicator or hydrodynamic activation by pulling back the plunger of a syringe against a closed stopcock may be used to activate targeted gas filled vesicles from temperature-sensitive gaseous precursors prior to IV injection.

By preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, an upper size limit of the gas filled vesicle can be predicted.

A mixture of a lipid and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is PV=nRT, where P is pressure in atmospheres (atm); V is volume in liters (L); n is moles of gas; T is temperature in degrees Kelvin (K); and R is the ideal gas constant (22.4 L-atm/K-mole). With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming instantaneous expansion into a gas filled vesicle and negligible diffusion of the gas over the time of the expansion.

For stabilization of the precursor in the liquid state in a mixture where the precursor droplet is spherical, the volume of the precursor droplet may be determined by the equation: Volume (spherical vesicle)=4/3 $\pi r^3$, where r is the radius of the sphere.

Once the volume is predicted, and knowing the density of the liquid at the desired temperature, the amount of liquid gaseous precursor in the droplet may be determined. In more descriptive terms, the following can be applied: $V_{gas}$=4/3 $\pi(r_{gas})^3$, by the ideal gas law, PV=nRT, substituting reveals, $V_{gas}$=nRT/$P_{gas}$ or, (A) n=4/3 [$\pi r_{gas}^3$] P/RT, where amount $n=4/3 \ [\pi r_{gas}^3 \ P/RT] \cdot MW_n$. Converting back to a liquid volume (B) $V_{liq}=[4/3 \ [\pi r_{gas}^3] \ P/RT \cdot MW_n/D]$, where D is the density of the precursor. Solving for the diameter of the liquid droplet, (C) diameter/2=$[3/4\pi[4/3\cdot[\pi r_{gas}^3] \ P/RT] \ MW_n/D]^{1/3}$, which reduces to Diameter=$2[[r_{gas}^3] \ P/RT \ [MW_n/D]]^{1/3}$.

As a further means of preparing compositions of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 μm diameter. In this example, the vesicle is formed in the bloodstream of a human being, thus the typical temperature would be 37° C. or 310 K. At a pressure of 1 atmosphere and using the equation in (A), $7.54 \times 10^{-17}$ moles of gaseous precursor would be required to fill the volume of a 10 μm diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor would be required for a 10 μm vesicle. Extrapolating further, and with the knowledge of the density, equation (B) further predicts that $8.47 \times 10^{-16}$ mL of liquid precursor is necessary to form a vesicle with an upper limit of 10 μm.

Finally, using equation (C), a mixture, for example, an emulsion containing droplets with a radius of 0.0272 μm or a corresponding diameter of 0.0544 μm, is formed to make a gaseous precursor filled vesicle with an upper limit of a 10 μm vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can also be used as a sterile filtration.

This embodiment for preparing gas filled vesicles may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation: $\ln x_a = \ln \ (1-x_b) = \Delta H_{fus} R 1/T_o - 1/T)$, where $x_a$ is the mole fraction of the solvent; $x_b$ is the mole fraction of the solute; $\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as $x^b = \Delta H_{fus}/R[T-T_o/T_oT] \approx \Delta H_{fus} \Delta T/RT_o^2$. This equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows: $X_b = m/[m+1000/m_a] \approx mMa/1000$, where Ma is the molecular weight of the solvent. Thus, substituting for the fraction $x_b \Delta T = [M_a RT_o^2/1000\Delta H_{fus}]m$ or $\Delta T = K_f m$, where $K_f = M_a RT_o^2/1000\Delta H_{fus}$. $K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed;

(b) microemulsification where an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool. Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, Szoka and Papahadjopoulos, *Proc. Natl. Acad. Sci.* (1978) 75, 4194–4198. In contrast, the vesicles made according to embodiments described herein are gaseous precursor filled, which imparts greater flexibility, since gaseous precursors after gas formation are more compressible and compliant than an aqueous solution.

The methods contemplated by the present invention provide for shaking an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve micro-emulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, a gas, such as air, may also be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

The gaseous precursor filled vesicles can be used in substantially the same manner as the gas filled vesicles described herein, once activated by application to the tissues of a host, where such factors as temperature or pH may be used to cause generation of the gas. It is preferred that the gaseous precursors undergo phase transitions from liquid to gaseous states at or near the normal body temperature of the host, and are thereby activated, for example, by the in vivo temperature of the host so as to undergo transition to the gaseous phase therein. Alternatively, activation prior to IV injection may be used, for example, by thermal, mechanical or optical means. This activation can occur where, for example, the host tissue is human tissue having a normal temperature of about 37° C. and the gaseous precursors undergo phase transitions from liquid to gaseous states near 37° C.

In any of the techniques described above for the preparation of lipid compositions, bioactive agents, targeting ligands and/or counter ions may be incorporated with the lipids before, during or after formation of the compositions, as would be apparent to one skilled in the art in view of the present disclosure. For example, the stabilizing materials and/or compositions may be prepared from a mixture of lipid compounds, counter ions, bioactive agents, targeting ligands, and gases and/or gaseous precursors. In this case, lipid compositions are prepared as described above in which the compositions also comprise counter ions, targeting ligands, and/or bioactive agents. Thus, for example, micelles can be prepared in the presence of a counter ion, targeting ligand, and/or bioactive agent. In connection with lipid compositions which comprise a gas, the preparation can involve, for example, bubbling a gas directly into a mixture of the lipid compounds and one or more additional materials, such as counter ions. Alternatively, the lipid compositions may be preformed from lipid compounds, counter ions, bioactive agents, targeting ligands, gases and/or gaseous precursors. In the latter case, the counter ion, targeting ligand, and/or bioactive agent is added to the lipid composition prior to use. For example, an aqueous mixture of liposomes and gas may be prepared to which the counter ion, targeting ligand, and/or bioactive agent is added and which is agitated to provide the liposome composition. The liposome composition can be readily isolated since the gas, targeting ligand, and/or bioactive agent filled liposome vesicles generally float to the top of the aqueous solution. Excess bioactive agent and/or targeting ligand can be recovered from the remaining aqueous solution.

As one skilled in the art will recognize, any of the stabilizing materials and/or compositions may be lyophilized for storage, and reconstituted or rehydrated, for example, with an aqueous medium (such as sterile water, phosphate buffered solution, or aqueous saline solution), with the aid of vigorous agitation. Lyophilized preparations generally have the advantage of greater shelf life. To prevent agglutination or fusion of the lipids as a result of lyophilization, additives which prevent such fusion or agglutination may be added. Suitable additives include, for example, sorbitol, mannitol, sodium chloride, glucose, trehalose, polyvinyl-pyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosure of which is hereby incorporated herein by reference in its entirety.

The concentration of lipid required to form a desired stabilized composition will vary depending upon the type of lipid used, and may be readily determined by routine experimentation. The amount of composition which is administered to a patient can vary. Typically, the intravenous dose may be less than about 10 ml for a 70 kg patient, with lower doses being preferred.

Another embodiment of preparing a composition comprises combining at least one lipid and a gaseous precursor; agitating until gas filled vesicles are formed; adding a bioactive agent and/or targeting ligand to the gas filled vesicles such that the bioactive agent and/or targeting ligand binds to the gas filled vesicle by a covalent bond or non-covalent bond; and agitating until a composition comprising gas filled vesicles and a bioactive agent and/or targeting ligand result. Rather than agitating until gas filled vesicles are formed before adding the bioactive agent and/or targeting ligand, the gaseous precursor may remain a gaseous precursor until the time of use. That is, the gaseous precursor is used to prepare the composition and the precursor is activated in vivo by temperature, for example.

Alternatively, a method of preparing compositions may comprise combining at least one lipid and a bioactive agent and/or targeting ligand such that the bioactive agent and/or targeting ligand binds to the lipid by a covalent bond or non-covalent bond, adding a gaseous precursor and agitating until a composition comprising gas-filled vesicles and a bioactive agent and/or targeting ligand result. In addition, the gaseous precursor may be added and remain a gaseous precursor until the time of use. That is, the gaseous precursor is used to prepare the composition having gaseous precursor filled vesicles and a bioactive agent and/or targeting ligand which result for use in vivo.

Alternatively, the gaseous precursors may be utilized to create stable gas filled vesicles with bioactive agents and/or targeting ligands which are pre-formed prior to use. In this embodiment, the gaseous precursor and bioactive agent and/or targeting ligand are added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas for example, air, or coentrap gas state gaseous precursor and ambient air. This phase transition can be used for optimal mixing and stabilization of the composition. For example, the gaseous precursor, perfluorobutane, can be entrapped in the lipid, and as the temperature is raised beyond 4° C. (boiling point of perfluorobutane), a lipid entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, stable gas filled vesicles result.

The stabilized vesicle precursors described above can be used in the same manner as the other stabilized vesicles used in the present invention, once activated by application to the tissues of a host, where such factors as temperature or pH may be used to cause generation of the gas. It is preferred that this embodiment is one wherein the gaseous precursors undergo phase transitions from liquid to gaseous states at or near the normal body temperature of the host, and are thereby activated by the temperature of the host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the compositions, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The compositions are generally stored as an aqueous suspension, but in the case of dried or lyophilized vesicles or dried or lyophilized lipid spheres, the compositions may be stored as a dried or lyophilized powder ready to be reconstituted or rehydrated prior to use.

In accordance with the present invention, there are provided methods of imaging a patient, diagnosing the presence of diseased tissue in a patient, delivering a bioactive agent (with or without a targeting ligand) to a patient and/or treating a condition in a patient. The imaging process of the present invention may be carried out by administering a composition of the invention to a patient, and then scanning the patient using, for example, ultrasound, computed tomography, and/or magnetic resonance imaging, to obtain visible images of an internal region of a patient and/or of any diseased tissue in that region. Diagnostic imaging includes promoting the rupture of compositions (such as vesicles) via the methods of the present invention. For example, ultrasound may be used to visualize the compositions and verify the location of the compositionss in certain tissue. In addition, ultrasound may be used to promote rupture of the compositionss once they reach the intended target, including tissue and/or receptor destinations, thus releasing a bioactive agent.

The compositions of the invention may be administered to the patient by a variety of different means, which will vary depending upon the intended application. As one skilled in the art would recognize, administration of the compositions of the present invention can be carried out in various fashions including, for example, topically, including ophthalmic, dermal, ocular and rectal, intrarectally, transdermally, orally, intraperitoneally, parenterally, intravenously, intralymphatically, intratumorly, intramuscularly, interstitially, intra-arterially, subcutaneously, intraocularly, intrasynovially, transepithelially, transdermally, pulmonarily via inhalation, ophthalmically, sublingually, buccally, or nasal inhalation via insufflation or nebulization.

Preferably, the compositions of the present invention are administered to a patient as an infusion. "Infusion" refers to intravascular or intra-arterial administration at a rate of, for example, less than about 1 cc/second, more preferably less than about 0.5 cc/second or less than about 30 cc/minute, even more preferably about 0.1 cc/minute to about 30 cc/minute. Varying the rate of infusion is also desirable. For example, infusion may initially be started at a rate of about 1.0 to about 4.0 cc/second, followed by a more sustained infusion rate of about 0.1 cc/second. The fast infusion rate initially achieves the optimal level of the stabilizing material and/or vesicle in the blood, while the slow infusion rate is better tolerated hemodynamically.

The compositions of the present invention are preferably highly active in low concentrations. The amount of composition of the present invention to be administered to a patient depends, for example, on whether a bioactive agent and/or targeting ligand is being used, the method in which the composition is being administered, and the age, sex, weight and physical condition of the patient. Generally, treatment is initiated with small dosages, which can then be increased by small increments, until the desired effect under the circumstances is achieved. The targeting aspects of the invention enable lower dosages of the compositions to be used for therapy, since the effective concentration of the compositions at the therapeutic site remains undiluted in the body. Additionally, one skilled in the art may rely on reference materials, such as the *Physician's Desk Reference*, published by Medical Economics Company at Montvale, N.J. 07645-1742, to determine the appropriate amount of a particular bioactive agent, and hence the corresponding composition of the invention that may be administered to a patient. In accordance with the present invention, compositions comprising a bioactive agent may be delivered (with or without a targeting ligand) to a patient (e.g., in a region of the patient) for the purposes, for example, of treating a condition (i.e., a disease state, malady, disorder, etc.) in the patient.

Ultrasound mediated targeting and drug release and activation using the compositions of the present invention is advantageous for treating a variety of different diseases and medical conditions, such as autoimmune diseases, organ transplants, arthritis, and myasthenia gravis. Following the systemic administration of the compositions to a patient, ultrasound may then be applied to the affected tissue.

Compositions formulated with penetration enhancing agents, known to one skilled in the art, may be administered transdermally in a patch or reservoir with a permeable membrane applied to the skin. The use of rupturing ultrasound may increase transdermal delivery of bioactive agents, including the compositions of the present invention. Further, a mechanism may be used to monitor and modulate delivery of the compositions. For example, diagnostic ultrasound may be used to visually monitor the bursting of the gas filled vesicles and modulate drug delivery and/or a hydrophone may be used to detect the sound of the bursting of the gas filled vesicles and modulate drug delivery.

The delivery of bioactive agents from the compositions of the present invention using ultrasound is best accomplished for tissues which have a good acoustic window for the transmission of ultrasonic energy. This is the case for most tissues in the body such as muscle, the heart, the lungs, the liver and most other vital structures. In the brain, in order to direct the ultrasonic energy past the skull, a surgical window may be necessary.

Further, the compositions of the present invention are especially useful for bioactive agents that may be degraded in aqueous media or upon exposure to oxygen and/or atmospheric air. For example, the vesicles may be filled with an inert gas such as nitrogen or argon, for use with labile bioactive agents. Additionally, the gas filled vesicles may be filled with an inert gas and used to encapsulate a labile bioactive agent for use in a region of a patient that would normally cause the bioactive agent to be exposed to atmospheric air, such as cutaneous and ophthalmic applications.

The invention is useful in delivering bioactive agents to a patient's lungs. For pulmonary applications, dried or lyophilized powdered compositions may be administered via an inhaler. Aqueous suspensions of liposomes or micelles, preferably gas/gaseous precursor filled, may be administered via nebulization. Gas filled liposomes of the present invention are lighter than, for example, conventional liquid filled liposomes which generally deposit in the central proximal airway rather than reaching the periphery of the lungs. It is therefore believed that the gas filled liposomes of the present invention may improve delivery of a bioactive agent to the periphery of the lungs, including the terminal airways and the alveoli. For application to the lungs, the gas filled liposomes may be applied through nebulization or insufflation.

In applications such as the targeting of the lungs, which are lined with lipids, the bioactive agent may be released upon aggregation of the gas filled liposomes with the lipids lining the targeted tissue. Additionally, the gas filled liposomes may burst after administration without the use of ultrasound. Thus, ultrasound need not be applied to release the drug in the above type of administration.

For vascular administration, the compositions are generally injected into the venous system as, for example, a gas and/or gaseous precursor containing liposome.

It is a further embodiment of this invention in which ultrasound activation affords site specific delivery of the compositions. Generally, the gas and/or gaseous precursor containing vesicles are echogenic and visible on ultrasound. Ultrasound can be used to image the target tissue and to monitor the drug carrying vesicles as they pass through the treatment region. As increasing levels of ultrasound are applied to the treatment region, this breaks apart the vesicles and/or releases the drug within the treatment region.

Drug release and/or vesicle rupture can be monitored ultrasonically by several different mechanisms. As bubbles are destroyed this results in eventual dissolution of the ultrasound signal. Prior to signal dissolution, however, the vehicles provide an initial burst of signal. In other words as increasing levels of ultrasound energy are applied to the treatment zone containing the vehicles, there is a transient increase in signal. This transient increase in signal may be recorded at the fundamental frequency, the harmonic, odd harmonic or ultraharmonic frequency.

Generally, the delivery systems of the present invention are administered in the form of an aqueous suspension such as in water or a saline solution (e.g., phosphate buffered saline). Preferably, the water is sterile. Also, preferably the saline solution is an isotonic saline solution, although the saline solution may be hypotonic (e.g., about 0.3 to about 0.5% NaCl). The solution may also be buffered to provide a pH range of about pH 5 to about pH 7.4. In addition, sugars, such as dextrose, and/or salts may be included in the media. Other solutions that may be used to administer gas filled liposomes include oils, such as, for example, almond oil, corn oil, cottonseed oil, ethyl oleate, isopropyl myristate, isopropyl palmitate, mineral oil, myristyl alcohol, octyldodecanol, olive oil, peanut oil, persic oil, sesame oil, soybean oil, squalene and fluorinated oils.

The size of the stabilizing materials and/or vesicles of the present invention will depend upon the intended use. With smaller liposomes, resonant frequency ultrasound will generally be higher than for the larger liposomes. Sizing also serves to modulate resultant liposomal biodistribution and clearance. In addition to filtration, the size of the liposomes can be adjusted, if desired, by procedures known to one skilled in the art, such as shaking, microemulsification, vortexing, filtration, repeated freezing and thawing cycles, extrusion, extrusion under pressure through pores of a defined size, sonication, homogenization, the use of a laminar stream of a core of liquid introduced into an immiscible sheath of liquid. Extrusion under pressure through pores of defined size is a preferred method of adjusting the size of the liposomes. See, U.S. Pat. Nos. 4,728,578, 4,728,575, 4,737,323, 4,533,254, 4,162,282, 4,310,505 and 4,921,706; U.K. Patent Application GB 2193095 A; International Applications PCT/US85/01161 and PCT/US89/05040; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); *Liposomes Technology*, Gregoriadis, ed., Vol. I, pp. 29–108 (CRC Press Inc, Boca Raton, Fla., 1984). The disclosures of each of the foregoing patents, publications and patent applications are hereby incorporated by reference herein in their entirety.

Since vesicle size influences biodistribution, different size vesicles may be selected for various purposes. For intravascular applications, the size range is a mean outside diameter between about 30 nm and about 10 $\mu$m, preferably about 5 $\mu$m. More specifically, for intravascular applications the size of the vesicles is about 10 $\mu$m or less in mean outside diameter, and preferably less than about 7 $\mu$m, and more preferably less than about 5 $\mu$m in mean outside diameter. Preferably, the vesicles are no smaller than about 30 nm in mean outside diameter. To provide therapeutic delivery to organs such as the liver and to allow differentiation of tumor from normal tissue, smaller vesicles, between about 30 nm and about 100 nm in mean outside diameter, are preferred. For embolization of a tissue such as the kidney or the lung, the vesicles are preferably less than about 200 $\mu$m in mean outside diameter. For intranasal, intrarectal or topical administration, the vesicles are preferably less than about 100 $\mu$m in mean outside diameter. Large vesicles, e.g., between 1 and 10 $\mu$m in size, will generally be confined to the intravascular space until they are cleared by phagocytic elements lining the vessels, such as the macrophages and Kupffer cells lining capillary sinusoids. For passage to the cells beyond the sinusoids, smaller vesicles, for example, less than about 1 $\mu$m in mean outside diameter, e.g., less than about 300 nm in size, may be utilized. In preferred embodiments, the vesicles are administered individually, rather than embedded in a matrix, for example.

For intravenous injection, the size of the particle should be under 7 $\mu$m. For drug delivery to selective sites in vivo, smaller sizes under 2 $\mu$m, more preferably under 0.5 $\mu$m, and even more preferably under 200 nm, is desired. Most preferably the compositions are under 200 nm in size and can be as small as about 5 nm to about 10 nm in size. In the compositions, the lipids covalently bonded to polymers stabilize the lipid compositions into these small structures usable for in vivo applications.

For in vitro use, such as cell culture applications, the gas and/or gaseous precursor filled vesicles may be added to the cells in cultures and then incubated. Subsequently sonic energy can be applied to the culture media containing the cells and liposomes.

In carrying out the imaging methods of the present invention, the stabilizing materials and vesicle compositions can be used alone, or in combination with targeting ligands, diagnostic agents, therapeutic agents or other agents, including excipients such as flavoring or coloring materials, which are well-known to one skilled in the art.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained. With respect to ultrasound, ultrasonic imaging techniques, including second harmonic imaging, and gated imaging, are known in the art, and are described, for example, in Uhlendorf, *IEEE Transactions on Ultrasonics, Ferroelectrics, and Frequency Control*, 14(1):70–79 (1994) and Sutherland et al, *Journal of the American Society of Echocardiography*, 7(5):441–458 (1994), the disclosures of each of which are hereby incorporated herein by reference in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the targeted contrast media of the present invention which may be targeted to the desired site, for example, blood clots. Other harmonic signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. There will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle composition. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may also be pulsed. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition, energy levels may vary from about 0.5 Watt (W) per square centimeter ($cm^2$) to about 5.0 $W/cm^2$, with energy levels of from about 0.5 to about 2.5 $W/cm^2$ being preferred. Energy levels for therapeutic ultrasound involving hyperthermia are generally from about 5 $W/cm^2$ to about 50 $W/cm^2$. For very small vesicles, for example, vesicles having a diameter of less than about 0.5 $\mu$m, higher frequencies of sound are generally preferred because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosure of which is hereby incorporated by reference herein in its entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. In the case of ultrasound involving vesicles, this second harmonic therapy may provide improved rupturing of vesicles as compared to ultrasound energy involving a single frequency. Also, the preferred frequency range may reside within the fundamental harmonic frequencies of the vesicles. Lower energy may also be used with this device. An ultrasound device which may be employed in connection with the aforementioned second harmonic therapy is described, for example, by Kawabata, et al., *Ultrasonics Sonochemistry*, 3:1–5 (1996), the disclosure of which is hereby incorporated by reference herein in its entirety.

For use in ultrasonic imaging, preferably, the vesicles of the invention possess a reflectivity of greater than 2 dB, more preferably between about 4 dB and about 20 dB. Within these ranges, the highest reflectivity for the vesicles of the invention is exhibited by the larger vesicles, by higher concentrations of vesicles, and/or when higher ultrasound frequencies are employed.

For therapeutic drug delivery, the rupturing of the compositions and/or liposomes of the invention is easily carried out by applying ultrasound of a certain frequency to the region of the patient where therapy is desired, after the liposomes have been administered to or have otherwise reached that region, e.g., via delivery with targeting ligands. It has been found that when ultrasound is applied at a frequency corresponding to the peak resonant frequency of the gas filled vesicles, the vesicles will rupture and release their contents. The peak resonant frequency can be determined either in vivo or in vitro, but preferably in vivo, by exposing the stabilizing materials or vesicles to ultrasound, receiving the reflected resonant frequency signals and analyzing the spectrum of signals received to determine the peak, using conventional means. The peak, as so determined, corresponds to the peak resonant frequency or second harmonic.

Preferably, the stabilizing materials and/or vesicle compositions of the invention have a peak resonant frequency of between about 0.5 MHz and about 10 MHz. The peak resonant frequency of the gas filled vesicles will vary depending on the outside diameter and, to some extent, the elasticity or flexibility of the liposomes, with the larger and more elastic or flexible liposomes having a lower resonant frequency than the smaller and less elastic or flexible vesicles.

The gas filled vesicles will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and bioactive agent release is improved, appreciable tissue heating does not generally occur (frequently no increase in temperature above about 2° C.), and less overall energy is required. Thus, application of ultrasound at the peak resonant frequency, while not required, is most preferred.

For diagnostic or therapeutic ultrasound, any of the various types of diagnostic ultrasound imaging devices may be employed in the practice of the invention, the particular type or model of the device not being critical to the method of the invention Also suitable are devices designed for administering ultrasonic hyperthermia, as described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the vesicle is visualized on ultrasound (for diagnostic ultrasound applications) or ruptures (for therapeutic ultrasound applications).

Although application of the various principles will be apparent to one skilled in the art in view of the present disclosure, by way of general guidance, for gas filled vesicles of about 1.5 to about 10 μm in mean outside diameter, the resonant frequency will generally be in the range of about 1 to about 10 MHz. By adjusting the focal zone to the center of the target tissue (e.g., the tumor) the gas filled vesicles can be visualized under real time ultrasound as they accumulate within the target tissue. Using the 7.5 MHz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of the bioactive agent from the gas filled vesicles, but much greater release can be accomplished by using higher power.

By switching the transducer to the doppler mode, higher power outputs are available, up to 2.5 $W/cm^2$ from the same transducer. With the machine operating in doppler mode, the power can be delivered to a selected focal zone within the target tissue and the gas filled vesicles can be made to release the bioactive agent. Selecting the transducer to match the resonant frequency of the gas filled vesicles will make the release of the bioactive agent even more efficient.

For larger diameter gas filled vesicles, e.g., greater than 3 μm in mean outside diameter, a lower frequency transducer may be more effective in accomplishing therapeutic release. For example, a lower frequency transducer of 3.5 MHz (20 mm curved array model) may be selected to correspond to the resonant frequency of the gas filled vesicles. Using this transducer, 101.6 $mW/cm^2$ may be delivered to the focal spot, and switching to doppler mode will increase the power output (SPTA) to 1.02 $Wcm^2$.

To use the phenomenon of cavitation to release and/or activate the gas filled stabilizing materials and/or vesicles, lower frequency energies may be used, as cavitation occurs more effectively at lower frequencies. Using a 0.757 MHz transducer driven with higher voltages (as high as 300 volts) cavitation of solutions of gas-filled liposomes will occur at thresholds of about 5.2 atmospheres.

The ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Cleveland, Ohio.) Echoview 8L Scanner including 80C System or the Medisonics (Mountain View, Calif.) Model D-9 Versatone Bidirectional Doppler, is known in the art and described, for example, by Carson et al., *Ultrasound in Med. & Biol*., 3:341–350 (1978), the disclosure of which is hereby incorporated herein by reference in its entirety In general, these ranges of energies employed in pulse repetition are useful for diagnosis and monitoring gas-filled liposomes but are insufficient to rupture the gas-filled liposomes of the present invention.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the liposomes and rupturing to provide local delivery of bioactive agents.

The frequency of the sound used may vary from about 0.025 to about 100 MHz. Frequency ranges between about 0.75 and about 3 MHz are preferred and frequencies between about 1 and about 2 MHz are most preferred. Commonly used therapeutic frequencies of about 0.75 to about 1.5 MHz may be used. Commonly used diagnostic frequencies of about 3 to about 7.5 MHz may also be used. For very small vesicles, e.g., below 0.5 μm in mean outside diameter, higher frequencies of sound may be preferred as these smaller vesicles will absorb sonic energy more effectively at higher frequencies of sound. When very high frequencies are used, e.g., over 10 MHz, the sonic energy will generally have limited depth penetration into fluids and tissues. External application may be preferred for the skin and other superficial tissues, but for deep structures, the application of sonic energy via interstitial probes or intravascular ultrasound catheters may be preferred.

Where the gas filled stabilizing materials and/or vesicles are used for drug delivery, the bioactive agent to be delivered may be embedded within the wall(s) of the vesicle, encapsulated in the vesicle, attached to the surface of the vesicle and/or any combination thereof. The phrase "attached to" or variations thereof means that the bioactive agent is linked in some manner to the inside and/or the outside wall of the vesicle, such as through a covalent or ionic bond or other means of chemical or electrochemical linkage or interaction. The phrase "encapsulated in" or variations thereof as used in connection with the location of the bioactive agent denotes that the bioactive agent is located in the internal vesicle void. The phrase "embedded within" or variations thereof signifies the positioning of the bioactive agent within the vesicle wall(s) or layer(s). The phrase "comprising a bioactive agent" denotes all of the varying types of therapeutic positioning in connection with the vesicle. Thus, the bioactive agent can be positioned variably, such as, for example, entrapped within the internal void of the gas filled vesicle, situated between the gas and the internal wall of the gas filled vesicle, incorporated onto the external surface of the gas filled vesicle, enmeshed within the vesicle structure itself and/or any combination thereof. The compositionss may also be designed so that there is a symmetric or an asymmetric distribution of the drug both inside and outside of the stabilizing material and/or vesicle.

More than one bioactive agent may be administered to a patient using the vesicles. For example, a single vesicle may contain more than one bioactive agent or vesicles containing different bioactive agents may be co-administered. Preferably, a targeting ligand is used in conjunction with a bioactive agent. For example, a monoclonal antibody capable of binding to melanoma antigen and an oligonucleotide encoding at least a portion of IL-2 may be administered at the same time. The phrase "at least a portion of" means that the entire gene need not be represented by the oligonucleotide, so long as the portion of the gene represented provides an effective block to gene expression.

Genetic materials and bioactive agents may be incorporated into the internal gas filled space of these vesicles during the gas installation process or into or onto the vesicle membranes of the compositions. Genetic materials and bioactive agents with a high octanol/water partition coefficient may be incorporated directly into the layer or wall surrounding the gas but incorporation onto the surface of the gas filled vesicles is more preferred. To accomplish this, groups capable of binding genetic materials or bioactive agents are generally incorporated into the stabilizing material layers which will then bind these materials. In the case of genetic materials (DNA, RNA, both single stranded and double stranded and anti-sense and sense oligonucleotides) this is readily accomplished through the use of the compositions of the present invention.

Preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphoro-thioate and phosphorodithioate oligodeoxynucleotides. Further, the genetic material may be combined, for example, with proteins or other polymers. Genetic materials that may be applied using the compositions of the present invention include, for example, DNA encoding at least a portion of an HLA gene, DNA encoding at least a portion of dystrophin, DNA encoding at least a portion of CFTR, DNA encoding at least a portion of IL-2, DNA encoding at least a portion of TNF, an antisense oligonucleotide capable of binding DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat *Hemophilia B*. See, for example, *Science*, 258, 744–746.

A gas filled vesicle filled with oxygen gas should create extensive free radicals with cavitation. Also, metal ions from the transition series, especially manganese, iron and copper can increase the rate of formation of reactive oxygen intermediates from oxygen. By encapsulating metal ions within the vesicles, the formation of free radicals in vivo can be increased. These metal ions may be incorporated into the liposomes as free salts, as complexes, e.g., with EDTA, DTPA DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gas filled vesicles to create free radicals on thermal stimulation.

As discussed above, the compositions and stabilizing materials of the present invention may be used in connection with diagnostic imaging, therapeutic imaging and drug delivery, including, for example, ultrasound (US), magnetic resonance imaging (MRI), nuclear magnetic resonance (NMR), computed tomography (CT), electron spin resonance (ESR), nuclear medical imaging, optical imaging, elastography, radiofrequency (RF) and microwave laser. The compositions and stabilizing materials of the present invention may be used in combination with various contrast agents, including conventional contrast agents, which may serve to increase their effectiveness as contrast agents for diagnostic and therapeutic imaging.

Examples of suitable contrast agents for use with MRI in combination with the present stabilizing materials include, for example, stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). More preferably, the elements may be Gd(III), Mn(II), Cu(II), Fe(II), Fe(III), Eu(III) and Dy(III), most preferably Mn(II) and Gd(III). The foregoing elements may be in the form of a salt, including inorganic salts, such as a manganese salt, for example, manganese chloride, manganese carbonate, manganese acetate, and organic salts, such as manganese gluconate and manganese hydroxyl- apatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylenediaminetetraacetic acid (EDTA), 1,4,7,10-tetraazacyclododecane-N,N',N',N'''-tetraacetic acid (DOTA), 1,4,7,10-tetraaza-cyclododecane-N,N',N'''-triacetic acid (DOTA), 3,6,9-triaza-12-oxa-3,6,9-tricarboxy-methylene-10-carboxy-13-phenyltridecanoic acid (B-19036), hydroxybenzylethylene-diamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)ethylenediamine-N,N'-diacetate (EDTA-DDP); N,N'-bis-(carboxyoctadecylamidomethyl-N-2,3-dihydroxy-propyl)ethylenediamine-N,N'-diacetate (EDTA-ODP); and N,N'-Bis(carboxylaurylamido-methyl-N-2,3-dihydroxypropyl)ethylenediamine-N,N'-diacetate (EDTA-LDP); including those described in U.S. Pat. No. 5,312,617, the disclosure of which is hereby incorporated. herein by reference in its entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred. Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, more preferably Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular theory of operation, it is contemplated that since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

Exemplary superparamagnetic contrast agents suitable for use with MRI in the compositions of the present invention include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. Paramagnetic gases can also be employed in the present compositions, such as oxygen 17 gas ($^{17}O_2$). In addition, hyperpolarized xenon, neon, or helium gas may also be employed. Magnetic resonance (MR) whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the compositionss and/or stabilizing materials. With respect to vesicles, the contrast agents may be entrapped within the internal void thereof, administered as a solution with the vesicles;, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

The stabilizing materials and/or vesicles of the present invention, and especially the vesicles, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, for example, particles having diameters of about 100 nm, have much higher R2 relaxivities as compared to R1 relaxivities. The smaller particles, for example, particles having diameters of about 10 to about 15 nm, have somewhat lower R2 relaxivities, but much more balanced R1 and R2 values. Much smaller particles, for example, monocrystalline iron oxide particles having diameters of about 3 to about 5 nm, have lower R2 relaxivities, but probably the most balanced R1 and R2 relaxation rates. Ferritin can also be formulated to encapsulate a core of very high relaxation rate superparamagnetic iron. It has been discovered that the lipid and/or vesicle compositions, especially vesicle compositions, including gas filled vesicles, can increase the efficacy and safety of these conventional iron oxide based MRI contrast agents.

The iron oxides may simply be incorporated into the stabilizing materials and/or vesicles. Preferably, in the case of vesicles formulated from lipids, the iron oxides may be incorporated into the walls of the vesicles, for example, by being adsorbed onto the surfaces of the vesicles, or entrapped within the interior of the vesicles.

Without being bound to any particular theory or theories of operation, it is believed that the vesicles of the present invention increase the efficacy of the superparamagnetic contrast agents by several mechanisms. First, it is believed that the vesicles function to increase the apparent magnetic concentration of the iron oxide particles. Also, it is believed that the vesicles increase the apparent rotational correlation time of the MRI contrast agents, including paramagnetic and superparamagnetic agents, so that relaxation rates are increased. In addition, the vesicles appear to increase the apparent magnetic domain of the contrast medium according to the manner described hereinafter.

Certain of the vesicles of the present invention, and especially vesicles formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, it should be noted that the contrast provided by these agents is dependent on particle size. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion: $1/T_1M=(2/15)\ S(S+1)\gamma^2g^2\beta^2/r^6[3\tau_c/(1+\omega_I^2\tau_c^2)+7\tau_c/(1+\omega_s^2\tau_c^2)]+(2/3)\ S(S+1)\ A^2/h^2[\tau_e/(1+\omega_s2\tau_c^2)]$ and $1/T_2M=(1/15)\ S(S+1)\ \gamma^2g^2\beta^2/r^6[4\tau_c+3\tau c/(1+\omega_I^2\tau_c^2)+13\tau_c/(1+w_s^2\tau_c^2)]+(1/3)\ S(S+1)A^2/h^2[\tau_e/(1+\omega_s2\tau_c^2)]$, where S is the electron spin quantum number; g is the electronic g factor; $\beta$ is the Bohr magneton; $\omega_I$ and $\omega_s$ (657 $w_I$) is the Larmor angular precession frequencies for the nuclear spins and electron spins; r is the ion-nucleus distance; A is the hyperfine coupling constant; $\tau_c$ and $\tau_e$ are the correlation times for the dipolar and scalar interactions, respectively; and h is Planck's constant.

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, it is believed that the total size of the particle is not as important as the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence for a paramagnetic dipole-dipole interaction. Interpreted literally, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. It has not been possible to achieve this heretofore and it is believed that the benefits have been unrecognized heretofore also. By coating the inner or outer surfaces of the vesicles with the contrast agents, even though the individual contrast agents, for example, iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible vesicles described above, it may be desirable, in certain circumstances, to formulate vesicles from substantially impermeable polymeric materials including, for example, polymethyl methacrylate. This would generally result in the formation of vesicles which may be substantially impermeable and relatively inelastic and brittle. In embodiments involving diagnostic imaging, for example, ultrasound, contrast media which comprise such brittle vesicles would generally not provide the desirable reflectivity that the flexible vesicles may provide. However, by increasing the power output on ultrasound, the brittle microspheres can be made to rupture, thereby causing acoustic emissions which can be detected by an ultrasound transducer.

Nuclear Medicine Imaging (NMI) may also be used in connection with the diagnostic and therapeutic method aspects of the present invention. For example, NMI may be used to detect radioactive gases, such as $Xe^{133}$, which may be incorporated in the present compositions in addition to, or instead of, the gases discussed above. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as technetium$^{99m}$ or indium$^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

For optical imaging, optically active gases, such as argon or neon, may be incorporated in the present compositions. In addition, optically active materials, for example, fluorescent materials, including porphyrin derivatives, may also be used. Elastography is an imaging technique which generally employs much lower frequency sound, for example, about 60 kHz, as compared to ultrasound which can involve frequencies of over 1 MHz. In elastography, the sound energy is generally applied to the tissue and the elasticity of the tissue may then be determined. In connection with preferred embodiments of the invention, which involve highly elastic vesicles, the deposition of such vesicles onto, for example, a clot, increases the local elasticity of the tissue and/or the space surrounding the clot. This increased elasticity may then be detected with elastography. If desired, elastography can be used in conjunction with other imaging techniques, such as MRI and ultrasound.

EXAMPLES

The invention is further demonstrated in the following examples. Examples 1–12 and 15 are actual examples, and Examples 13, 14 and 16–18 are prophetic examples. The examples are for purposes of illustration only and are not intended to limit the scope of the present invention.

As shown in Examples 1–5, the amount of lipid covalently bonded to the polymer can be used to influence the size distribution of the lipid compositions. The size of the resulting compositions depends upon the contents including the presence of exogenous $Ca^{2+}$. Graphical representations of the sizing data is shown in FIG. 2–4.

Example 1

Compositions containing varying amounts of dimyristoyl were prepared. Dry lipids were weighed out and hydrated in $dH_2O$ by heating and stirring in the mole percentage ratio of from 65 mole % to 75 mole % dimyristoylphosphatidylcholine (DMPC); from 15 mole % to 25 mole % dimyristoylphosphatidic acid (DMPA); and from 0 to 20 mole % dimyristoylphosphatidylethanolamine-polyethylene glycol-5,000 (DMPE-PEG5,000). A small vial was rinsed with dH2O and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered dI $H_2O$ was added by weight until the final concentration of lipid was 1 mg/ml. This mixture was heated to 45–50° C. for 1 hour and then sonicated in a Aquasonic cleaner Model 75 HT (VWR) at room temperature for 1 hour in 30 minute increments to prevent excessive heating. This treatment reduced the relative size of the lipid particles in solution. The particles were sized using a NICOMP C370 (Particle Sizing Systems, 75 Aero Camino Suite B, Santa Barbara Calif. 93117) by a modified NNLS/CONTIN algorithm resulting in a multimodal size distribution with peak intensity diameters plotted as shown in FIG. 2A. These compositions may be considered controls since no divalent cations were added either during formation or resusupension of the lipids.

Example 2

Compositions containing varying amounts of dipalmitoyl and $Ca^{2+}$ in the resuspending media were prepared. Dry lipids were weighed out and hydrated in dI $H_2O$ by heating and stirring in the mole percentage ratio of from 65 mol % to 75 mol % dipalmitoylphosphatidylcholine (DPPC); from 15 mol % to 25 mol % dipalmitoylphosphatidic acid (DPPA) and from 0 to 20 mol % dipalmitoylphosphatidylethanolamine-polyethylene glycol-5,000 (DPPE-PEG5,000). A small vial was rinsed with dI H$_2$O and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered 10 mM CaCl$_2$ was added by weight until the final concentration of lipid was 1 mg/ml. This mixture was heated to 45–50° C. for 1 hour and then sonicated in a Aquasonic cleaner Model 75 HT (VWR) at room temperature for 1 hour in 30 minute increments to prevent excessive heating. This treatment reduced the relative size of the lipid particles in solution. The particles were sized using a NICOMP C370 (Particle Sizing Systems, 75 Aero Camino Suite B, Santa Barbara Calif. 93117) by a modified NNLS/CONTIN algorithm resulting in a multimodal size distribution with peak intensity diameters as plotted in FIG. 2B.

Example 3

Compositions with DPPA ratios in excess of DPPC and no divalent cations were prepared. Dry lipids were weighed out and hydrated in dH$_2$O by heating and stirring in the mole percentage ratio of from 15 to 25 mol % DPPC; from 65 to 75 mol % DPPA; from 0 to 20 mol % DPPE-PEG5,000. A small vial was rinsed with dH$_2$O and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered dI H$_2$O was added by weight until the final concentration of lipid was 1 mg/ml. This mixture was heated to 45–50° C. for 1 hour and then sonicated in a Aquasonic cleaner Model 75 HT (VWR) at room temperature for 1 hour in 30 minute increments to prevent excessive heating. This treatment reduced the relative size of the lipid particles in solution. The particles were sized using a NICOMP C370 (Particle Sizing Systems, 75 Aero Camino Suite B, Santa Barbara Calif. 93117) by a modified NNLS/CONTIN algorithm resulting in a multimodal size distribution with peak intensity diameters as plotted in FIG. 4A.

Example 4

Compositions made with Ca$^{2+}$ present in the original mixture were prepared. The experiments in Example 3 were repeated except that 10 mM CaCl$_2$ was added to the original lipid mixtures. Sizing plots are shown in FIG. 4B.

Example 5

The experiments in Example 2 were repeated except that CaCl$_2$ was added to the original lipid suspension rather than in the resuspension. FIG. 3A shows the control size plots for the varying amounts of lipid and FIG. 3B shows the effect of the added Ca$^{2+}$.

In Examples 6–10, DNA was added to variations of the lipid mixtures described in the preceding Examples. The presence of DNA in the final precipitated lipid shows complexation. A control run without lipids showed no DNA in the final pellet. Ca$^{2+}$ was added in Examples 8 and 9.

Example 6

Dry lipids were weighed out and hydrated in dI H$_2$O by heating and stirring in the mole percentage ratio of 75 mol % DMPC to 25 mol % DMPA and then lyopholized. A small vial was rinsed with dI H$_2$0 and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered dI H$_2$O was added by weight until the final concentration of lipid was 1 mg/ml. This mixture was heated to 45–50° C. for 1 hour and then sonicated in a Aquasonic cleaner Model 75 HT (VWR) at room temperature for 1 hour in 30 minute increments to prevent excessive heating.

200 μg of pCAT Control DNA (Promega, Madison, Wis.) was precipitated with CaCl$_2$ and ethanol. The dried DNA pellet was resuspended in 1 milliliter of the 1 mg/ml lipid suspension and allowed to incubate at room temperature for 1 hour. The lipid-DNA complex was then collected by centrifugation at 12K rpm in an Eppendorf centrifuge 5415C (BrinkmanInstr. Inc., Westbury, N.Y. 11590). The supernatantwas removed to another tube and the pelleted lipid-DNA complex was resuspended in a minimal volume of dI H$_2$O. The supernatant and the pellet sultions were assayed for DNA using a Hoefer TKO 100 Fluorometer (Hoefer Scientific Instruments, San Francisco, Calif. 94117). The DNA concentration in the supernatant was 5 μg/μl and the DNA concentration in the lipid-DNA pelleted complex was 1572 μg/μl, indicating that the DNA was complexed with the lipid.

Example 7

Dry lipids were weighed out and hydrated in dI H$_2$O by heating and stirring in the mole percentage ratio of 25 mol % DMPC to 75 mol % DMPA and then lyopholized. A small vial was rinsed with dI H$_2$O and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered dI H$_2$O was added by weight until the final concentration of lipid was 1 mg/ml. This mixture was heated to 45–50° C. for 1 hour and then sonicated in a Aquasonic cleaner Model 75 HT (VWR) at room temperature for 1 hour in 30 minute increments to prevent excessive heating.

200 μg of pCAT Control DNA (Promega, Madison, Wis.) was precipitated with CaCl$_2$ and ethanol. The dried DNA pellet was resuspended in 1 milliliter of the 1 mg/ml lipid suspension and allowed to incubate at room temperature for 1 hour. The lipid-DNA complex was then collected by centrifugation at 12K rpm in an Eppendorf centrifuge 5415C (Brinkman Instr. Inc., Westbury, N.Y. 11590). The supernatant was removed to another tube and the pelleted lipid-DNA complex was resuspended in a minimal volume of dl H$_2$O. The supernatant and the pellet sultions were assayed for DNA using a Hoefer TKO 100 Fluorometer (Hoefer Scientific Instruments, San Francisco, Calif. 94117). The DNA concentration in the supernatant was 0 μg/μl and the DNA concentration in the lipid-DNA pelleted complex was 67 μg/μl, indicating that the DNA was complexed with the lipid.

Example 8

Dry lipids were weighed out and hydrated in dI H$_2$O by heating and stirring in the mole percentage ratio of 70 mol % DMPC to 20 mol % DMPA to 10 mol % DMPE-PEG5,000, and then lyophilized. A small vial was rinsed with dI H2O and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered dl H$_2$O was added by weight until the final concentration of lipid was 1 mg/ml. This mixture was heated to 45–50° C. for 1 hour and then sonicated in a Aquasonic cleaner Model 75 HT (VWR) at room temperature for 1 hour in 30 minute increments to prevent excessive heating.

200 μg of pCAT Control DNA (Promega, Madison, Wis.) was precipitated with CaCl$_2$ and ethanol. The dried DNA pellet was resuspended in 1 milliliter of the 1 mg/ml lipid suspension and allowed to incubate at room temperature for 1 hour. The lipid-DNA complex was then collected by centrifugation at 12K rpm in an Eppendorf centrifuge 5415C (Brinkman Instr. Inc., Westbury, N.Y. 11590). The supernatant was removed to another tube and the pelleted lipid-DNA complex was resuspended in a minimal volume of dI $H_2O$. The supernatant and the pellet sultions were assayed for DNA using a Hoefer TKO 100 Fluorometer (Hoefer Scientific Instruments, San Francisco, Calif. 94117). The DNA concentration in the supernatant was 43 μg/μl and the DNA concentration in the lipid-DNA pelleted complex was 1791 μg/μl, indicating that the DNA was complexed with the lipid.

Example 9

Dry lipids were weighed out and hydrated in dI $H_2O$ by heating and stirring in the mole percentage ratio of 20 mol % DMPC to 70 mol % DMPA to 10 mol % DMPE-PEG5000, and then lyophilized. A small vial was rinsed with dI $H_2O$ and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered dI $H_2O$ was added by weight until the final concentration of lipid was 1 mg/ml. This mixture was heated to 45–50C. for 1 hour and then sonicated in a Aquasonic cleaner Model 75 HT (VWR) at room temperature for 1 hour in 30 minute increments to prevent excessive heating.

200 μg of pCAT Control DNA (Promega, Madison, Wis.) was precipitated with $CaCl_2$ and ethanol. The dried DNA pellet was resuspended in 1 milliliter of the 1 mg/ml lipid suspension and allowed to incubate at room temperature for 1 hour. The lipid-DNA complex was then collected by centrifugation at 12K rpm in an Eppendorf centrifuge 5415C (Brinkman Instr. Inc., Westbury, N.Y. 11590). The supernatant was removed to another tube and the pelleted lipid-DNA complex was resuspended in a minimal volume of dI $H_2O$. The supernatant and the pellet sultions were assayed for DNA using a Hoefer TKO 100 Fluorometer (Hoefer Scientific Instruments, San Francisco, Calif. 94117). The DNA concentration in the supernatant was 28 μg/μl and the DNA concentration in the lipid-DNA pelleted complex was 6800 μg/μl, indicating that the DNA was complexed with the lipid.

Example 10

Dry lipids were weighed out and hydrated in dI $H_2O$ by heating and stirring in the mole percentage ratio of 20 mol % DMPC to 70 mol % DMPA to 10 mol % DMPE-PEG5000. A small vial was rinsed with dI $H_2O$ and tared on a Mettler AJ100 (Mettler Instrument Corp. PO Box 71, Hightstown, N.J., 08520) balance and five to ten milligrams of the lyopholized lipid blend was weighed into the vial. Triple 0.22 μm filtered dI $H_2O$ was added by weight until the final concentration of lipid was 1 mg/ml. This mixture was heated to 45–50° C. for 1 hour and then sonicated in a Aquasonic cleaner Model 75 HT (VWR) at room temperature for 1 hour in 30 minute increments to prevent excessive heating.

200 μg of pCAT Control DNA (Promega, Madison, Wis.) was precipitated with $CaCl_2$ and ethanol. The dried DNA pellet was resuspended in 1 milliliter of the 1 mg/ml lipid suspension and allowed to incubate at room temperature for 1 hour. The lipid-DNA complex was then collected by centrifugation at 12K rpm in an Eppendorf centrifuge 5415C (Brinkman Instr. Inc., Westbury, N.Y. 11590). The supernatant was removed to another tube and the pelleted lipid-DNA complex was resuspended in a minimal volume of dI $H_2O$. The supernatant and the pellet sultions were assayed for DNA using a Hoefer TKO 100 Fluorometer (Hoefer Scientific Instruments, San Francisco, Calif. 94117). The DNA recovered in the supernatant was 183 μg and the total DNA in the pellet was 14.1 μg, indicating essentially no complexation of DNA with lipid in the absence of calcium.

In Examples 11 and 12, dexamethasone was added to selected compositions from the preceding Examples to determine the level of entrappment.

Example 11

Dexamethasone is a highly potent hydrophobic drug that is soluble at 100 mg/L in water. A mixture was weighed out in the ratio of 65 mol % DPPA to 15 mol % DPPC to 20 mol % dexamethasone. This mixture was dissolved in methanol and rotary evaporated under vacuum until it was a dry film. The film was subjected to hard vacuum overnight. The film was resuspended in deionized water at 1 mg/ml and sonicated for 5 minutes. The resulting suspension was homogeneous. 100 mM $CaCl_2$ was added dropwise while sonicating the suspension to a final concentration of 10 mM. This resulted in the aggregation of the lipids and their subsequent precipitation from the solution. The cochleates were sonicated for one half hour at 90 watts with no change in characteristics. The resulting compositions were too large and nonhomogeneous without the polymer-bearing lipid.

Example 12

Dexamethasone is soluble at 100 mg/L in water. A mixture was created by adding 80 mg of the lipid blend to 20 mg of dexamethasone. The lipid blend was 70 mol % DMPA, 20 mol % DMPC and 10 mol % DMPE-PEG5000. The blend and the dexamethasone were dissolved in methanol and rotary evaporated under vacuum until it was a dry film. The film was subjected to hard vacuum overnight. The film was resuspended in deionized water at 10 mg/ml and sonicated for 15 minutes at 90 watts. The resulting suspension was homogeneous. 100 mM $CaCl_2$ was added dropwise while sonicating the suspension to a final concentration of 10 mM. There was no visible change it the solution characteristics after the addition of the cacium chloride solution which is consistent with prior results showing no real change in size of the particles by QELS. One milliliter of this mixture was administered to a Sephacryl S-200-HR column ½" by 7" running in deionized water at 1 ml/minute, collecting 3 ml fractions. The column was charaterised with a mixture of a fluoresent lipid blend of DPPE and DPPC and bromophenol blue, a visible dye. The lipid was separated from the dye. The lipid eluted in the 3rd and 4th fractions and the dye began in the 10th fraction and was strongest in the 12th through the 17th fractions. Fractions 3 and 4 from the mixture of dexamethasone and lipid blend were translucent with suspended lipid. All of the remaining 80 fractions were clear. The fractions were frozen in liquid nitrogen and lyopholized. The lyophilized fractions were dissolved or resuspended in 5 mls of methanol and scanned at 235 nm in the UV spectrophotometer. The absorbance maximum for dexamethasone in methanol was 235–238 nm as determined by dissolving dexamethasone in methanol and scanning from 320 nm through 220 nm. Pure methanol was scanned between 320 nm and 190 nm and was found to have no absorbance below 210 nm. All samples were zeroed on pure methanol before scanning to prevent any carryover between samples. A standard curve was constructed from dexamethasone in methanol at 237 nm peak absorbance. The standard curve was between 2.5 and 25 ug/ml. The fractions that contained lipid were suspensions and could not be scanned accurately. The remaining fractions were scanned and presumably contained the free, unentrapped dexamethasone. The majority of the dexamethasone absorbance was in fractions 11 through 15. The entire recovered free dexamethasone was only 7.3 μg. 2 mgs were loaded on to the column in the 1 ml aliquot of the mixture which was 10 mg/ml, 20% of which was dexamethasone. The experiment suggested that the compositions of the present invention may achieve high payloads of dexamethasone.

Example 13

The lipid preparation of Example 2 in 10 mM $CaCl_2$ is lyophilized immediately after the sonication step. A cryoprotectant, such as mannitol, glycerol, sorbitol or trehalose, is added to 1.0 mg/ml. After lyophilization, the powdered sample is stored or resuspended in $dH_2O$.

Example 14

The lipid preparation of Example 2 in 10 mM $CaCl_2$ is lyophilized immediately after the sonication step. The sample contains PEG-2000 (2:1 w/w) over the weight of the lipid mixture as a substitute cryoprotectant for the sugars and sugar alcohols in Example 13. After lyophilization, the powdered sample is stored or resuspended in $dH_2O$.

Example 15

Lyophilized compositions may be stored under a head space of a preselected gas, as described herein. The compositions from Example 14 were placed in a sealed vessel and the head space of the air was evacuated and replaced with perfluoropropane. The result was a plurality of microvoids within and on the surface of the compositions filled by perfluoropropane gas. When the compositions were rehydrated, acoustic analysis showed the particles to be acoustically active. Optimal acoustic attenuation was achieved when the mixture was gently hand shaken during reconstitution with saline rather than mixed in an ESPE Capmix.

Example 16

A lipid blend of 82 mole % dipalmitoylphosphatidylcholine, 8 mole % dipalmitoylphophatidic acid, 10 mole % diplmitoylphosphatidylethanolamine-PEG 5000 was prepared with $CaCl_2$ as in Example 2. Perfluorohexane was added to the mixture at a concentration of 10 mg/ml. This material was then extruded through an extrusion device (Lipex Biomembranes, Vancouver, B.C. Canada). The extrusion was accomplished under nitrogen pressure at 1000 psi. First the material was passed through 2 μm filter, then through 1 μm filter and then through a 0.4 μm filter five times. The material was then sized by a quasi-elastic light scattering device (Particle Sizing Systems, Santa Barbara, Calif.) mean diameter of the particles was about 200–500 nm.

Example 17

A lipid blend of 82 mole % dipalmitoylphosphatidylcholine, 8 mole % dipalmitoylphophatidic acid, 10 mole % diplmitoylphosphatidylethanolamine-PEG 5000 was prepared with $CaCl_2$ as in Example 2. Perfluoropentane was added to the mixture at a concentration of 10 mg/ml. This material was then extruded through an extrusion device (Lipex Biomembranes, Vancouver, B.C. Canada). The extrusion was accomplished under nitrogen pressure at 1000 psi. First the material was passed through 2 μm filter, then through 1 μm filter and then through a 0.4 μm filter five times. The material was then sized by a quasi-elastic light scattering device (Particle Sizing Systems, Santa Barbara, Calif.) mean diameter of the particles was about 200–500 nm.

Example 18

A volatile organic solvent, preferably a perfluorocarbon, most preferably 1-bromoperfluorobutane, is incorporated into the core of the compositions before the aggregation process (see Example 1). The compositions are then lyophilized, resulting in porous, solid structures. These are stored under a head space of air or an insoluble gas such as perfluoropropane or sulfur hexafluoride. The resulting porous gas-filled compositions are acoustically active. The drugs listed in the disclosure of the present invention can be incorporated into the compositions for delivery with or without ultrasound according to the methods described above.

The disclosure of each patent, patent application and publication cited or described in this document is hereby incorporated by reference herein in its entirety.

Various modifications of the invention, in addition to those described herein, will be apparent to one skilled in the art from the foregoing description. Such modifications are also intended to fall within the spirit and scope of the appended claims.

What is claimed is:

1. A contrast agent comprising a cochleate which comprises a charged lipid, a counter ion, a lipid covalently bonded to a polymer, and a gas, a gaseous precursor or a gas and a gaseous precursor, wherein the gas and gaseous precursor comprise fluorinated compounds.

2. The contrast agent of claim 1, wherein the charged lipid is an anionic lipid and the counter ion is a cationic counter ion.

3. The contrast agent of claim 2, wherein the anionic lipid is selected from the group consisting of a phosphatidic acid, a phosphatidyl glycerol, a phosphatidyl glycerol fatty acid ester, a phosphatidyl ethanolamine anandamide, a phosphatidyl ethanolamine methanandamide, a phosphatidyl serine, a phosphatidyl inositol, a phosphatidyl inositol fatty acid ester, a cardiolipin, a phosphatidyl ethylene glycol, an acidic lysolipid, a sulfolipid, a sulfatide, a saturated free fatty acid, an unsaturated free fatty acid, a palmitic acid, a stearic acid, an arachidonic acid, an oleic acid, a linolenic acid, a linoleic acid, and a myristic acid.

4. The contrast agent of claim 2, wherein the cationic counter ion is selected from the group consisting of $Be^{2+}$, $Mg^{2+}$, $Ca^{2+}$, $Sr2+$, $Ba^{2+}$, $Al^{3+}$, $Ga^{3+}$, $Ge^{3+}$, $Sn^{4+}$, $Pb^{2+}$, $Pb^{4+}$, $Ti^{3+}$, $Ti^{4+}$, $V^{2+}$, $V^{3+}$, $Cr^{2+}$, $Cr^{3+}$, $Mn^{2+}$, $Mn^{3+}$, $Fe^{2+}$, $Fe^{3+}$, $Co^{2+}$, $Co^{3+}$, $Ni^{2+}$, $Ni^{3+}$, $Cu^{2+}$, $Zn^{2+}$, $Zr^{4+}$, $Nb^{3+}$, $Mo^{2+}$, $Mo^{3+}$, $Cd^{2+}$, $In^{3+}$, $W^{2+}$, $W^{4+}$, $Os^{2+}$, $Os^{3+}$, $Os^{4+}$, $Ir^{2+}$, $Ir^{3+}$, $Ir^{4+}$, $Hg^{2+}$, $Bi^{3+}$, $La^{3+}$, and $Gd^{3+}$.

5. The contrast agent of claim 4, wherein the cationic counter ion is selected from the group consisting of $Ca^{2+}$, $Mg^{2+}$, $Zn^{2+}$, $Mn^{2+}$ and $Gd^{3+}$.

6. The contrast agent of claim 5, wherein the cationic counter ion is $Ca^{2+}$.

7. The contrast agent of claim 1, wherein, in the lipid covalently bonded to the polymer, the polymer is selected from the group consisting of polyethylene glycol, polyvinyl pyrrolidone, polyvinyl alcohol, polypropylene glycol, a polyvinylalkylether, a polyacrylamide, a polyalkyloxazoline, a polyhydroxyalkyloxazoline, a polyphosphazene, a polyoxazolidine, a polyaspartamide, a polymer of sialic acid, a polyhydroxyalkyl(meth)acrylate and a poly(hydroxyalkylcarboyxlic acid).

8. The contrast agent of claim 7, wherein, in the lipid covalently bonded to the polymer, the polymer is polyethylene glycol.

9. The contrast agent of claim 8, wherein the polyethylene glycol has a molecular weight of from about 1,000 to about 10,000.

10. The contrast agent of claim 1, wherein the lipid covalently bonded to the polymer is selected from the group consisting of dipalmitoylphosphatidylethanolamine-polyethylene glycol, dioleoylphosphatidylethanolamine-polyethylene glycol and distearylphosphatidylethanolamine-polyethylene glycol.

11. The contrast agent of claim 2, wherein the anionic lipid is dipalmitoyl-phosphatidic acid, the cationic counter ion is $Ca^{2+}$ and the lipid covalently bonded to the polymer is dipalmitoylphosphatidylethanolamine-polyethylene glycol.

12. The contrast agent of claim 1, further comprising at least one lipid having a neutral charge.

13. The contrast agent of claim 1, further comprising a targeting ligand.

14. The contrast agent of claim 13, wherein the targeting ligand is selected from the group consisting of peptides, proteins and saccharides.

15. The contrast agent of claim 1, wherein the fluorinated compound is selected from the group consisting of a perflurocarbon, sulfur hexafluoride and a perfluoroether.

16. The contrast agent of claim 15, wherein the fluorinated compound is a perfluorocarbon selected from the group consisting of perfluoromethane, perfluoroethane, perfluoropropane, perfluorocyclopropane, perfluorobutane, perfluorocyclobutane, perfluoropentane and perfluorocyclopentane.

17. The contrast agent of claim 15, wherein the fluorinated compound is a perfluoroether selected from the group consisting of perfluorotetrahydropyran, perfluoromethyltetrahydrofuran, perfluorobutylmethyl ether, perfluoropropylethyl ether, perfluorocyclobutylmethyl ether, perfluorocyclopropylethyl ether, perfluoropropylmethyl ether, perfluorodiethyl ether, perfluorocyclopropylmethyl ether, perfluoromethylethyl ether and perfluorodimethyl ether.

18. The contrast agent of claim 1, further comprising a fluorinated liquid.

19. The contrast agent of claim 18, wherein the fluorinated liquid is selected from the group consisting of perfluorohexane, perfluoroheptane, perfluorooctane, perfluorononane, perfluorodecane, perfluorododecane, perfluorocyclohexane, perfluorodecalin, perfluorododecalin, perfluorooctyliodide, perfluorooctylbromide, perfluorotripropylamine, perfluorotributylamine, perfluorobutylethyl ether, bis(perfluoroisopropyl) ether and bis(perfluoropropyl) ether.

20. A contrast agent of claim 1 wherein said cochleate is in the form of a spiral or tubule.

* * * * *

UNITED STATES PATENT AND TRADEMARK OFFICE
CERTIFICATE OF CORRECTION

PATENT NO.     : 6,120,751
DATED          : September 19, 2000
INVENTOR(S)    : Evan C. Unger It is certified that error appears in the above-identified patent and that said Letters Patent is hereby corrected as shown below:

Title Page
Item [63], Related U.S. Application Data, please insert -- , now allowed -- after "Mar. 21, 1997"; please insert -- , now allowed -- after "May 6, 1997"; please insert -- , now U.S. 6,028,066 -- after "Jul. 2, 1997".
Item [56], References Cited, U.S. PATENT DOCUMENTS, please delete "4,775,958" and insert -- 4,774,958 -- therefor.
OTHER PUBLICATIONS,
"Mahlradt et al.," reference, please delete "Mahlradt" and insert -- Muhlradt -- therefor.
"Fukuda et al.," reference, please delete "Diotadecyldimethylammonium" and insert -- Dioctadecyldimethylammonium -- therefor.
"Shiina et al.," reference, please delete "Hyperthermiaby" and insert -- Hyperthermia by -- therefor.
"Pozansky et al.," reference, please delete "Pozansky" and insert -- Poznansky --, and, also, please delete "Biologica" and insert -- Biological -- therefor.
"Ter-Pogossia," reference, please delete "Ter-Pogossia *Tomography*, Kee et al., n," and insert -- Ter-Pogossian --; and, after "*Computed Body*", please insert -- *Tomography*, Lee et al., -- therefor.
"Aronberg," reference, please delete "Kee" and insert -- Lee -- therefor.
"Keller et al.", reference, please delete "Microcirulation" and insert -- Microcirculation -- therefor.
"Lubinski et al.," reference, please delete "Kine" and insert -- Line -- therefor.
"Van Dougen et al.," reference, delete "Van Dougen" and insert -- Van Dongen -- therefor.
"Holland t al.," reference, please delete "t al." and insert -- et al. --; and, please delete "Composed o" and insert -- Composed of -- therefor.
"Silvius et al.," reference, please delete "Vesclies." and insert -- Vesicles -- therefor.
"Zalipsky", reference, please delete "Polytheylene" and insert -- Polyethylene -- therefor (both occurrences).

Column 1,
Line 6, please insert -- , now allowed -- after "Mar. 21, 1997".
Line 7, please insert -- , now allowed -- after "May 6, 1997".
Line 10, please insert -- now U.S. Patent No. 6,028,066 -- after "July 2, 1997".
Line 12, please delete "hirein" and insert -- herein -- therefor.
Line 61, please delete "subjet" and insert -- subject -- therefor.

Column 4,
Line 35, please delete "inchlde" and insert -- include -- therefor.

Column 7,
Line 63, please delete "Droplef" and insert -- Droplet -- therefor.

UNITED STATES PATENT AND TRADEMARK OFFICE
CERTIFICATE OF CORRECTION

PATENT NO. : 6,120,751
DATED : September 19, 2000
INVENTOR(S) : Evan C. Unger

It is certified that error appears in the above-identified patent and that said Letters Patent is hereby corrected as shown below:

Column 10,
Line 42, please delete "from" and insert -- form -- therefor.

Column 11,
Line 20, please delete "glyercol" and insert -- glycerol -- therefor.
Line 46, please delete "boned" and insert -- bonded -- therefor.

Column 13,
Line 12, please delete "quatemary" and insert -- quarternary -- therefor.

Column 16,
Lines 5-13, please delete

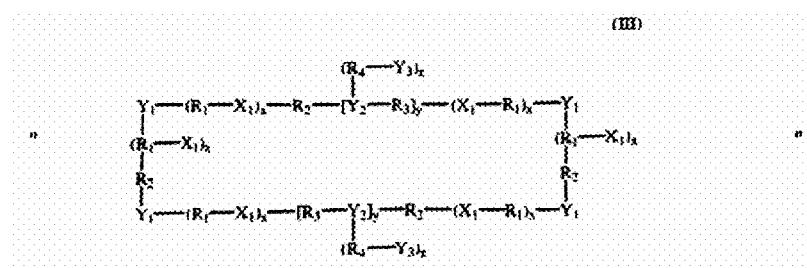

and insert

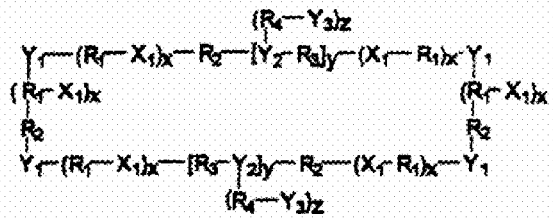

therefor.

Column 18,
Line 15, please delete "(dodecyaminocarbonylmethylene)" and insert
-- (dodecylaminocarbonylmethylene) -- therefor.

Column 19,
Line 1, please delete "polyhyhydroxypropyloxazolines" and insert
-- polyhydroxypropyloxazolines -- therefor.

UNITED STATES PATENT AND TRADEMARK OFFICE
CERTIFICATE OF CORRECTION

PATENT NO.   : 6,120,751
DATED        : September 19, 2000
INVENTOR(S)  : Evan C. Unger It is certified that error appears in the above-identified patent and that said Letters Patent is hereby corrected as shown below:

Column 20,
Line 61, please delete "decribed" and insert -- described -- therefor.

Column 21,
Line 21, please delete "my" and insert -- may -- therefor.

Columns 23□24,
Please delete Compound I

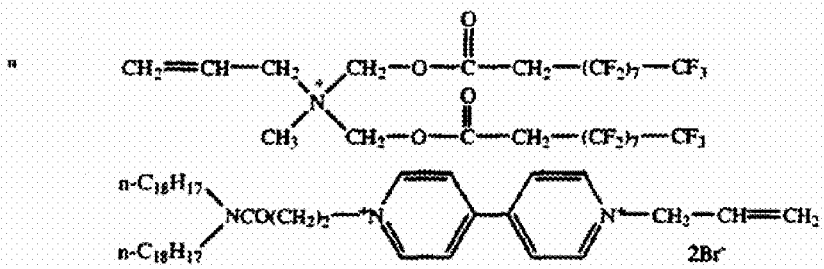

and insert

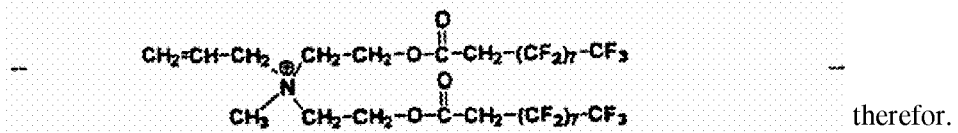

therefor.

Column 27,
Line 18, please insert -- may -- after "lipid".

Column 31,
Line 38, please delete "providedthatthe" and insert -- provided that the -- therefor.

Column 32,
Line 67, please delete "heptafluorobutyiyl" and insert -- heptafluorobutyryl -- therefor.

Column 33,
Line 27, please delete "palnitate" and insert -- palmitate -- therefor.

Column 34,
Line 1, please delete "galatocarolose" and insert -- galactocarolose -- therefor.
Line 48, please delete "sulfonal:ed" and insert -- sulfonated -- therefor.

UNITED STATES PATENT AND TRADEMARK OFFICE
CERTIFICATE OF CORRECTION

PATENT NO. : 6,120,751
DATED : September 19, 2000
INVENTOR(S) : Evan C. Unger

It is certified that error appears in the above-identified patent and that said Letters Patent is hereby corrected as shown below:

Column 35,
Line 17, please delete "hydrophobichydrophilic" and insert
-- hydrophobic☐hydrophilic -- therefor.

Column 37,
Line 42, please delete "norbomane" and insert -- norbornane -- therefor.
Line 45, please delete "metbyl" and insert -- methyl -- therefor.
Line 59, please delete "... nitrothiopbene" and insert -- …nitrothiophene -- therefor.
Line 60, please delete "...cylohexene" and insert -- ...cyclohexene -- therefor.

Column 38,
Line 18, please delete "either" and insert -- ether -- therefor.
Line 26, please delete "becomed" and insert -- become -- therefor.
Line 38, please delete "perfllioro" and insert -- perfluoro -- therefor.

Column 39,
Lines 40, 48 and 51, please insert -- . -- after "thereof".

Column 42,
Line 30, please delete "arid" and insert -- and -- therefor.
Line 60, please delete "metoproteronol" and insert -- metaproterenol -- therefor.

Column 43,
Line 11, please delete "fluorourcil" and insert -- fluorouracil -- therefor.

Column 47,
Line 3, please delete "is" and insert -- as -- therefor.
Line 22, please delete "BALEI/c" and insert -- BALB/c -- therefor.
Line 23, please delete "hybridomtas" and insert -- hybridomas -- therefor.
Line 33, please delete "ligarld" and insert -- ligand -- therefor.

Column 48,
Line 22, please delete "anima" and insert -- animal -- therefor.
Line 49, please delete "endotheli,al" and insert -- endothelial -- therefor.

Column 50,
Line 16, please delete "aikyl" and insert -- alkyl -- therefor.

Column 51,
Line 31, please delete "cr" and insert -- or -- therefor.

UNITED STATES PATENT AND TRADEMARK OFFICE
CERTIFICATE OF CORRECTION

PATENT NO. : 6,120,751
DATED : September 19, 2000
INVENTOR(S) : Evan C. Unger

It is certified that error appears in the above-identified patent and that said Letters Patent is hereby corrected as shown below:

Column 52,
Line 41, please delete "alky" and insert -- alkyl -- therefor.

Column 54,
Line 25, please delete "L-2" and insert -- IL-2 -- therefor.

Column 55,
Line 65, please delete "is" and insert -- are -- therefor.

Column 56,
Line 20, please delete "polyhyhydroxypropyloxazolines" and insert
-- polyhydroxypropyloxazolines -- therefor.

Column 57,
Line 35, please delete "t-butyloxycarbony" and insert -- t-butyloxycarbonyl -- therefor.
Line 37, please delete the second occurrence of "and".

Column 59,
Line 11, please delete "ink" and insert -- in -- therefor.

Column 60,
Line 57, please delete "is".

Column 61,
Line 58, please delete "ω-glucopyranpsyl-..." and insert -- ω-glucopyranosyl -- therefor.

Column 62,
Line 49, please delete "...(=O)—CH,CH$_2$—..." and insert -- ...(=O)—CH$_2$CH$_2$—... --
therefor.

Column 65,
Line 19, please delete "Lechtenstein" and insert -- Liechtenstein -- therefor.

Column 68,
Line 55, please delete "bout" and insert -- about -- therefor.
Line 56, please delete "o about " and insert -- to about -- therefor.

Column 71,
Line 61, please delete "... R1/T$_o$–1/T)" and insert -- ... R(1/T$_o$–1/T) -- therefor.

UNITED STATES PATENT AND TRADEMARK OFFICE
CERTIFICATE OF CORRECTION

PATENT NO.   : 6,120,751
DATED        : September 19, 2000
INVENTOR(S)  : Evan C. Unger It is certified that error appears in the above-identified patent and that said Letters Patent is hereby corrected as shown below:

Column 76,
Lines 52 and 54, please delete "compositionss" and insert -- compositions -- therefor.

Column 84,
Line 37, please delete "compositionss" and insert -- compositions -- therefor.

Column 91,
Lines 5, 29, 64 and 67, please delete "lyopholized" and insert -- lyophilized -- therefor.

Column 92,
Lines 26, 29 and 59, please delete "lyopholized" and insert -- lyophilized -- therefor.
Line 45, please delete "sultions" and insert -- solutions -- therefor.

Column 93,
Lines 8 and 39, please delete "sultions" and insert -- solutions -- therefor.
Lines 22 and 53, please delete "lyopholized" and insert -- lyophilized -- therefor.

Column 94,
Line 10, please delete "entrappment" and insert -- entrapment -- therefor.
Line 43, please delete "cacium" and insert -- calcium -- therefor.
Line 48, please delete "charaterised" and insert -- characterized -- therefor.
Line 49, please delete "fluoresent" and insert -- fluorescent -- therefor.
Line 57, please delete "lyopholized" and insert -- lyophilized -- therefor.

Signed and Sealed this

Sixteenth Day of March, 2004

JON W. DUDAS
*Acting Director of the United States Patent and Trademark Office*